(12) United States Patent
Walsh et al.

(10) Patent No.: US 11,702,629 B2
(45) Date of Patent: Jul. 18, 2023

(54) ACCELERATION OF STEM CELL DIFFERENTIATION

(71) Applicant: Regents of the University of Minnesota, Minneapolis, MN (US)

(72) Inventors: Patrick Joseph Walsh, Minneapolis, MN (US); James Robert Dutton, Hudson, WI (US); Ann Margaret Parr, Excelsior, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 552 days.

(21) Appl. No.: 16/611,781

(22) PCT Filed: May 8, 2018

(86) PCT No.: PCT/US2018/031673
§ 371 (c)(1),
(2) Date: Nov. 7, 2019

(87) PCT Pub. No.: WO2018/208836
PCT Pub. Date: Nov. 15, 2018

(65) Prior Publication Data
US 2020/0063097 A1 Feb. 27, 2020

Related U.S. Application Data

(60) Provisional application No. 62/503,088, filed on May 8, 2017.

(51) Int. Cl.
*C12N 5/0735* (2010.01)
*C07K 16/22* (2006.01)

(52) U.S. Cl.
CPC ............ *C12N 5/0606* (2013.01); *C07K 16/22* (2013.01); *C12N 2501/115* (2013.01); *C12N 2501/727* (2013.01); *C12N 2501/998* (2013.01)

(58) Field of Classification Search
CPC .................................................. C12N 5/0606
See application file for complete search history.

(56) References Cited

FOREIGN PATENT DOCUMENTS

| AU | 2015203079 A1 | 7/2015 | | |
|---|---|---|---|---|
| EP | 2497825 A1 | 9/2012 | | |
| JP | 2020-518277 A | 6/2020 | | |
| WO | WO-2010077955 A1 * | 7/2010 | ............... | C12N 1/00 |
| WO | WO-2010077955 A1 | 7/2010 | | |
| WO | WO-2010124290 A2 | 10/2010 | | |
| WO | WO-2018208836 A1 | 11/2018 | | |

OTHER PUBLICATIONS

Li et al (2015, J. Mol. Cell Biol., vol. 7(5), pp. 455-465). (Year: 2015).*

"Cellular & Gene Therapy Guidances", U.S. Food & Drug Administration, [Online]. Retrieved from the internet: <URL: https://www.fda.gov/BiologicsBloodVaccines/GuidanceComplianceRegulatoryInformation/Guidances/CellularandGeneTherapy/default.htm>, (Sep. 15, 2016), 3 pgs.
"Considerations for the Design of Early-Phase Clinical Trials of Cellular and Gene Therapy Products Guidance for Industry", U.S. Department of Health and Human Services Food and Drug Administration Center for Biologics Evaluation and Research, (Jun. 2015), 27 pgs.
"Guidance for Industry Potency Tests for Cellular and Gene Therapy Products", U.S. Department of Health and Human Services Food and Drug Administration Center for Biologics Evaluation and Research, [Online]. Retrieved from the Internet: <URL: https://www.fda.gov/downloads/BiologicsBloodVaccines/GuidanceComplianceRegulatoryInformation/Guidances/CellularandGeneTherapy/UCM243392.pdf>, (Jan. 2011), 19 pgs.
"Guidance for Industry Preciinical Assessment of Investigational Cellular and Gene Therapy Products", U.S. Department of Health and Human Services Food and Drug Administration Center for Biologics Evaluation and Research, [Online]. Retrieved from the Internet: <URL: https://www.fda.gov/downloads/BiologicsBioodVaccines/GuidanceComplianceRegulatoryInformation/Guidances/CellularandGeneTherapy/UCM376521.pdf>, (Nov. 2013), 35 pgs.
"Homologous Use of Human Cells,Tissues, and Cellular and Tissue-Based Products", U.S. Department of Health and Human Services Food and Drug Administration Center for Biologics Evaluation and Research (CBER) Center for Devices and Radiological Health (CDRH) Office of Combination Products (OCR), [Online]. Retrieved from the Internet: <URL: https://www.fda.gov/downloads/BiologicsBloodVaccines/GuidanceComplianceRegulatoryInformation/Guidances/Tissue/UCM469751.pdf>, (Oct. 2015), 10 pgs.
"International Application Serial No. PCT/US2018/031673, International Search Report dated Aug. 10, 2018", 5 pgs.
"International Application Serial No. PCT/US2018/031673, Written Opinion dated Aug. 10, 2018", 9 pgs.
Beattie, Gillian, et al., "Activin A Maintains Pluripotency of Human Embryonic Stem Cells in the Absence of Feeder Layers", Stem Cells 23, (2005), 489-495.
Chambers, Stuart M., et al., "Highly efficient neural conversion of human ES and iPS cells by dual inhibition of SMAD signaling", NIH Public Access, Published in final edited form as: Nat Biotechnol 27(3), (2009), 275-280.
Chen, Guokai, et al., "Chemically defined conditions for human ipsc derivation and culture", Nat Methods, 8(5), (2011), 424-429.
Cong, Le, et al., "Multiplex Genome Engineering Using CRISPR/Cas Systems", Science 339(6121), (Feb. 15, 2013), 819-823.
Howden, Sara E, et al., "Simultaneous Reprogramming and Gene Correction of Patient Fibroblasts", Stem Cell Reports 5(6), (2015), 1109-1118.
Itskovitz-Eldor, J., et al., "Differentiation of Human Embryonic Stem Cells Into Embryoid Bodies Compromising the Three Embryonic Germ Layers", Molecular Medicine, 6(2), (2000), 88-95.

(Continued)

*Primary Examiner* — Anoop K Singh
*Assistant Examiner* — David A Montanari
(74) *Attorney, Agent, or Firm* — Schwegman Lundberg & Woessner, P.A.

(57) ABSTRACT

Provide herein are compositions, methods and kits to accelerate pluripotent stem cell differentiation.

6 Claims, 38 Drawing Sheets

(56) References Cited

OTHER PUBLICATIONS

Figure 2C:
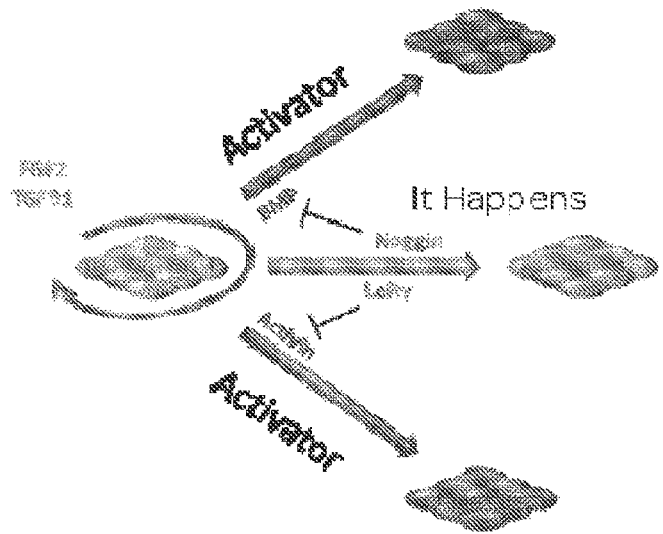

Jaeger, Ines, et al., "Temporally controlled modulation of FGF/ERK signaling directs midbrain dopaminergic neural progenitor fate in mouse and human pluripotent stem cells", Development 138(20), (2011), 4363-4374.

Jin, Sha, et al., "A Synthetic Xeno-Free Peptide Surface for Expansion and Directed Differentiation of Human Induced Pluripotent Stem Cells", PLOS ONE vol. 7 No. 11, (Nov. 30, 2012), e50880.

Jin, Sha, et al., "A Synthetic, Xeno-Free Peptide Surface for Expansion and Directed Differentiation of Human Induced Pluripotent Stem Cells", PLoS One 7(11) e50880, (Nov. 2012), 1-10.

Kang, Hyun-Wook, et al., "A 3D bioprinting system to produce human-scale tissue constructs with structural integrity", Nat Biotechnol 34(3), (Mar. 2016), 312-322.

Lippmann, Ethan Scott, et al., "Defined Human Pluripotent Stem Cell Culture Enables Highly Efficient Neuroepithelium Derivation Without Small Molecule Inhibitors", Stem Cells 32(4), (2013), 1032-1042.

Lippmann, Ethan S, et al., "Deterministic HOX Patterning in Human Pluripotent Stem Cell-Derived Neuroectoderm", Stem Cell Reports vol. 4 No. 4, (Apr. 1, 2015), 632-644.

Ludwig, Tenneille E, et al., "Derivation of human embryonic stem cells in defined conditions", Nat Biotechnol. 24(2), (2006), 185-187.

Martin, Benjamin L, "Factors that coordinate mesoderm specification from neuromesodermal progenitors with segmentation during vertebrate axial extensio", Seminars in Cell and Developmental Biology vol. 49, (Jan. 1, 2016), 59-67.

Miyazaki, Takamichi, et al., "Laminin E8 fragments support efficient adhesion and expansion of dissociated human pluripotent stem cells", Nat Communications 3:1236, (Dec. 4, 2012), 1-10.

Nagaoka, Masato, et al., "Culture of human pluripotent stem cells using completely defined conditions on a recombinant e-cadherin substratum", BMC Dev Biol. 10:60, (2009), 12 pgs.

Nagaoka, Masato, et al., "Design of a Vitronectin-Based Recombinant Protein as a Defined Substrate for Differentiation of Human Pluripotent Stem Cells into Hepatocyte-Like Cells", PLoS One 10(8) e0136350, (Aug. 26, 2015), 1-17.

Perrier, Anselme L., et al., "Derivation of midbrain dopamine neurons from human embryonic stem cells", Proc Natl Acad Sci U S A. 101(34), (Aug. 24, 2004), 12543-12548.

Reid, John A., et al., "Accessible bioprinting: adaptation of a low-cost 3D-printer for precise cell placement and stem cell differentiation", Biofabrication 8(2016) 025017 doi:10.1088/1758-5090/8/2/025017, (2016), 13 pgs.

Rosler. Elen S., et al., "Long-term culture of human embryonic stem cells in feeder-free conditions", Developmental Dynamics 229(2), (2004), 259-274.

Sharma, Arun, et al., "Human Induced Pluripotent Stem Cell-Derived Cardiomyocytes as an In Vitro Model for Coxsackievirus B3-Induced Myocarditis and Antiviral Drug Screening Platform", Circulation Research 115(6), (2014), 556-566.

Song, Jiwon, et al., "Economic 3D-printing approach for transplantation of human stem cell-derived β-like cells", Biofabrication 9 (2017) 015002 doi:10.1088/1758-5090/9/1/015002, (2017), 15 pgs.

Takahashi, Kazutoshi, et al., "Induction of Pluripotent Stem Cells from Adult Human Fibroblasts by Defined Factors", Cell 131, Elsevier Inc., (Nov. 30, 2007), 861-872.

Thomson, James A., et al., "Embryonic Stem Cell Lines Derived From Human Blastocysts", Science, 282(5391), (Nov. 6, 1998), 1145-1147.

Walsh, Patrick, et al., "Defined Culture Conditions Accelerate Small-molecule-assisted Neural Induction for the Production of Neural Progenitors from Human-induced Pluripotent Stem Cells", Cell Transplantation, 26(12), (2017), 1890-1902.

Xu, C., et al., "Feeder-Free Growth of Undifferentiated Human Embryonic Stem Cells", Nature Biotechnology, 19(10), (2001), 971-974.

Yao, Shuyuan, et al., "Long-term self-renewal and directed differentiation of human embryonic stem cells in chemically defined conditions", Proc Natl Acad Sci U S A. 103(18), (2006), 6907-6912.

Zeng, Hui, et al., "Specification of region-specific neurons including forebrain glutamatergic neurons from human induced pluripotent stem cells", PLoS One. 5(7):e11853, (2010), 1-11.

Zhang, Su-Chun, et al., "In vitro differentiation of transplantable neural precursors from human embryonic stem cells", Nat Biotechnol. 19(12), (2001), 1129-1133.

"European Application Serial 18732957.8 Response filed Jun. 10, 2020 to Communication pursuant to Rules 161(1) and 162 EPC filed Dec. 17, 2019", 10 pgs.

"International Application Serial No. PCT/US2018/031673, International Preliminary Report on Patentability dated Nov. 21, 2019", 8 pgs.

"Japanese Application Serial No. 2019-561238, Examiners Decision of Final Refusal dated May 31, 2022", w/ English translation, 11 pgs.

"Japanese Application Serial No. 2019-561238, Notification of Reasons for Refusal dated Sep. 1, 2021", (w/ English Translation), 11 pgs.

"Japanese Applicationi Serial No. 2019-561238, Response filed Jan. 31, 2022 to Notification of Reasons for Refusal dated Sep. 1, 2021", w/ English Claims, 21 pgs.

Qi, Yuchen, et al., "Combined small-molecule inhibition accelerates the derivation of functional cortical neurons from human pluripotent stem cells", Nat. Biotechnol., 35(2), (2017), 154-163.

"European Application Serial No. 18732957.8, Communication Pursuant to Article 94(3) EPC dated Aug. 25, 2022", 7 pgs.

"Japanese Application Serial No. 2019-561238, Response filed Sep. 30, 2022 to Examiners Decision of Final Refusal dated May 31, 2022", w/ English Claims, 15 pgs.

"Japanese Application Serial No. 2019-561238, Preliminary Examination Report dated Feb. 7, 2023", w English Translation, 2 pgs.

Gudernova, Iva, "Multikinase activity of fibroblast growth factor receptor (FGFR) inhibitors SU5402, PD173074, AZD1480, AZD4547 and BGJ398 compromises the use of small chemicals targeting FGFR catalytic activity for therapy of short-stature syndromes", Human Molecular Genetics, 2016, vol. 25, No. 1, (2016), 9-23.

\* cited by examiner

THOMSON 1998 — ITSKOVITZ–ELDOR 2000 — ZHANG 2001

- SPONTANEOUS
- TERATOMA
- ROSETTES
- INEFFICIENT
- MONTHS

- SPONTANEOUS
- EMBRYOID BODY
- SERUM
- INEFFICIENT
- 20 DAYS

- DIRECTED
- AGGREGATE
- SFM + FGF2
- EFFICIENT
- 11 DAYS

PERRIER 2004 — YAO 2006 — CHAMBERS 2009

- DIRECTED
- MONOLAYER
- STROMAL SFM
- 90% NEURAL
- 28 DAYS

- DIRECTED
- MONOLAYER
- DEFINED +NOGGIN
- 60 % PAX6
- 8 DAYS

- DIRECTED
- MONOLAYER
- DEFINED +NOGGIN/SB
- 80% PAX6/SOX1
- 11 DAYS

LIPPMANN 2014 — WALSH 2016 — TCHIEU 2017

- SPONTANEOUS
- MONOLAYER
- DEFINED
- 90% PAX6
- 6 DAYS

- DIRECTED
- MONOLAYER
- DEFINED, ERK2I
- 95% SOX1
- <24 HOURS

- DIRECTED
- MONOLAYER
- DEFINED
- DUAL SMAD
- 95% SOX1
- 11 DAYS

FIG. 1

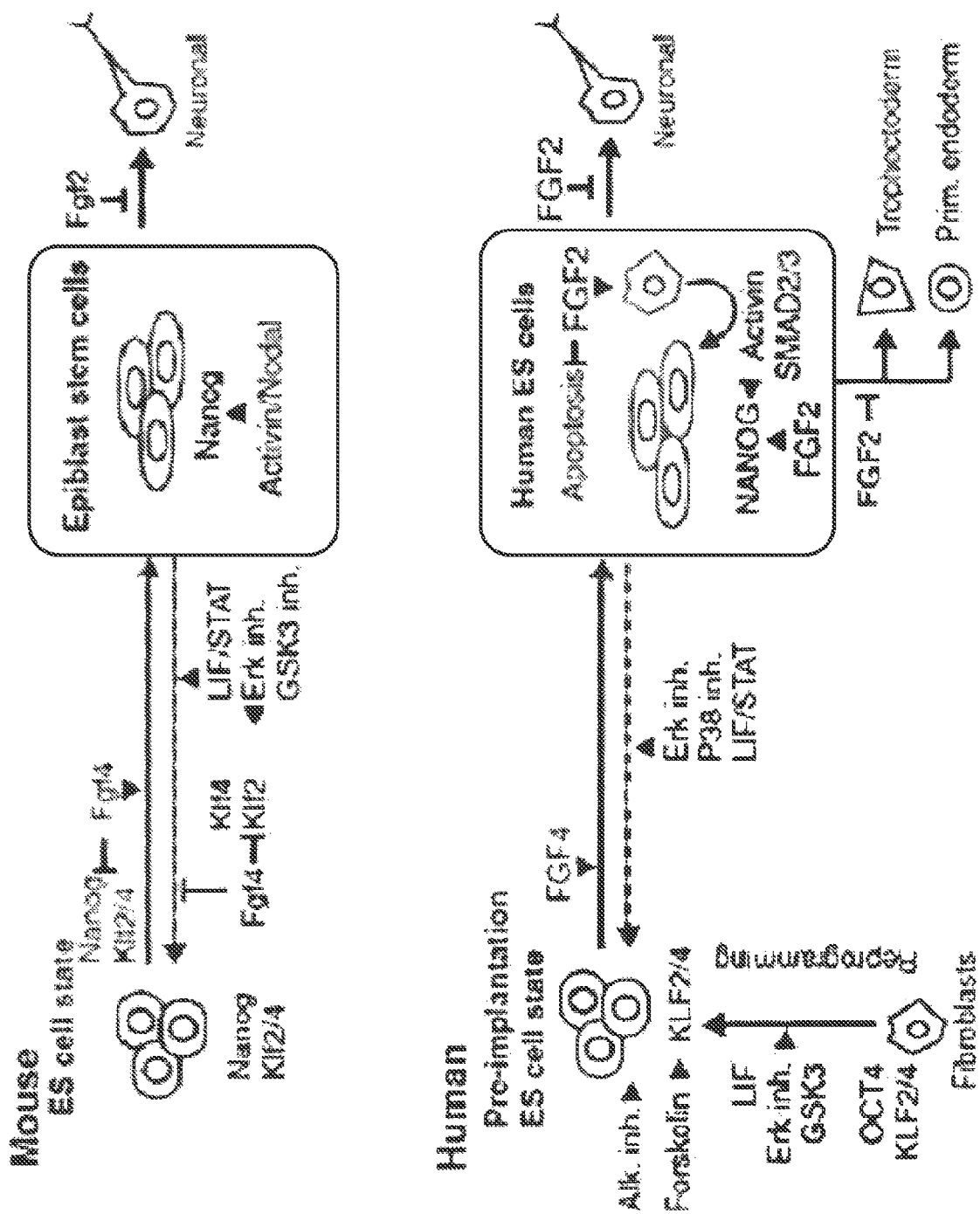

- Directed Differentiation Mindset:
  - Mes/Endoderm Actively Formed
  - If Mes/Endoderm Prevented, Neuroectoderm Passively Formed Mes/Endoderm "Actively Produced"
  hPSCs "Pushed" into Mes/Endoderm NeuroEctoderm "Happens"
  No factors identified to "Push" hPSCs into NE
  "Neural Default Hypothesis"

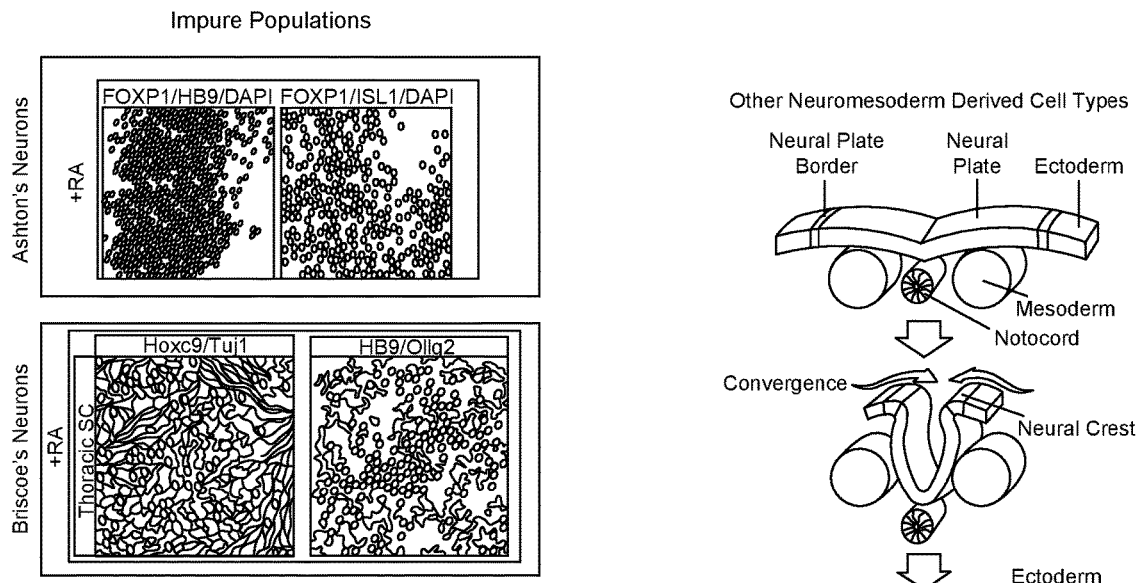
FIG. 15A
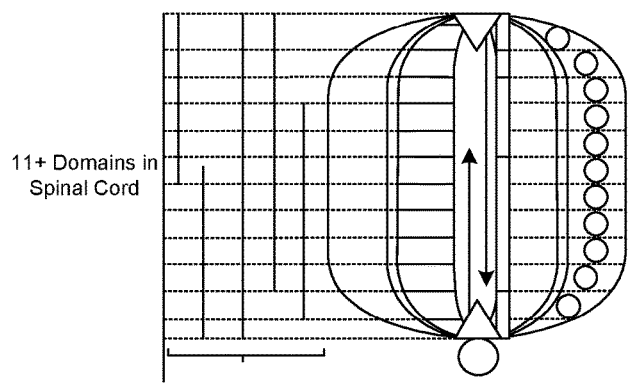
FIG. 15B
FIG. 15C

FIG. 22A-B

| Species | PubChem | Function | Pathway Influenced | Direction |
|---|---|---|---|---|
| Dorsomorphin | pubchem.ncbi.nlm.nih.gov/compound/49761481 | AMPK/ ALK2/3/6 Inhibitor | BMP | down |
| LDN 193189 | pubchem.ncbi.nlm.nih.gov/compound/54613581 | ALK2/3 Inhibitor | BMP | down |
| SU5402 | pubchem.ncbi.nlm.nih.gov/compound/5289418 | FGFR2/VEGFR2 Inhibitor | FGF | down |
| BGJ398 | pubchem.ncbi.nlm.nih.gov/compound/53235510 | FGFR1/2/3/4 Inhibitor | FGF | down |
| XAV939 | pubchem.ncbi.nlm.nih.gov/compound/2726824 | Tankyrase inhibitor | WNT | down |
| Wnt-c59 | pubchem.ncbi.nlm.nih.gov/compound/57519544 | Porcupine Inhibitor | WNT | down |
| IWR1 | pubchem.ncbi.nlm.nih.gov/compound/44483163 | Tankyrase Inhibitor | WNT | down |
| IWP2 | pubchem.ncbi.nlm.nih.gov/compound/2155128 | Porcupine inhibitor | WNT | down |
| IWP4 | pubchem.ncbi.nlm.nih.gov/compound/2155264 | Porcupine inhibitor | WNT | down |
| PD0325901 | pubchem.ncbi.nlm.nih.gov/compound/9826528 | MEK Inhibitor | MEK | down |
| CHIR99021 | pubchem.ncbi.nlm.nih.gov/compound/99956119 | GSK3beta inhibitor | WNT | up |
| BIO | pubchem.ncbi.nlm.nih.gov/compound/5287844 | GSK3beta inhibitor | WNT | up |
| Purmorphamine | pubchem.ncbi.nlm.nih.gov/compound/5284329 | Smoothened Agonist | Hedgehog | up |
| Smoothened Agonist | pubchem.ncbi.nlm.nih.gov/compound/44543753 | Smoothened Agonist | Hedgehog | up |
| DAPT | pubchem.ncbi.nlm.nih.gov/compound/5311272 | Gamma secretase inhibitor | Notch | down |

| Species | Name | Accession | Function | Pathway Influenced | Direction |
|---|---|---|---|---|---|
| | web.stanford.edu/group/nusselab/cgi-bin/wnt/ | | | | |
| WNT1 | Wnt family member 1 | NP_005421.1 | Binds LRP6/Frizzled | WNT | up |
| WNT2 | Wnt family member 2 | NP_003382.1 | Binds LRP6/Frizzled | WNT | up |
| WNT2B/13 | Wnt family member 2B/13 | NP_004176.2 | Binds LRP6/Frizzled | WNT | up |
| WNT3 | Wnt family member 3 | NP_110380.1 | Binds LRP6/Frizzled | WNT | up |
| WNT3A | Wnt family member 3A | NP_149122.1 | Binds LRP6/Frizzled | WNT | up |

FIG. 29A

| | | | | |
|---|---|---|---|---|
| WNT4 | Wnt family member 4 | NP_110388.2 | Binds LRP6/Frizzled | WNT | up |
| WNT5A | Wnt family member 5A | NP_003383.2 | Binds LRP6/Frizzled | WNT | up |
| WNT5B | Wnt family member 5B | NP_116031.1 | Binds LRP6/Frizzled | WNT | up |
| WNT6 | Wnt family member 6 | NP_006513.1 | Binds LRP6/Frizzled | WNT | up |
| WNT7A | Wnt family member 7A | NP_004616.2 | Binds LRP6/Frizzled | WNT | up |
| WNT7B | Wnt family member 7B | NP_478679.1 | Binds LRP6/Frizzled | WNT | up |
| WNT8A | Wnt family member 8A | NP_001287867.1 | Binds LRP6/Frizzled | WNT | up |
| WNT8B | Wnt family member 8B | NP_003384.2 | Binds LRP6/Frizzled | WNT | up |
| WNT9A | Wnt family member 9A | NP_003386.1 | Binds LRP6/Frizzled | WNT | up |
| WNT9B | Wnt family member 9B | NP_003387.1 | Binds LRP6/Frizzled | WNT | up |
| WNT10A | Wnt family member 10A | NP_079492.2 | Binds LRP6/Frizzled | WNT | up |
| WNT10B | Wnt family member 10B | NP_003385.2 | Binds LRP6/Frizzled | WNT | up |
| WNT11 | Wnt family member 11 | NP_004617.2 | Binds LRP6/Frizzled | WNT | up |
| WNT16 | Wnt family member 16 | NP_476509.1 | Binds LRP6/Frizzled | WNT | up |
| DKK1 | dickkopf WNT signaling pathway inhibitor 1 | NP_036374.1 | Binds LRP6/Frizzled | WNT | down |
| DKK2 | dickkopf WNT signaling pathway inhibitor 2 | NP_055236.1 | Binds LRP6/Frizzled | WNT | down |
| DKK3 | dickkopf WNT signaling pathway inhibitor 3 | NP_056965.3 | Binds LRP6/Frizzled | WNT | down |
| DKK4 | dickkopf WNT signaling pathway inhibitor 4 | NP_055235.1 | Binds LRP6/Frizzled | WNT | down |
| Noggin | Noggin | NP_005441.1 | Binds BMPR1/2 | BMP | down |
| Sonic Hedgehog | Sonic Hedgehog | NP_000184.1 | Binds Smoothened | Hedgehog | up |
| BMP1 | bone morphogenic protein 1 | NP_001190.1 | Binds BMPR1/2 | BMP | up |
| BMP2 | bone morphogenic protein 2 | NP_001191.1 | Binds BMPR1/2 | BMP | up |
| BMP3 | bone morphogenic protein 3 | NP_001192.3 | Binds BMPR1/2 | BMP | up |
| BMP4 | bone morphogenic protein 4 | NP_001334841.1 | Binds BMPR1/2 | BMP | up |
| BMP5 | bone morphogenic protein 5 | NP_066551.1 | Binds BMPR1/2 | BMP | up |
| BMP6 | bone morphogenic protein 6 | NP_001709.1 | Binds BMPR1/2 | BMP | up |
| BMP7 | bone morphogenic protein 7 | NP_001710.1 | Binds BMPR1/2 | BMP | up |
| BMP8a | bone morphogenic protein 8a | NP_861525.2 | Binds BMPR1/2 | BMP | up |
| BMP8b | bone morphogenic protein 8b | NP_001711.2 | Binds BMPR1/2 | BMP | up |
| BMP10 | bone morphogenic protein 10 | NP_055297.1 | Binds BMPR1/2 | BMP | up |

FIG. 29B

| | | | | | |
|---|---|---|---|---|---|
| BMP11 | bone morphogenic protein 11 | NP_005802.1 | Binds BMPR1/2 | BMP | up |
| BMP15 | bone morphogenic protein 15 | NP_005439.2 | Binds BMPR1/2 | BMP | up |
| GDNF | glial cell line-derived neurotrophic factor ncbi.nlm.nih.gov/pubmed/22367796 | NP_000505.1 | Binds RET | MEK/ERK | up |
| BDNF | brain-derived neurotrophic factor | NP_733931.1 | Binds TRK | MEK/ERK | up |
| LEFTY2 | left-right determination factor 2 | NP_003231 | Binds TGFBR | SMAD | down |
| NGF | beta-nerve growth factor | NP_002497.2 | Binds p75NTR/Trk | MEK/ERK | up |
| NT3 | neurotrophin-3 | NP_001096124 | Binds p75NTR/Trk | MEK/ERK | up |
| NT4 | neurotrophin-4 | NP_006170.1 | Binds p75NTR/Trk | MEK/ERK | up |
| TGF beta 1 | transforming growth factor beta-1 preproprotein | NP_000651.3 | Binds TGFBR | SMAD | up |
| TGF beta 2 | transforming growth factor beta-2 preproprotein | NP_001129071 | Binds TGFBR | SMAD | up |
| TGF beta 3 | transforming growth factor beta-3 preproprotein | NP_003230 | Binds TGFBR | SMAD | up |
| FGF1 | Fibroblast growth factor 1 | NP_000791.1 | Binds FGFR1/2/3/4 | MEK/ERK/PI3K | up |
| FGF2 | Fibroblast growth factor 2 | NP_001997.5 | Binds FGFR1/2/3/4 | MEK/ERK/PI3K | up |
| FGF3 | Fibroblast growth factor 3 | NP_005238.1 | Binds FGFR1/2/3/4 | MEK/ERK/PI3K | up |
| FGF4 | Fibroblast growth factor 4 | NP_001998.1 | Binds FGFR1/2/3/4 | MEK/ERK/PI3K | up |
| FGF5 | Fibroblast growth factor 5 | NP_004455.2 | Binds FGFR1/2/3/4 | MEK/ERK/PI3K | up |
| FGF6 | Fibroblast growth factor 6 | NP_066276.2 | Binds FGFR1/2/3/4 | MEK/ERK/PI3K | up |
| FGF7 | Fibroblast growth factor 7 | NP_002000.1 | Binds FGFR1/2/3/4 | MEK/ERK/PI3K | up |
| FGF8 | Fibroblast growth factor 8 | NP_006110.1 | Binds FGFR1/2/3/4 | MEK/ERK/PI3K | up |
| FGF9 | Fibroblast growth factor 9 | NP_002001.1 | Binds FGFR1/2/3/4 | MEK/ERK/PI3K | up |

FIG. 29C

| | | | |
|---|---|---|---|
| FGF10 | Fibroblast growth factor 10 | NP_004456.1 | Binds FGFR1/2/3/4 MEK/ERK/PI3 K | up |
| FGF11 | Fibroblast growth factor 11 | NP_004103.1 | Binds FGFR1/2/3/4 MEK/ERK/PI3 K | up |
| FGF12 | Fibroblast growth factor 12 | NP_066360.1 | Binds FGFR1/2/3/4 MEK/ERK/PI3 K | up |
| FGF13 | Fibroblast growth factor 13 | NP_004105.1 | Binds FGFR1/2/3/4 MEK/ERK/PI3 K | up |
| FGF14 | Fibroblast growth factor 14 | NP_004106.1 | Binds FGFR1/2/3/4 MEK/ERK/PI3 K | up |
| FGF15 | Fibroblast growth factor 15 | NP_032029.1 | Binds FGFR1/2/3/4 MEK/ERK/PI3 K | up |
| FGF16 | Fibroblast growth factor 16 | NP_003859.1 | Binds FGFR1/2/3/4 MEK/ERK/PI3 K | up |
| FGF17 | Fibroblast growth factor 17 | NP_003858.1 | Binds FGFR1/2/3/4 MEK/ERK/PI3 K | up |
| FGF18 | Fibroblast growth factor 18 | NP_003853.1 | Binds FGFR1/2/3/4 MEK/ERK/PI3 K | up |
| FGF19 | Fibroblast growth factor 19 | NP_005108.1 | Binds FGFR1/2/3/4 MEK/ERK/PI3 K | up |
| FGF20 | Fibroblast growth factor 20 | NP_062825.1 | Binds FGFR1/2/3/4 MEK/ERK/PI3 K | up |
| FGF21 | Fibroblast growth factor 21 | NP_061986.1 | Binds FGFR1/2/3/4 MEK/ERK/PI3 K | up |
| FGF22 | Fibroblast growth factor 22 | NP_065686.1 | Binds FGFR1/2/3/4 MEK/ERK/PI3 K | up |
| FGF23 | Fibroblast growth factor 23 | NP_065689.1 | Binds FGFR1/2/3/4 MEK/ERK/PI3 K | up |
| Beta-iii Tubulin | tubulin beta-3 chain | NP_006077 | | |
| Tyrosine Hydroxylase | tyrosine 3-monooxygenase isoform a | NP_954986.2 | | |
| PRPH | peripherin | NP_006253.2 | | |

FIG. 29D

| | | |
|---|---|---|
| Brachyury | brachyury protein | NP_003172 |
| BRN3A | POU domain, class 4, transcription factor 1 | NP_006228 |
| FOXA2 | hepatocyte nuclear factor 3 beta | NP_068556.2 |
| FOXG1 | forkhead box protein G1 | NP_005240 |
| GBX2 | homeobox protein GBX-2 | NP_001476.2 |
| GFAP | glial fibrillary acidic protein | NP_002046.1 |
| HOXB1 | homeobox protein Hox-B1 | NP_002135.2 |
| HOXB4 | homeobox protein Hox-B4 | NP_076920.1 |
| HOXC5 | homeobox protein Hox-C5 | NP_061826.1 |
| HOXC8 | homeobox protein Hox-C8 | NP_073149.1 |
| LMX1A | LIM homeobox transcription factor 1-alpha | NP_001167540.1 |
| Myogenin | myogenin | NP_002470.2 |
| NANOG | homeobox protein NANOG | NP_079141.2 |
| RBFOX3 | RNA binding protein fox-1 homolog 3 | NP_001076044.1 |
| NKX2.2 | homeobox protein Nkx-2.2 | NP_002500.1 |
| NURR1 | nuclear receptor subfamily 4 group A member 2 | NP_006177.1 |
| OLIG2 | oligodendrocyte transcription factor 2 | NP_005797.1 |
| OTX2 | homeobox protein OTX2 | NP_001257454.1 |
| PAX3 | paired box protein Pax-3 | NP_852122.1 |
| PAX5 | paired box protein Pax-5 | NP_057953.1 |
| PAX6 | paired box protein Pax-6 | NP_001245394.1 |
| PITX3 | pituitary homeobox 3 | NP_005020 |
| SIX3 | homeobox protein SIX3 | NP_005404.1 |
| SOX1 | transcription factor SOX-1 | NP_005977.2 |
| SOX10 | transcription factor SOX-10 | NP_008872.1 |
| SOX2 | transcription factor SOX-2 | NP_003097.1 |
| SOX9 | transcription factor SOX-9 | NP_000337.1 |
| TBX6 | T-box transcription factor TBX6 | NP_004599.2 |

FIG. 29E

ACCELERATION OF STEM CELL DIFFERENTIATION

PRIORITY

This application is a U.S. National Stage Application under 35 U.S.C. 371 from International Application No. PCT/US2018/031673, filed May 8, 2018, published as WO 2018/208836, which claims the benefit of priority from U.S. Provisional Patent Application Ser. No. 62/503,088, filed on May 8, 2017, which are herein incorporated in its entirety by reference.

BACKGROUND

Differentiation of human pluripotent stem cells proceeds stage-specifically to generate progressively more mature developmentally analogous embryonic structures in vitro. The first stage in generating the ectodermal germ layer in vitro has proceeded no faster than 6 days since the field's inception in 1998. As such, creating any ectoderm-derived cell type requires at least a minimum of 6 days to derive the ectoderm germ layer, followed by additional time for developmentally later events to transpire.

The positional character of this ectoderm germ layer is generally regarded as anterior, capable of forming cells/tissues of the head and neck. However, recent data points to a population of cells called neuromesoderm, which is a posterior ectoderm germ layer as well as the posterior mesoderm germ layer. Currently, the formation of the anterior ectodermal germ layer and posterior neuromesodermal germ layer from human pluripotent stem cells arises in vitro utilizing disparate culture conditions within different time frames.

SUMMARY

Derivation and differentiation of human-induced pluripotent stem cells (hiPSCs) (Takahashi K, et al. 2007. Cell. 131(5):861-872; Yu J, et al. 2007. Science. 318(5858): 1917-1920) provide the opportunity to study otherwise inaccessible developmentally transient progenitor cells useful for understanding of human embryogenesis, and is also a tool for therapeutic intervention in cases of injury or disease. Evidence suggests that iPSC-derived progenitors function similarly to their fetal-derived counterparts (Lindvall O, Bjorklund A. 2011. Neurotherapeutics. 8(4): 539-548; Bjorklund A, Lindvall O. 2017. J Parkinson's Dis. 7(s1):S23-S33) and possess the ability to engraft and survive in a human host, making it perhaps possible to alleviate various pathological conditions caused by cell loss or dysfunction. Terminal maturation of iPSC-derived progenitors in vitro can also support chemical screening for identification of novel therapeutic drugs. These efforts are especially important for conditions of the central nervous system where tissue acquisition from living patients is problematic.

Provide herein are compositions, methods and kits to accelerate pluripotent stem cell (e.g., human stem cells) differentiation through inhibition of, for example, ERK signaling.

One embodiment provides a method for inducing differentiation in stem cells, comprising, a) providing: i) a cell culture comprising pluripotent stem cells, ii) an inhibitor of Activin receptor-Like Kinase (ALK) 2/3 signaling, wherein said inhibitor is selected from the group consisting of Noggin, Dorsomorphin, LDN-193189, compounds with similar inhibitory function and mixtures thereof, and iii) an inhibitor of fibroblast growth factor (FGF) signaling, wherein said inhibitor is selected from the group consisting SU5402, BGJ398, antibodies to FGF protein family members (e.g., Anti-FGF-2/basic FGF (neutralizing) Antibody, clone bFM-1 MilliporeSigma cat #05-117) or their receptors, compounds with similar inhibitory function and mixtures thereof, or iv) in place of or in combination with an inhibitor of FGF signaling, an inhibitor of Extracellular-Regulated Kinase (ERK) signaling, wherein said inhibitor is selected from the group consisting PD0325901 or compounds with similar inhibitory function and mixtures thereof; b) exposing said pluripotent stem cells of i) simultaneously to culture medium containing inhibitors of ALK 2/3 of ii) and inhibitors of FGF of iii), and/or inhibitors of ERK signaling of iv); and c) inducing differentiation of said contacted pluripotent stem cells so as to generate a population of cultured anterior ectoderm cells.

In one embodiment, said anterior ectoderm comprises at least 10% up to 100% of said population of differentiated cells. For example, said anterior ectoderm comprises at least 10%, at least 20%, at least 30%, at least 40%, at least 50%, at least 60%, at least 70%, at least 80%, or at least 90%.

In one embodiment, said primitive ectoderm arises within 24 hours of exposure to said inhibitors.

In one embodiment, said pluripotent stem cells are selected from the group consisting of embryonic stem cells (ESC), somatic stem cells, and induced pluripotent stem cells (iPSC). In one embodiment, the stem cells are human stem cells.

In one embodiment, said population of anterior ectoderm cells is further differentiated into cells selected from the group consisting of central nervous system (CNS) progenitor cells, patternable progenitor cells, neurons and glia; and derivatives of the epidermis, neural crest and neuromesoderm, including epidermal stem cells, keratinocytes, melanocytes, peripheral neurons, schwann cells, mesenchymal stromal cells, osteoblasts, chondrocytes, adipocytes, fibroblasts, and myoblasts.

In another embodiment, the ectoderm is isolated.

One embodiment provides a kit comprising one or more inhibitors of ALK 2/3 signaling, one or more inhibitors of ERK signaling, one or more inhibitors of MAPK/ERK Kinase (MEK) 1/2, one or more inhibitors of Fibroblast Growth Factors (FGF) 1, 2, 3 and/or 4, one or more inhibitors of WNT, and/or one or more activators of WNT (for example, ALK2/3 inhibitor can be LDN193189, FGF inhibitor can be BGJ398, MEK inhibitor can be PD, WNT activator can be CHIR99021 or BIO). In one embodiment, the kit comprises pluripotent stem cells. In one embodiment, the pluripotent stem cells are selected from the group consisting of embryonic stem cells (ESC), somatic stem cells, and induced pluripotent stem cells (iPSC). In one embodiment, the pluripotent stem cells are human.

One embodiment provides a method for patterning said ectoderm into telencephalic neuroepithelium expressing PAX6/FOXG1/SIX3/OTX2 comprising contacting said ectoderm with an inhibitor of WNT signaling, said inhibitor of WNT signaling is selected from the group consisting of DKK1 protein, or chemical analogues of DKK1 including XAV939 or WntC59, or molecules that function similarly to inhibit WNT signaling.

One embodiment provides a method for patterning said ectoderm into ventral telencephalic neuroepithelium expressing PAX6/FOXG1/SIX3/OTX2 and NKX2.1 and/or NKX2.2 comprising contacting said ectoderm with an inhibitor of WNT signaling, said inhibitor selected from the group consisting of DKK1 protein or chemical analogues of DKK1, including XAV939 or WntC59, or molecules that function similarly to inhibit WNT signaling; and/or an activator of sonic hedgehog pathway, said activator selected from the group consisting of members of the hedgehog protein family, including such as sonic hedgehog, post-translationally modified sonic hedgehog proteins, or chemical analogues to sonic hedgehog that stimulate the sonic hedgehog pathway, including purmorphamine, smoothened agonist, and similar chemical analogues.

One embodiment provides a method for patterning said ectoderm into diencephalic neuroepithelium expressing PAX6/OTX2 comprising contacting said ectoderm with at least one activator of WNT signaling, said activator selected from the group consisting of Wnt proteins or chemical analogues to WNT that stimulate WNT pathways, including BIO, CHIR, and compounds with similar activity.

One embodiment provides a method for patterning said ectoderm into mesencephalic neuroepithelium that does not express PAX6, but does express OTX2 and/or PAX5 comprising contacting said ectoderm with at least one activator of WNT signaling, said activator selected from the group consisting of WNT proteins or chemical analogues to WNT that stimulate WNT pathways, including BIO, CHIR, and compounds with similar activity. In one embodiment, the method further comprises contacting said ectoderm with an activator of fibroblast growth factor receptor family selected from members of the FGF protein family, including FGF1, FGF2, FGF8b, and thermostable variants of FGF1 and FGF2. In one embodiment, the method further comprises contacting said ectoderm with an activator of sonic hedgehog pathway selected from members of the hedgehog protein family, including sonic hedgehog, post-translationally modified sonic hedgehog proteins, or chemical analogues to sonic hedgehog that stimulate the sonic hedgehog pathway, including purmorphamine, smoothened agonist, and similar chemical analogues. In one embodiment, the mesencephalic conversion occurs within 24 hours to about 48 hours via downregulation of PAX6, maintenance of OTX2, and upregulation of PAX5 with 1-100% efficiency, including about 10%, about 20%, about 30%, about 40%, about 50%, about 60%, about 70%, about 80%, and about 90% efficiency.

One embodiment provides a method for patterning said mesencephalic neuroepithelium formed as described herein into mesencephalic floorplate expressing OTX2/PAX5/FOXA2 and LMX1A comprising contacting said mesencephalic neuroepithelium with an activator of the sonic hedgehog pathway, including members of the hedgehog protein family, including sonic hedgehog protein, post-translationally modified sonic hedgehog proteins, or chemical analogues to sonic hedgehog that stimulate the sonic hedgehog pathway, including purmorphamine, smoothened agonist, and similar chemical analogues, so as to yield mesencephalic floorplate expressing OTX2/PAX5/FOXA2 and LMX1A. In one embodiment, the method further comprises contacting said mesencephalic neuroepithelium with an inhibitor of a fibroblast growth factor family and/or downstream MEK/ERK signaling including one or more of VEGFR2/FGFR2 inhibitor SU5402 (CaymanChem cat #13182), FGFR 1/2/3/4 inhibitor BGJ398 (CaymanChem cat #19157), MEK inhibitor PD0325901 (CaymanChem cat #13034). In one embodiment, the method further comprises contacting said mesencephalic neuroepithelium with an inhibitor to WNT signaling, wherein the inhibitor is LRP6/Frizzled antagonist DKK1 protein or chemical analogues of DKK1 (Peprotech cat #120-30), including tankyrase inhibitor XAV939 (CaymanChem cat #13596) or porcupine inhibitor WntC59 (CaymanChem cat #16644) or molecules that function similarly. In one embodiment, the method further comprises contacting said mesencephalic neuroepithelium with an inhibitor of SMAD signaling, said inhibitor including activin-like kinase (ALK) receptor 2/3 inhibitor LDN193189 (CaymanChem cat #19396) or activin-like kinase (ALK) receptor 4/5/7 inhibitor A8301 (CaymanChem cat #9001799). In embodiment, the mesencephalic neuroepithelium conversion occurs within 24 to 48 hours and occurs with 1-100% efficiency, including about 10%, about 20%, about 30%, about 40%, about 50%, about 60%, about 70%, about 80%, and about 90% efficiency.

One embodiment provides a method for differentiating the mesencephalic neuroepithelium into immature neurons expressing Nurr1, beta iii tubulin, tyrosine hydroxylase. In one embodiment, the method comprises contacting said mesencephalic neuroepithelium with one or more inhibitors of the notch pathway, including DAPT and chemicals with similar notch-inhibitory function, such as gamma secretase inhibitors and presenilin inhibitors.

In one embodiment, the method further comprises contacting said mesencephalic neuroepithelium with neuronal pro-survival factors BDNF, GDNF, NT3, NT4 or a combination thereof. In one embodiment, the method further comprises contacting said mesencephalic neuroepithelium with one or more activators of SMAD signaling, including TGFB superfamily ligands Activin A, TGFB1, TGFB3 or a combination thereof.

One embodiment provides a method for differentiating said mesencephalic neuroepithelium into cranial neural crest stem cells expressing PAX3/SOX10/SOX9/OTX2 or PAX3/SOX10/SOX9/OTX2/PAX5 comprising contacting said mesencephalic neuroepithlium with an activator of the bone morphogenic protein pathway, including bone morphogenic protein 4 (BMP4), and/or other proteins of the BMP family such as BMP2. In one embodiment, the method further comprises contacting said mesencephalic neuroepithelium with an inhibitor of FGF signaling, said FGF inhibitor comprising SU5402, BGJ398 or other factors with similar inhibitory function, and/or an inhibitor of MEK/ERK, said MEJK/ERK inhibitor comprising PD0325901. In one embodiment, neural crest stem cell conversion occurs within 24 to 48 hours with 1-100% efficiency, including about 10%, about 20%, about 30%, about 40%, about 50%, about 60%, about 70%, about 80%, and about 90% efficiency.

One embodiment provides a method to induce differentiation in stem cells, comprising, a) providing: i) a cell culture comprising pluripotent stem cells, ii) an inhibitor of Activin receptor-Like Kinase (ALK) 2/3 signaling, wherein said inhibitor is selected from the group consisting of Noggin, Dorsomorphin, LDN-193189, compounds with similar inhibitory function and mixtures thereof, and iii) an inhibitor of fibroblast growth factor (FGF) signaling, wherein said inhibitor is selected from the group consisting of SU5402, BGJ398, compounds with similar inhibitory function and mixtures thereof, or iv) in place of or in combination with an inhibitor of FGF signaling, an inhibitor of Extracellular-Regulated Kinase (ERK) signaling, wherein said inhibitor is selected from the group consisting PD0325901 or compounds with similar inhibitory function and mixtures thereof; v) an activator of WNT signaling, wherein the activator is selected from the group consisting of BIO, CHIR99021, compounds with similar activating function and mixtures thereof, b) exposing said pluripotent stem cells of i) simultaneously to culture medium containing inhibitors of ALK 2/3 of ii) and inhibitors of FGF of iii), and/or inhibitors of ERK signaling of iv); and activators of WNT signaling of v); and c) inducing differentiation of said pluripotent stem cells of b) into a population of cultured rostral hindbrain neuromesoderm expressing SOX2/Brachyury/GBX2/HOXB1. In one embodiment, said rostral hindbrain neuromesoderm comprise at least 10% up to 100% of said population of cells. For example, said anterior ectoderm comprises at least 10%, at least 20%, at least 30%, at least 40%, at least 50%, at least 60%, at least 70%, at least 80%, or at least 90%. In one embodiment, said rostral hindbrain neuromesoderm arises within 24 hours of exposure to said inhibitors. In one embodiment, said pluripotent stem cells are selected from the group consisting of embryonic stem cells (ESC), somatic stem cells, and induced pluripotent stem cells (iPSC). In one embodiment, the stem cells are human stem cells. In one embodiment, said population of rostral hindbrain neuromesoderm further differentiates into cells selected from the group consisting of central and peripheral nervous system progenitor cells, patternable progenitor cells, neurons, glia, and/or derivatives of the epidermis and neural crest, including mesenchymal stromal cells and their derivatives such as osteocytes, chondrocytes, adipocytes, and derivatives of somite tissue, including mesenchymal stromal cells, osteocytes, chondrocytes, adipocytes, and myogenic precursors.

In one embodiment, the method further comprises converting said rostral hindbrain neuromesoderm into hindbrain neuroepithelium expressing SOX1/GBX2/HOXB1 comprising contacting said rostral hindbrain neuromesoderm with an inhibitor of fibroblast growth factor (FGF) signaling, wherein said inhibitor is selected from the group consisting SU5402, BGJ398, antibodies to FGF protein family members or their receptors, chemicals with similar inhibitory function and mixtures thereof. In one embodiment, said conversion will occur within 24 hours with 1-100% efficiency, including about 10%, about 20%, about 30%, about 40%, about 50%, about 60%, about 70%, about 80%, and about 90% efficiency.

In one embodiment, the method further comprises converting said rostral hindbrain neuromesoderm into cranial neural crest stem cells expressing PAX3/SOX10/SOX9/HOXB1 comprising contacting said rostral hindbrain neuromesoderm with an activator of bone morphogenic protein pathway, wherein the activator of bone morphogenic protein pathway is selected from bone morphogenic protein 4 (BMP4), and other proteins of the BMP family such as BMP2. One embedment provides contacting said rostral hindbrain neuromesoderm with an inhibitor of FGF signaling, said inhibitor of FGF signaling comprises SU5402, BGJ398 or other factors with similar inhibitory function, and/or contacting said rostral hindbrain neuromesoderm with an inhibitor to MEK/ERK, said inhibitor to MEK/ERK comprises PD0325901. In one embodiment, the neural crest stem cell conversion occurs within 24 to 48 hours with 1-100% efficiency, including about 10%, about 20%, about 30%, about 40%, about 50%, about 60%, about 70%, about 80%, and about 90% efficiency.

In one embodiment, the method further comprises converting said hindbrain neuroepithelium expressing SOX1/GBX2/HOXB1 into cranial neural crest stein cells expressing PAX3/SOX10/SOX9/HOXB1 comprising contacting said hindbrain neuroepithelium expressing SOX1/GBX2/HOXB1 with an activator of bone morphogenic protein pathway, wherein an activator of bone morphogenic protein pathway comprises bone morphogenic protein 4 (BMP4), and other proteins of the BMP family such as BMP2. One embodiment comprises further contacting said hindbrain neuroepithelium expressing SOX1/GBX2/HOXB1 with an inhibitor of FGF signaling, wherein said inhibitor of FGF signaling compromises SU5402, BGJ398 or other factors with similar inhibitory function, and/or contacting said hindbrain neuroepithelium expressing SOX1/GBX2/HOXB1 with an inhibitor of MEK/ERK, wherein said inhibitor of MEK/ERK comprises PD0325901. In one embodiment, wherein said neural crest stem cell conversion occurs within 24 to 48 hours with 1-100% efficiency, including about 10%, about 20%, about 30%, about 40%, about 50%, about 60%, about 70%, about 80%, and about 90% efficiency.

In one embodiment, the method further comprises converting said rostral hindbrain neuromesoderm into caudalized neuromesoderm comprising contacting said rostral hindbrain neuromesoderm with an activator of WNT signaling, wherein said activator comprises WNT, proteins or chemical analogues to WNT that stimulate WNT pathways, including BIO, CHIR, and compounds with similar activity, wherein the activator of WNT signaling contacts said rostral hindbrain neuromesoderm either alone or in combination with an activator of fibroblast growth factor receptor family, wherein said activator of the fibroblast growth factor receptor family comprises members of the fibroblast growth factor protein family such as fibroblast growth factor 1 (FGF1), fibroblast growth factor 2 (FGF2), fibroblast growth factor 8b (FGF8b) or thermostable variants of FGF1 and/or FGF2. In one embodiment, said rostral hindbrain neuromesoderm can be converted into caudal hindbrain neuromesoderm expressing SOX2/Brachyury/HOXB4 within 24 hours with 1-100% efficiency, including about 10%, about 20%, about 30%, about 40%, about 50%, about 60%, about 70%, about 80%, and about 90% efficiency.

In another embodiment, the caudal hindbrain neuromesoderm can be converted into cervical spinal neuromesoderm using CHIR99021 and FGF to express SOX2/T/HOXB4/HOXC5 within 24 hours with 1-100% efficiency, including about 10%, about 20%, about 30%, about 40%, about 50%, about 60%, about 70%, about 80%, and about 90% efficiency. In one embodiment, cervical spinal neuromesoderm can be converted into somite tissue by sustained WNT pathway activation in the absence of added FGF signaling. In one embodiment, cervical-level somite tissue is created within 24-48 hours with 1-100% efficiency, including about 10%, about 20%, about 30%, about 40%, about 50%, about 60%, about 70%, about 80%, and about 90% efficiency.

In one embodiment, the method further comprises converting said caudal hindbrain neuromesoderm into cervical spinal trunk neural crest stem cells expressing PAX3/SOX10/SOX9 comprising contacting said caudal hindbrain neuromesoderm with an activator of SMA mothers against decapentaplegic (SMAD) signaling, wherein said activator of SAMD signaling comprises BMP2 and/or BMP4. One embodiment further comprises contacting said a cervial spinal neuromesoderm with an inhibitor of FGF and/or MEK/ERK signaling, wherein said inhibitor of FGF and/or MEK/ERK signaling comprises blocking antibodies to FGF ligands or receptors and/or chemical inhibitors BGJ398, SU5402, PD0325901, or agents with similar functions (including, for example, PD 173074, SU 6668, PD 166285 dihydrochloride, FIIN 1 hydrochloride, PD 161570, AP 24534; rndsystetms.com/search?common_name=FGF%20Receptor%20Inhibitors). In one embodiment, said conversion occurs within 24 to 48 hours with 1-100% efficiency, including about 10%, about 20%, about 30%, about 40%, about 50%, about 60%, about 70%, about 80%, and about 90% efficiency.

The present invention provides methods to produce human primitive ectoderm, such as anterior ectoderm and/or posterior neuromesoderm by (i) obtaining stem cells (e.g., hPSCs) (grown in defined, feeder free conditions (e.g., Essential 8 Medium on recombinant human vitronectin, laminin, or fibronectin)), and (ii) culturing the stem cell during low-density colony passage (40-80 thousand cells per square centimeter) under conditions that block Activin receptor-Like Kinase (ALK) 2/3 and/or Extracellular signal-Regulated Kinase (ERK) signaling, with germ-layer specific modulation of the WNT pathway. In one embodiment, the methods for culture include defined conditions. In another embodiment, a defined system refers to the use of a recombinant protein or chemically synthesized matrix. In one embodiment, a defined system refers to the use of a media composition comprising recombinant proteins and synthesized chemicals. In one embodiment, the stem cells are cultured in a monolayer. Another embodiment contemplates the use of media that is supplemented with compounds LDN193189 and BGJ398, PD0325901 and/or CHIR99021

One embodiment provides a kit comprising a first inhibitor of ALK 2/3 signaling, a second inhibitor of ERK signaling and an activator of WNT signaling. In one embodiment, said first inhibitor is selected from the group consisting of a disulfide-linked homodimer of Noggin, Dorsomorphin, LDN 193189, or a combination or mixture thereof. In one embodiment, said Noggin is selected from mouse, human, rat, and/or xenopus Noggin. In one embodiment, said second inhibitor inhibits an ERK pathway. In one embodiment, said second inhibitor inhibits a signaling pathway and is selected from the group consisting of Fibroblast Growth Factor (FGF) 1, 2, 3, and/or 4. In one embodiment, said second inhibitor is selected from the group consisting of SU5402, BGJ398 and/or derivatives thereof. In one embodiment, said second inhibitor inhibits MAPK/ERK Kinase (MEK) 1/2. In one embodiment, said second inhibitor is PD0325901 and/or derivatives thereof. In one embodiment, the activator of WNT signaling is selected form the group consisting of GSK3b inhibitors, CHIR99021, BIO (6-bromoindirubin-3'-oxime, WNT pathway activator), or WNT ligands (e.g., Wnt1, Wnt2, Wnt3). In one embodiment, said kit further comprises a stem cell, such as a human stem cell. In one embodiment, the kit further comprises instructions.

One embodiment provides a method for inducing differentiation in a stem cell, comprising, a) providing: i) a cell culture comprising stem cells, ii) a first inhibitor of ALK 2/3 signaling, iii) a second inhibitor of inhibitor of ERK signaling, iv) an activator of WNT signaling, and b) contacting said stem cells with said first inhibitor of ALK 2/3 signaling and said second inhibitor of ERK signaling under conditions for inducing an undifferentiated stem cell into differentiated cell (and optionally said activator of WNT signaling). In one embodiment, said first inhibitor is selected from the group consisting of a disulfide-linked homodimer of Noggin, Dorsomorphin, LDN-193189, combination thereof and mixture thereof. In one embodiment, said is Noggin is selected from mouse, human, rat, and/or xenopus Noggin. In one embodiment, said second inhibitor is an inhibitor of ERK signaling. In one embodiment, said second inhibitor is BGJ398 and/or derivatives thereof. In one embodiment, said second inhibitor is PD0325901 and/or derivatives thereof. In one embodiment, said activator stimulates WNT signaling. In another embodiment, said activator is CHIR99021 and/or derivatives thereof. In one embodiment, said differentiated cell is a primitive ectoderm cell or germ layer cell. In one embodiment, said differentiated cell is a part of a population of cultured cells. In one embodiment, said differentiated cell is at least 10% up to 100% of said population of cultured cells. In one embodiment, said differentiated cell in a population of cultured cells expresses Sex-determining region Y, box 1 (SOX1; accession NP_005977; incorporated by reference) protein, and/or Paired Box Six (PAX6; accession NP_000271; incorporated herein by reference) protein (SOX1 and Pax6 are intracellular antigens which makes isolation through standard methodologies impractical). In one embodiment, said SOX1 and/or PAX6 is expressed within 24 hours of induction. In one embodiment, said SOX1 and/or PAX6 protein is expressed in at least 10% of said population of cultured cells. In one embodiment, said differentiated cell is a neuromesoderm germ layer cell. In one embodiment, said differentiated cell is a part of a population of cultured cells. In one embodiment, said differentiated cell is at least 10% up to 100% of said population of cultured cells. In one embodiment, said differentiated cells in a population of cultured cells expresses Sex-determining region Y, box 2 (SOX2; accession NP_003172.1; incorporated by reference) protein, and/or Brachyury (T: accession NP_003172.1, incorporated by reference) protein (SOX2 and T are intracellular antigens which makes isolation through standard methodologies impractical). In one embodiment, said SOX2 and T is expressed within 24 hours of induction. In one embodiment, said SOX2 and T protein are expressed in at least about 10% of said population of cultured cells. In one embodiment, said stem cell is selected from the group consisting of embryonic stem cells, including human embryonic stem cells (hESC), somatic stem cells (e.g., human), and induced pluripotent stein cells (iPSC, such as human iPSC). In one embodiment, said non-default differentiated cell is of ectodermal lineage.

One embodiment provides a method for inducing differentiation in stem cells, comprising, a) providing: i) a cell culture comprising stem cells (such as human stem cells) ii) a first inhibitor of ALK 23 signaling, iii) a second inhibitor of inhibitor of ERK signaling, iv) a third inhibitor of ALK 4/5/7 signaling, and b) contacting said stem cells with said inhibitors of ALK 2/3/4/5/7 and ERK signaling under conditions for inducing an undifferentiated stem cell into a differentiated cell. In one embodiment, said first inhibitor is selected from the group consisting of a disulfide-linked homodimer of Noggin, Dorsomorphin, LDN-193189, combination thereof and mixture thereof. In one embodiment, said is Noggin is selected from mouse, human, rat, and xenopus Noggin. In one embodiment, said second inhibitor is BGJ398 and derivatives thereof. In one embodiment, said second inhibitor is PD0325901 and derivatives thereof. In one embodiment, said third inhibitor is inhibitor of ALK 4/5/7 signaling. In one embodiment, said third inhibitor is selected from the group consisting of A8301, SB431542 and derivatives thereof. In one embodiment, said differentiated cell is primitive ectoderm. In one embodiment, said differentiated cell is a part of a population of cultured cells. In one embodiment, said differentiated cell is at least 10% up to 100% of said population of cultured cells. In one embodiment, said differentiated cell in a population of cultured cells expresses Sex-determining region Y, box 1 (SOX1) protein. In one embodiment, said SOX1 is expressed within 24 hours of induction. In one embodiment, said SOX1 protein is expressed in at least 10% of said population of cultured cells. In one embodiment, said stem cell is selected from the group consisting of embryonic stem cells (including human embryonic stem cells (hESC)), somatic stem cells (e.g., human), and induced pluripotent stem cells (iPSC (e.g., human)). In one embodiment, said non-default differentiated cell is of ectodermal lineage.

One embodiment provides a composition comprising isolated primitive ectoderm. In one embodiment, said isolated ectoderm is derived from embryonic cells. In one embodiment, said primitive ectoderm is cultured in vitro (with a culture medium). In one embodiment, said ectoderm is anchored to substrate. In one embodiment, said ectoderm and embryonic stem cells are human.

One embodiment provides a composition comprising isolated neuromesoderm. In one embodiment, said isolated neuromesoderm is derived from embryonic cells. In one embodiment, said neuromesoderm is cultured in vitro (with a culture medium). In one embodiment, said neuromesoderm is anchored to substrate. In one embodiment, said neuromesoderm and embryonic stem cells are human.

One embodiment provides a method for screening biological agents, comprising, a) providing: i) a cell culture comprising ectoderm or neuromesoderm, and ii) a test compound, and b) contacting said ectoderm or neuromesoderm with said test compound. In one embodiment, biological agents are screened for the ability to further differentiate the ectoderm or neuromesoderm to desired cell lineages.

The invention contemplates methods for assessing the ectodermal identity of the derived ectoderm. This method can be through morphological means, functional assessment, and measurement of expression or downregulation of proteins associated with certain lineages.

The invention further contemplates methods for assessing the neuromesodermal identity of the derived neurtmesoderm. This method can be through morphological means, functional assessment, and measurement of expression or down regulation of proteins associated with certain lineages.

One embodiment provides a method for providing differentiated cells, comprising, a) providing: i) a cell culture of pluripotent stem cells (such as human pluripotent stem cells (hPSCs)), and ii) a compound for inducing differentiation, and b) contacting said stem cells with said compound.

DRAWINGS

FIG. 1: Innovations in deriving ectoderm from human pluripotent stem cells. Proof of concept was established with the spontaneous in vivo teratoma assay reported along with the initial derivation of human embryonic stem cells. The first in vitro method was described in 2000, and the first directed differentiation method was described in 2001. The first directed monolayer method was described in 2004, the first directed, monolayer, feeder-free method in 2006. Purity was improved in both 2009 and 2014. The present disclosure demonstrates novel conditions that promote substantial improvements in speed without sacrificing high purity.

FIG. 2A-C: Current Pluripotency and Directed Differentiation Mindsets.

Figure 3:
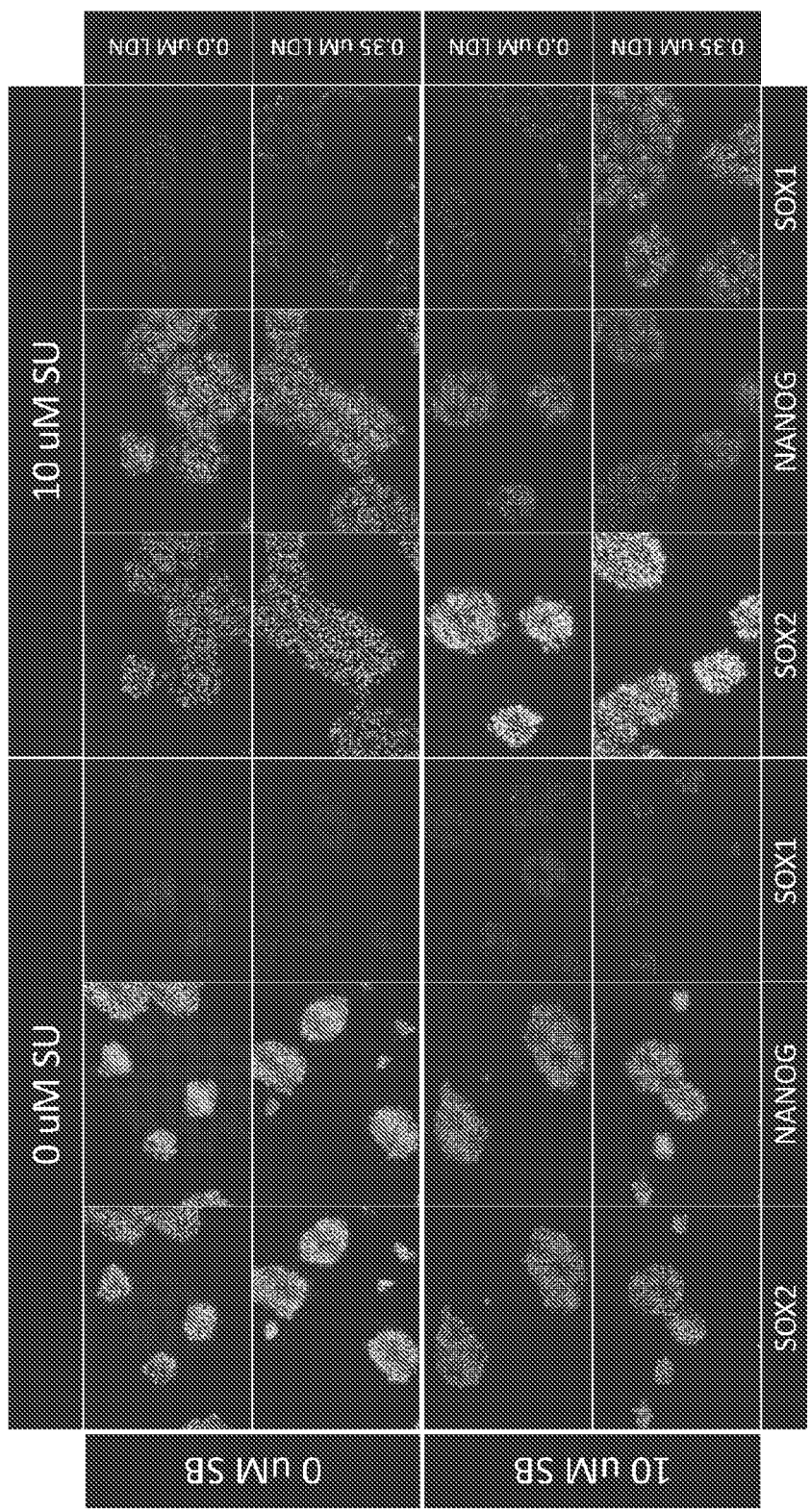

FIG. 3: Triple inhibition of hiPSCs with SU/LDN/SB creates homogenous SOX1-positive neural progenitors within 24 hours. hiPSC line R88 was exposed to LDN, SB, and SU in various combinations. Triple inhibition showed weakened NANOG staining, high SOX2/SOX1 immunopositivity, suggesting neural plate commitment.

Figures 4A, 4B, 4C:
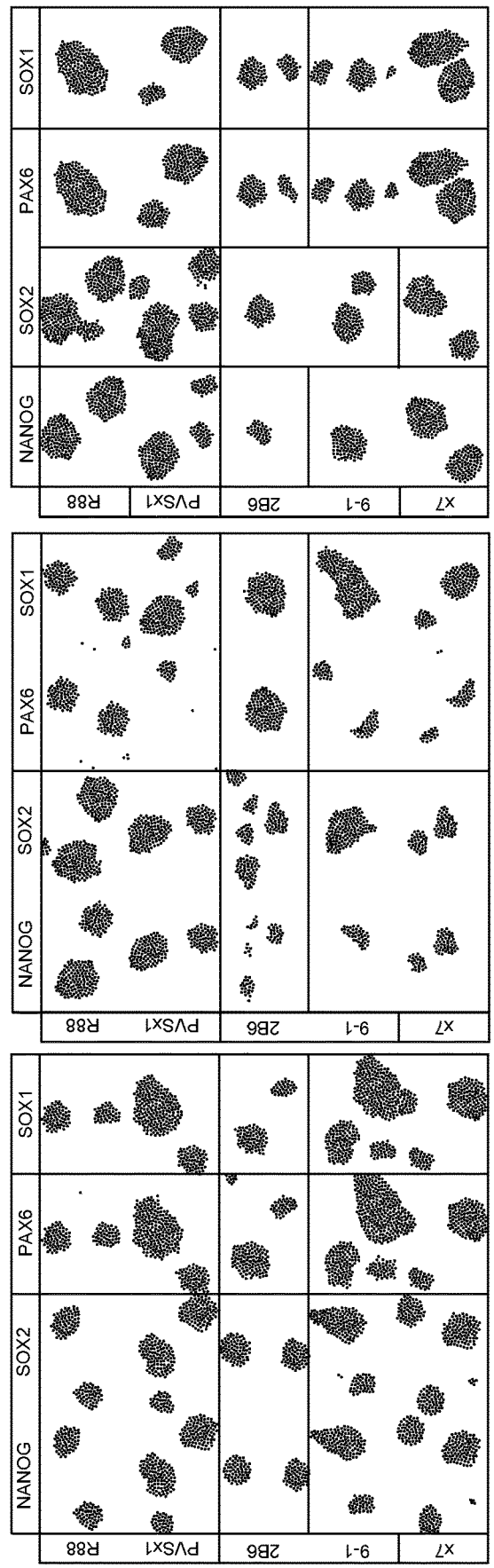

FIG. 4A-C: SU5402 functions through inhibition of FGF Signaling. A) SU/LDN/SB is applied to a panel of hiPSC lines for 24 hours. Neural induction occurs as evidenced by SOX1/SOX2 immunopositivity and weakened/absent NANOG staining. B) Axitinib, a potent and selective VEGFR1/2/3 inhibitor is substituted for SU5402. Induction occurs at only very high concentrations, causing morphological changes to nuclei. C) BGJ398, a potent and selective FGFR1/2/3 is substituted for SU5402. Use of BGJ398 during neural induction matches or exceeds marker expression levels seen when using SU5402.

Figure 5A:
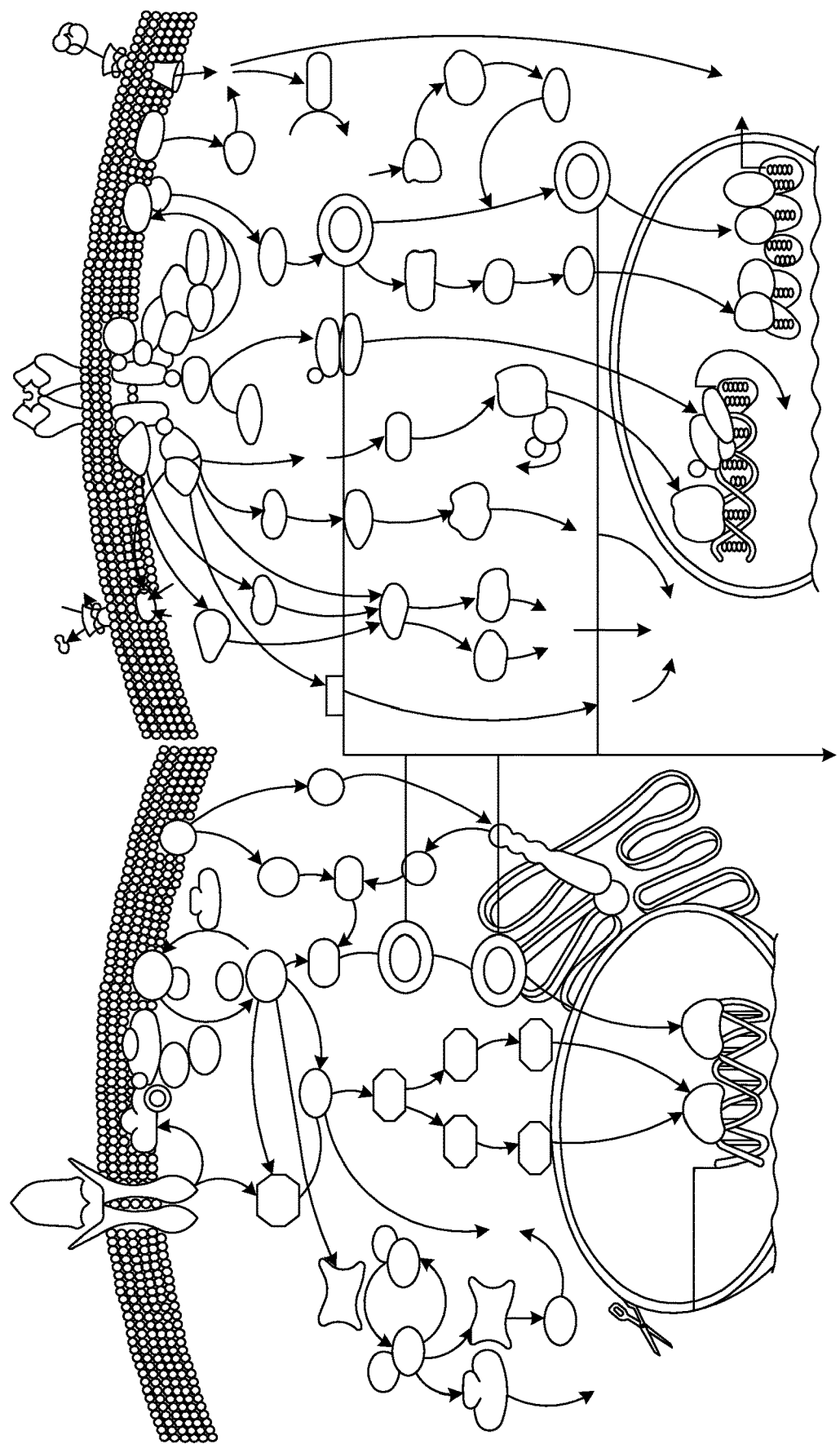
Figure 5B:
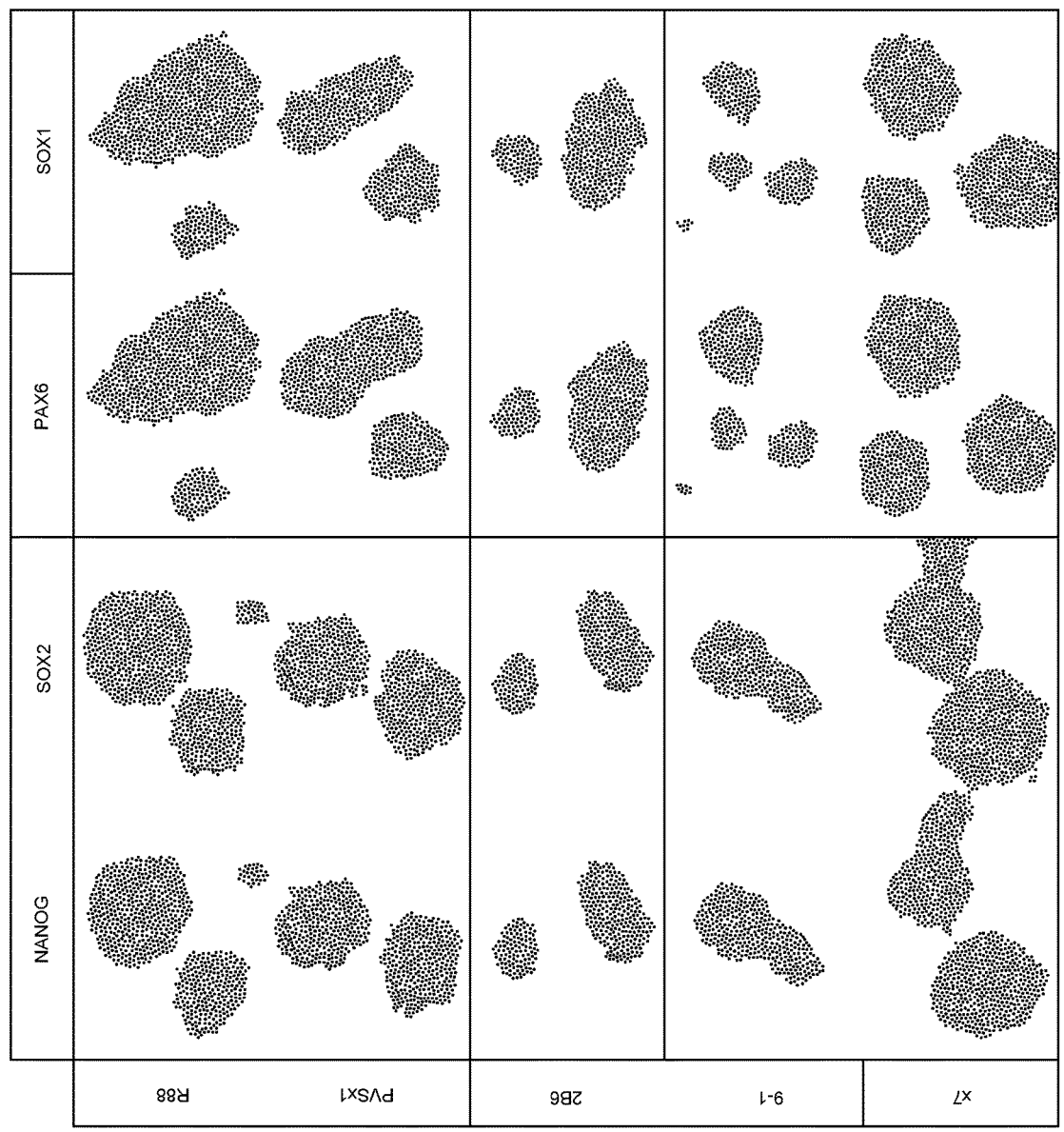

FIG. 5A-B: ERK inhibition substitutes for FGF inhibition during neural induction. A) MEK/ERK mediates growth factor signaling. The use of MEK inhibitor PD0325901 substitutes for SU5402.

Figure 6:
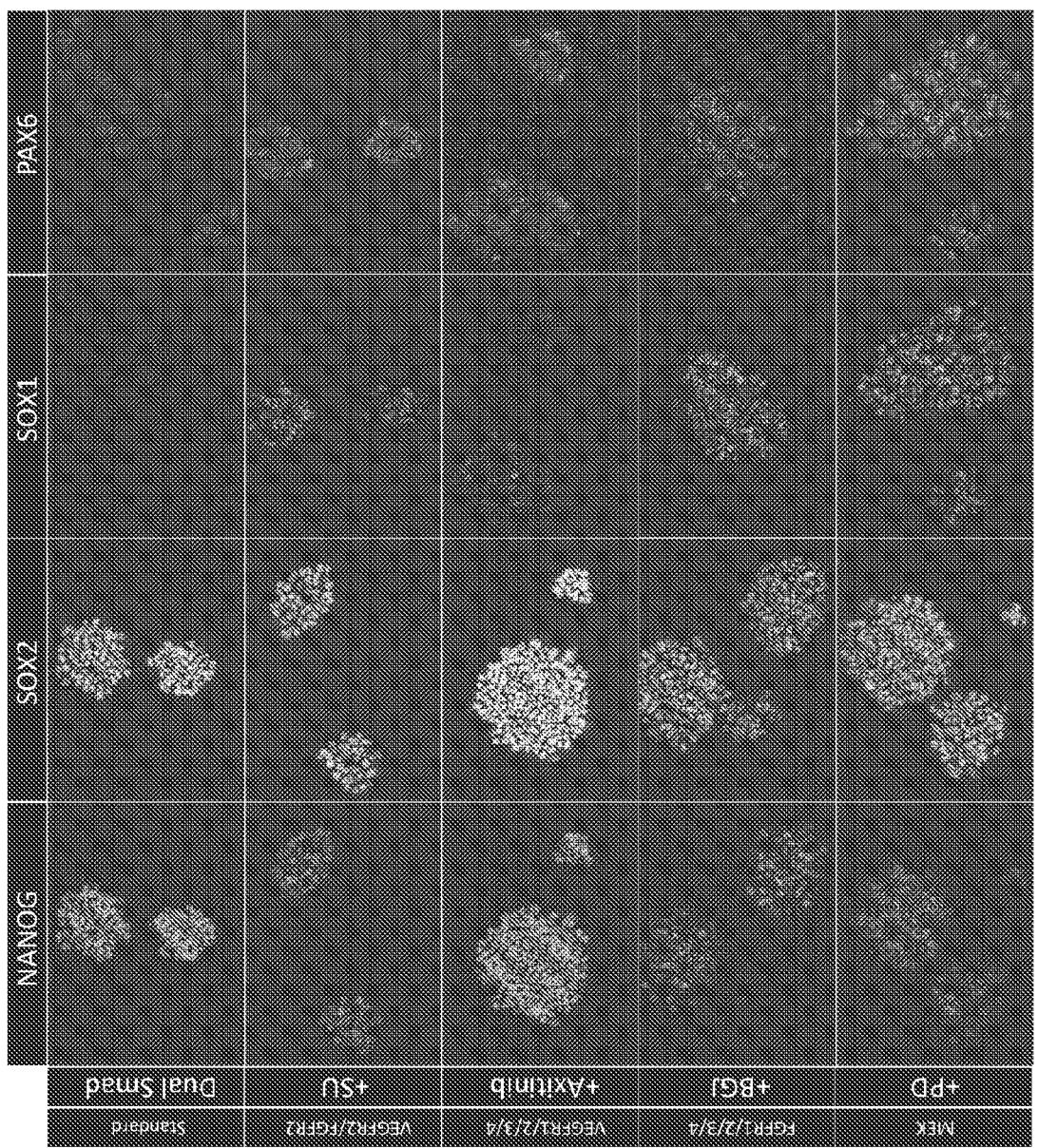

FIG. 6: SU Functions Primarily as a FGFR Inhibitor via MEK/ERK to Promote Neuroectoderm Formation Following 24 Hours.

Figure 7:
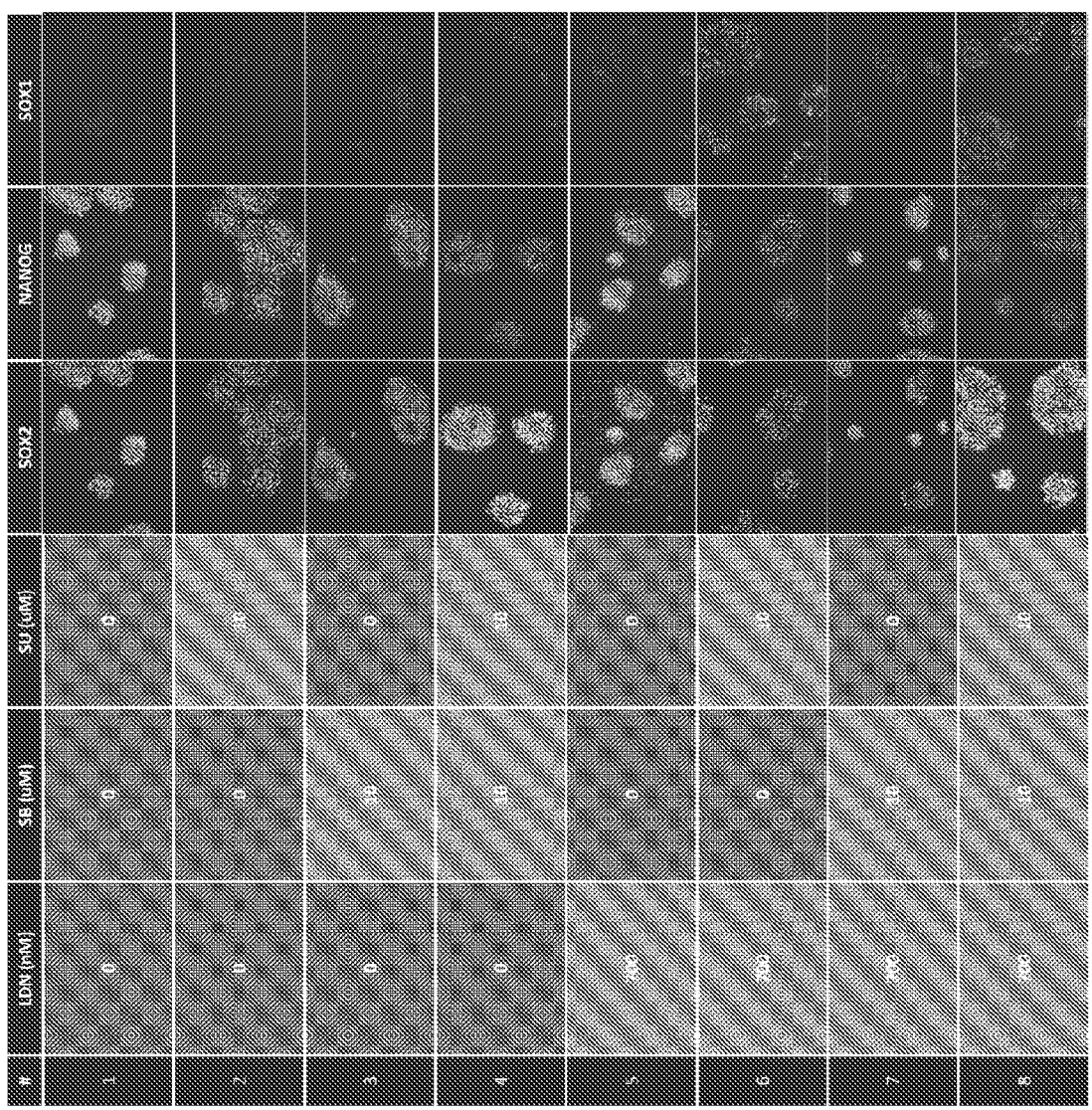

FIG. 7: Inhibition of FGFR2/VEGFR2, and ALK 2/3 (LDN/SU) is sufficient to promote SOX1 following 24 Hours Incubation.

Figure 8:
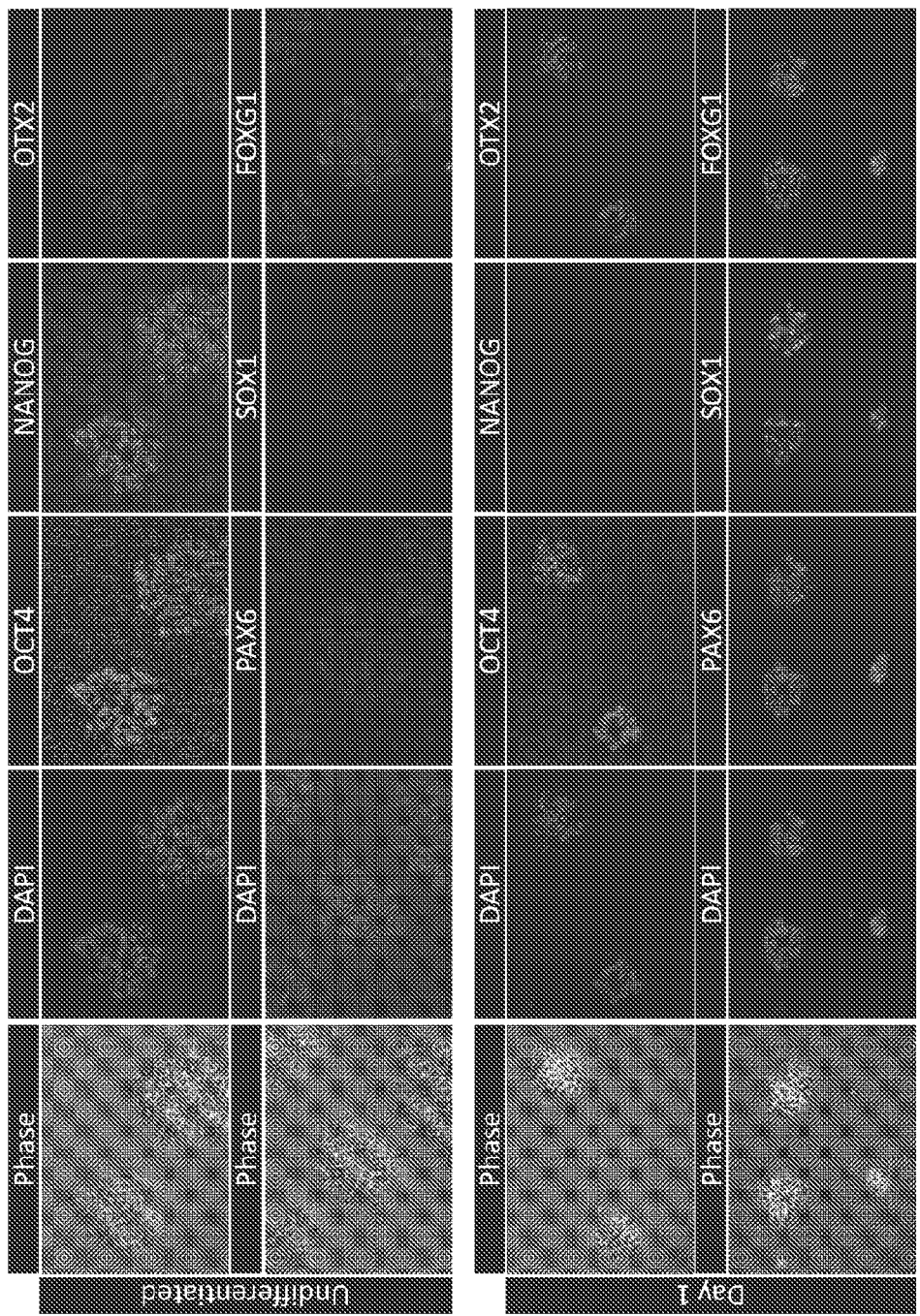

FIG. 8: Neuroepithelium Adopts Anterior Default.

Figure 9:
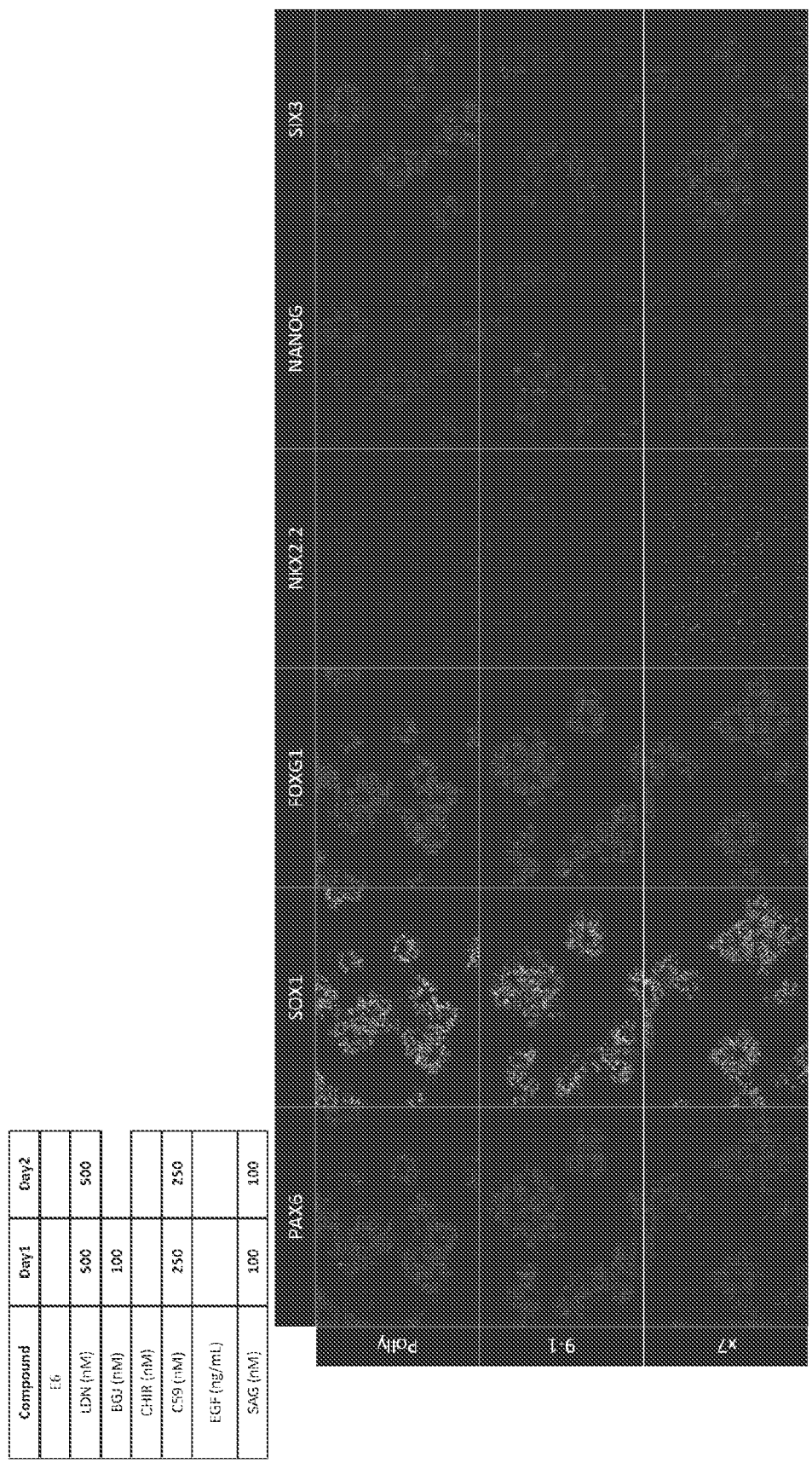

FIG. 9: Ventral Anterior Markers can be created.

Figure 10:
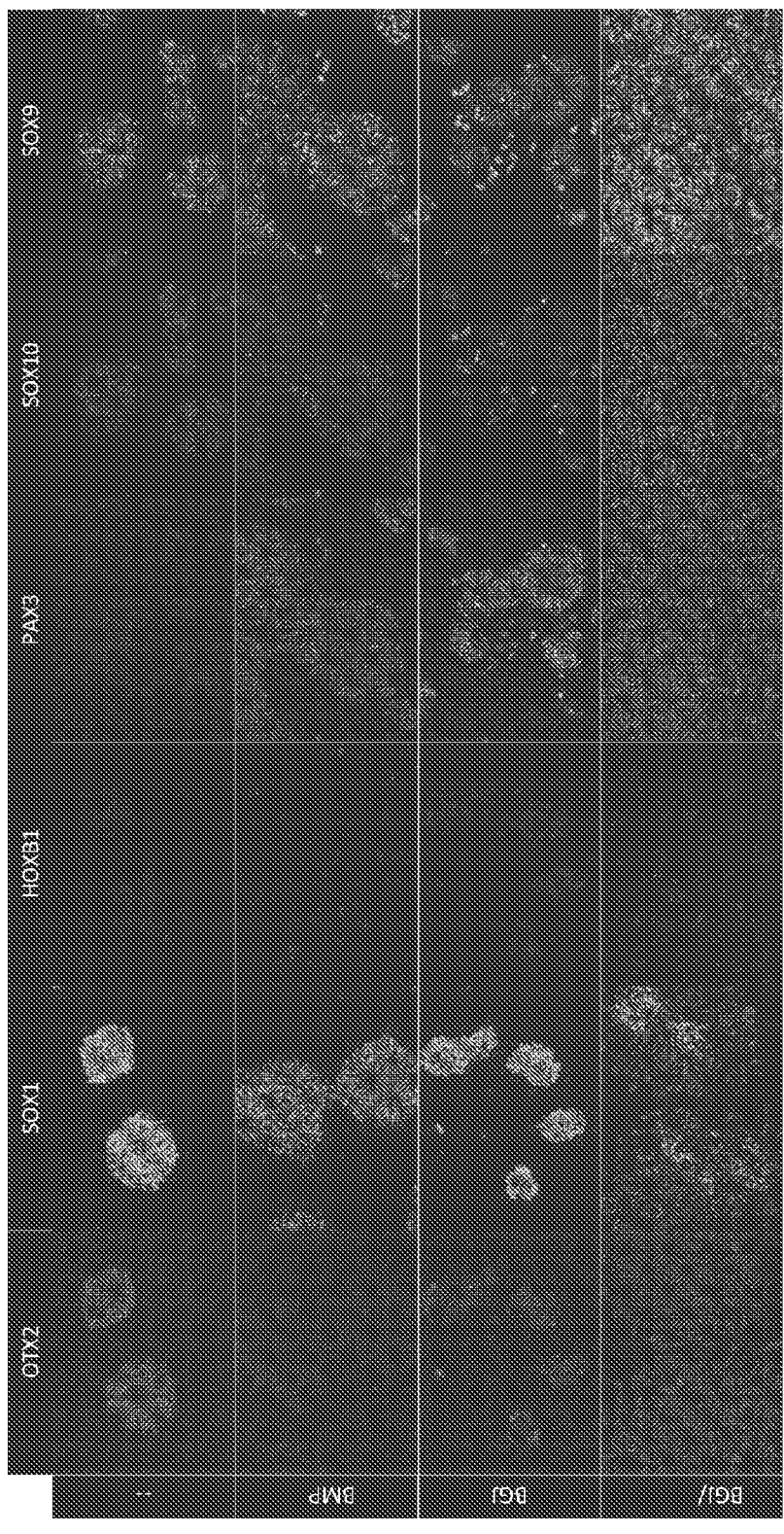

FIG. 10: Combined FGF Inhibition with BMP Signaling Promotes Homogenous Cranial Neural Crest from Midbrain Progenitors.

Figure 11:
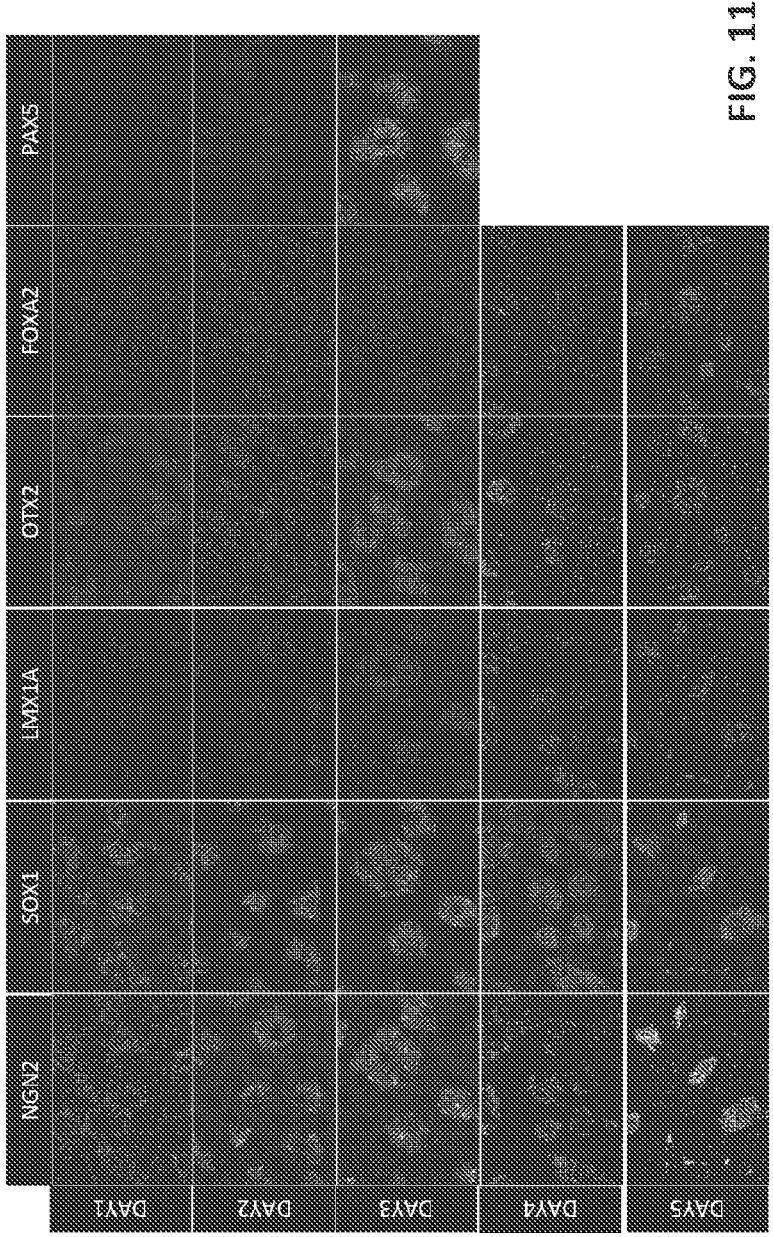

FIG. 11: Day-1 Neuroepithelium Can Be Patterned into Midbrain Floorplate (Caudal/Ventral) Phenotypes.

Figure 12:
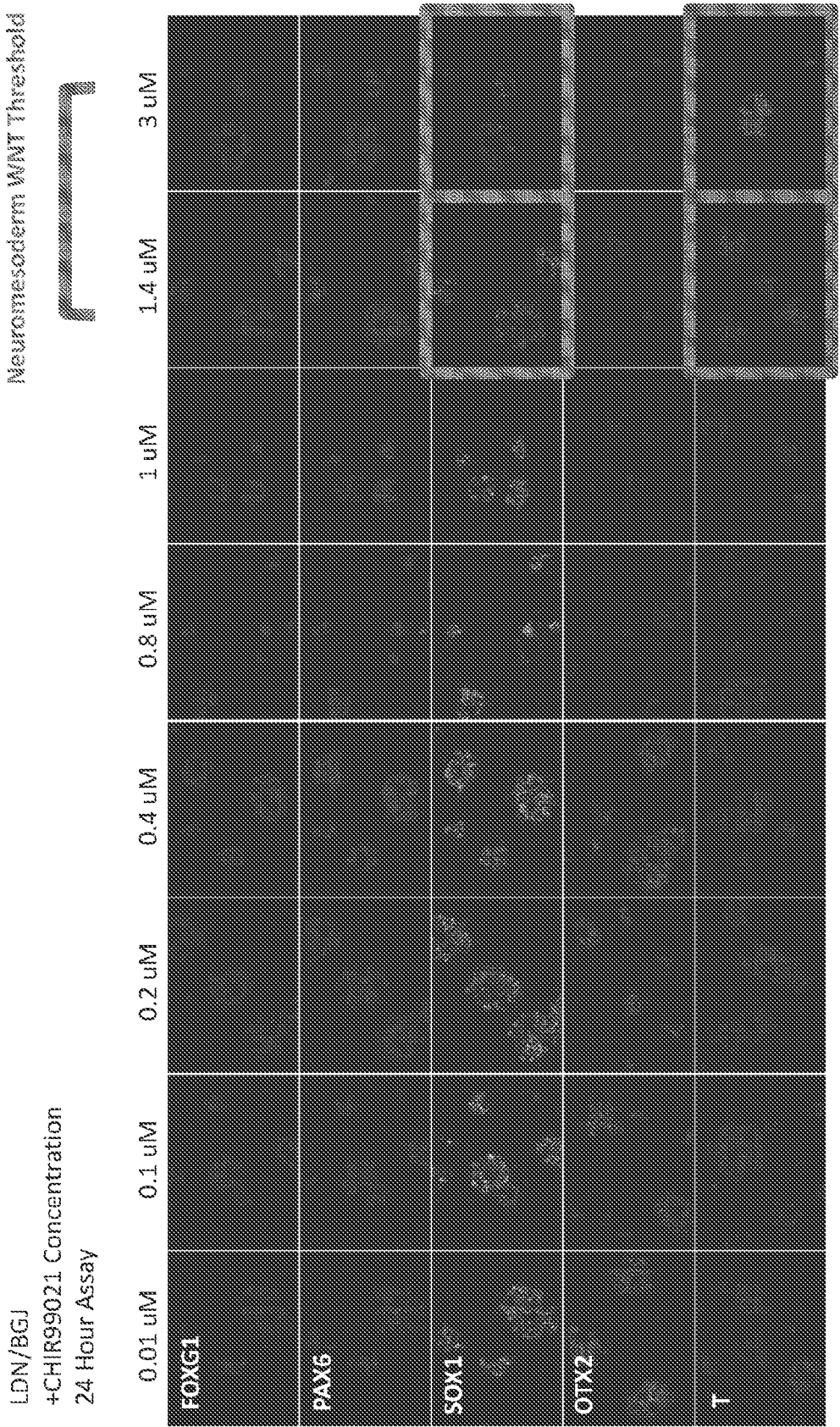

FIG. 12: A gradient of WNT Signaling Creates Posterior Fates in Combination with Day-1 Molecules.

Figure 13:
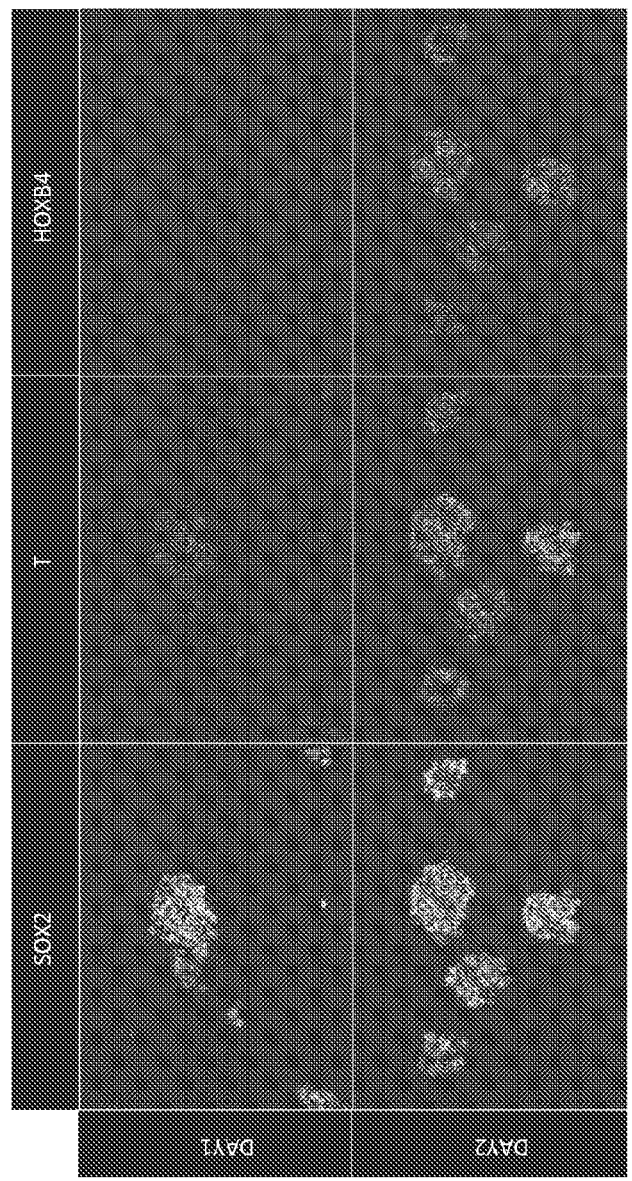

FIG. 13: High Day-1 WNT Signaling Creates 100% Neuromesoderm Capable of Co-linear HOX Activation.

Figure 14:
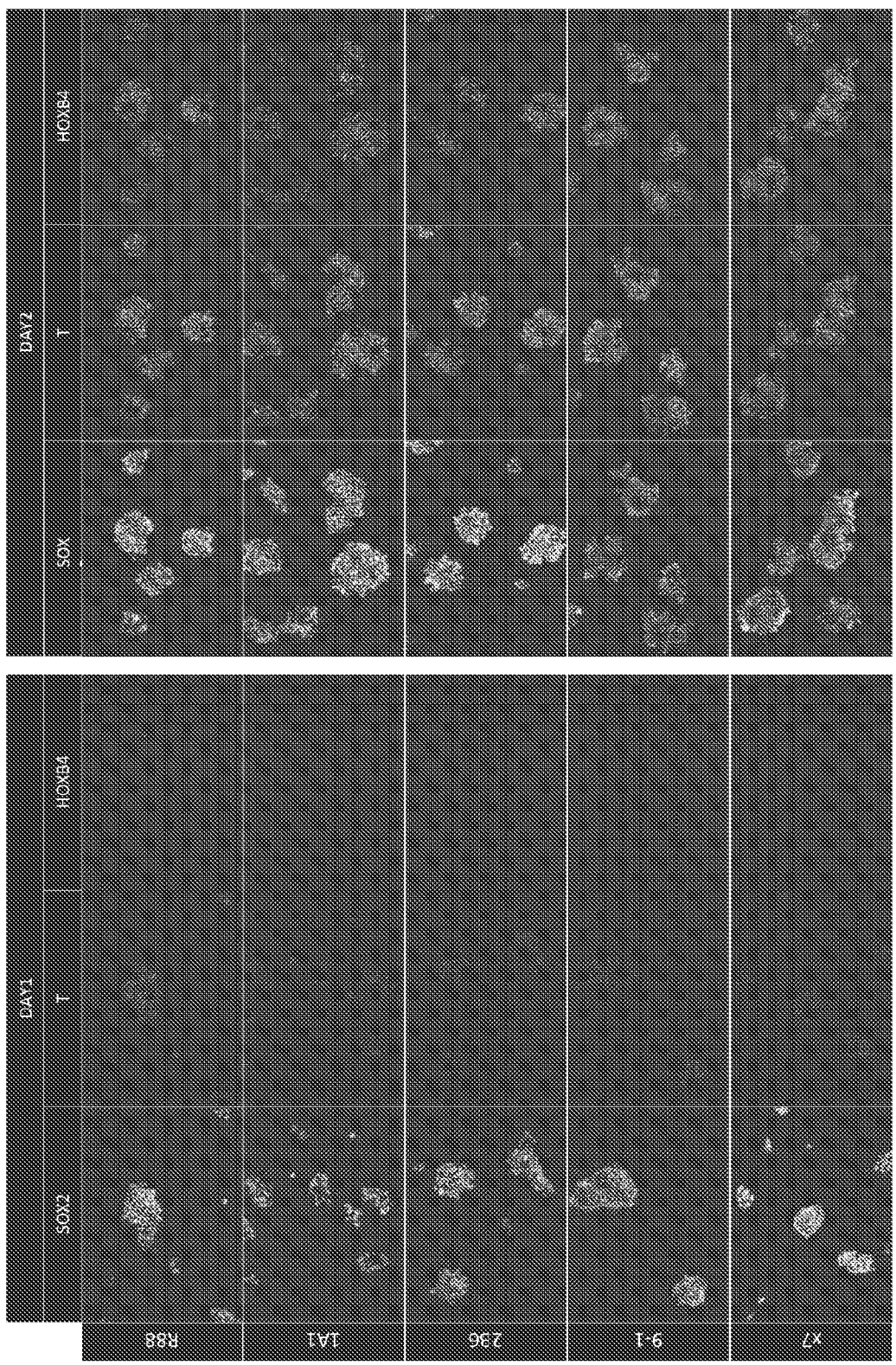

FIG. 14: Day-1 Neuromesoderm Induction Reproducible Across Lines.

FIG. 15: Neuromesoderm Fate Decision Rules.

Figure 16:
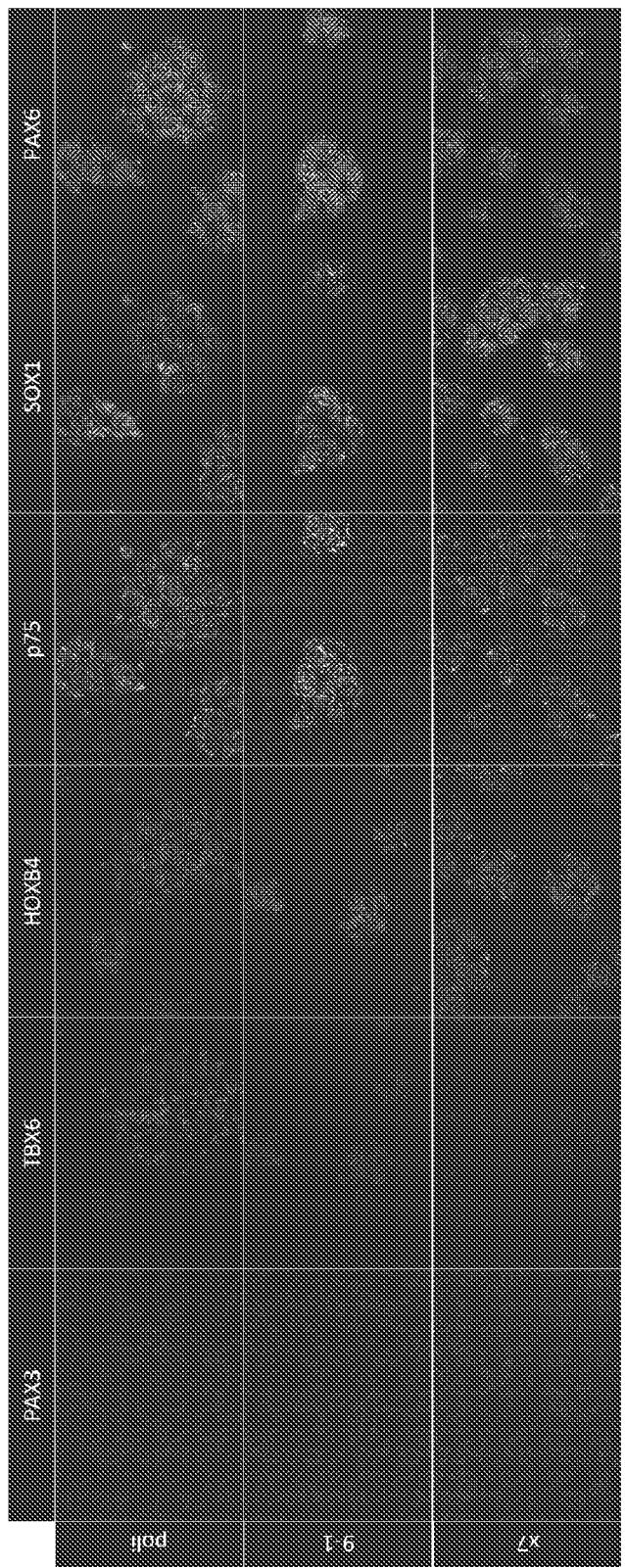

FIG. 16: Neuromesoderm Capable of Forming Somite (TBX6).

Figure 17:
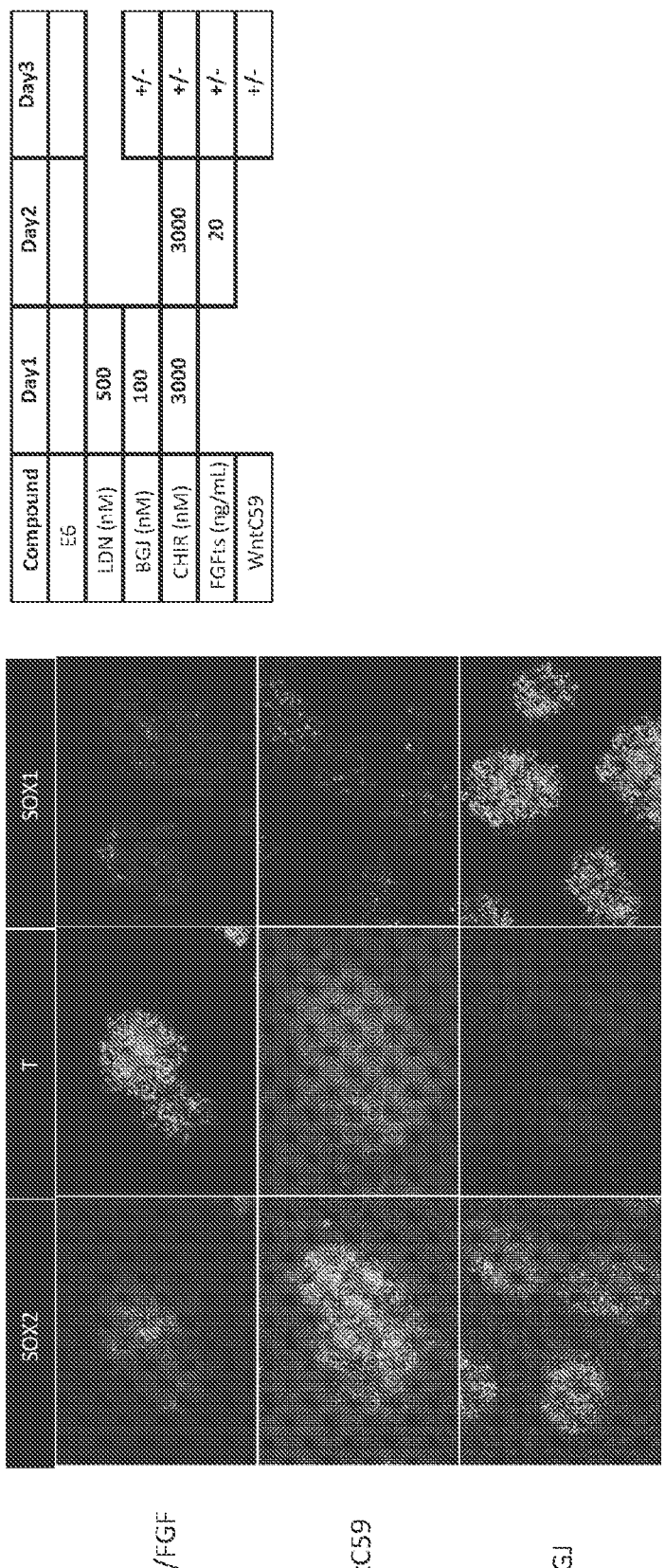

FIG. 17: Rule 1: FGF Stabilizes Neuromesoderm and Prevents Neural Plate Formation.

Figure 18:
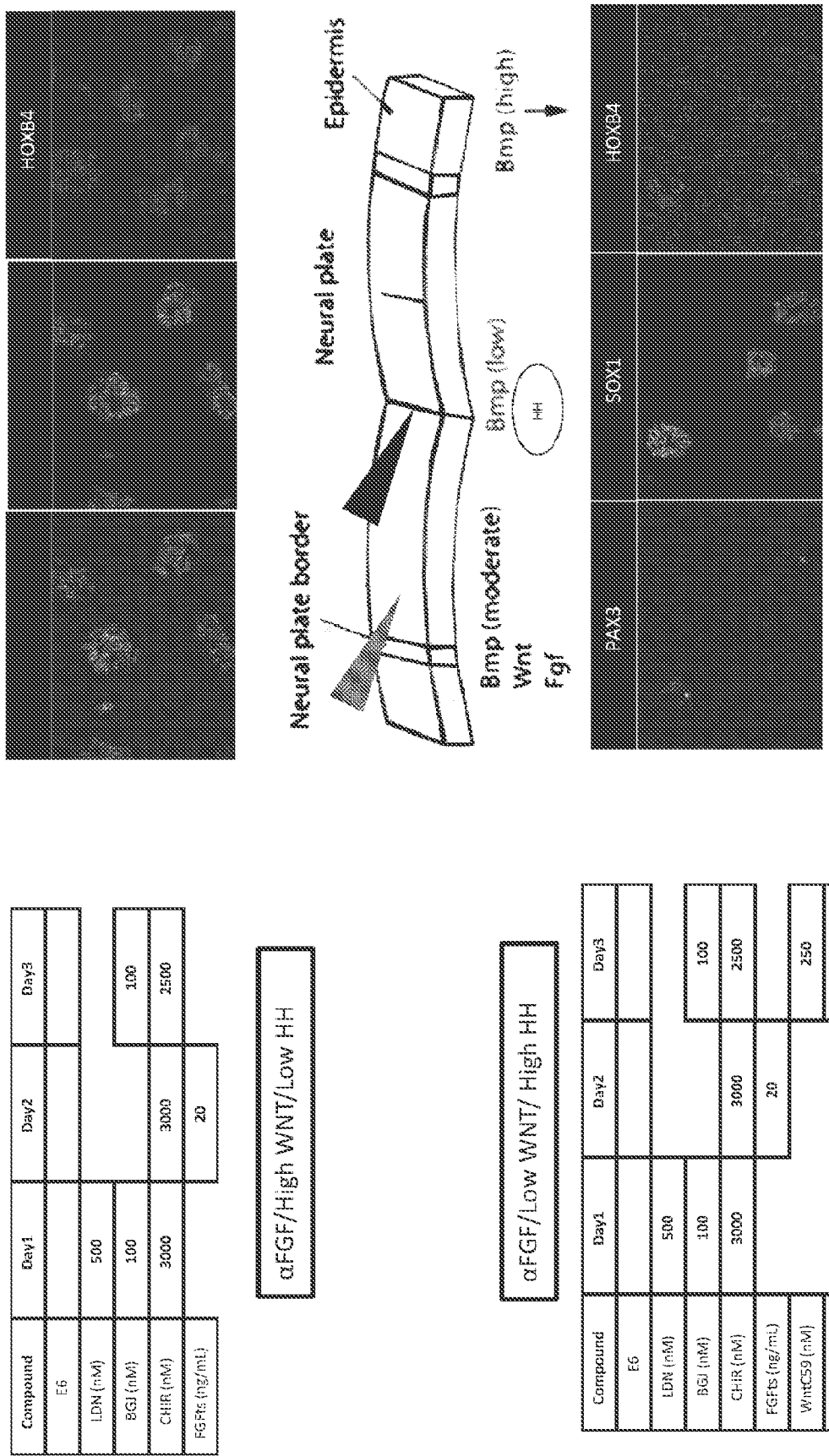

FIG. 18: Dorsal/Ventral Patterning Is Decided During Neural Plate Formation Dorsal/Ventral=Medial/Lateral.

Figure 19:
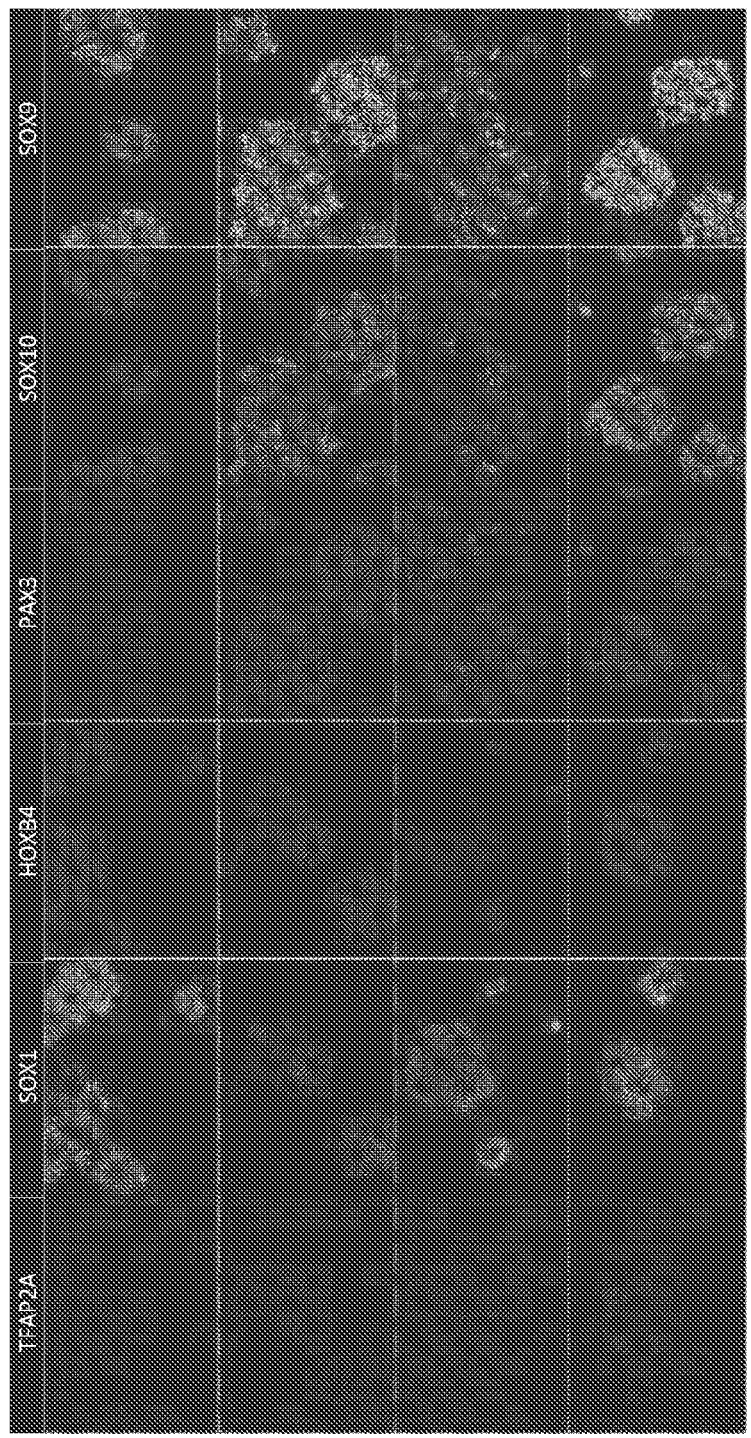

FIG. 19: Combined FGF Inhibition with BMP Signaling Promotes Homogenous Trunk Neural Crest from Neuromesoderm.

Figure 20:
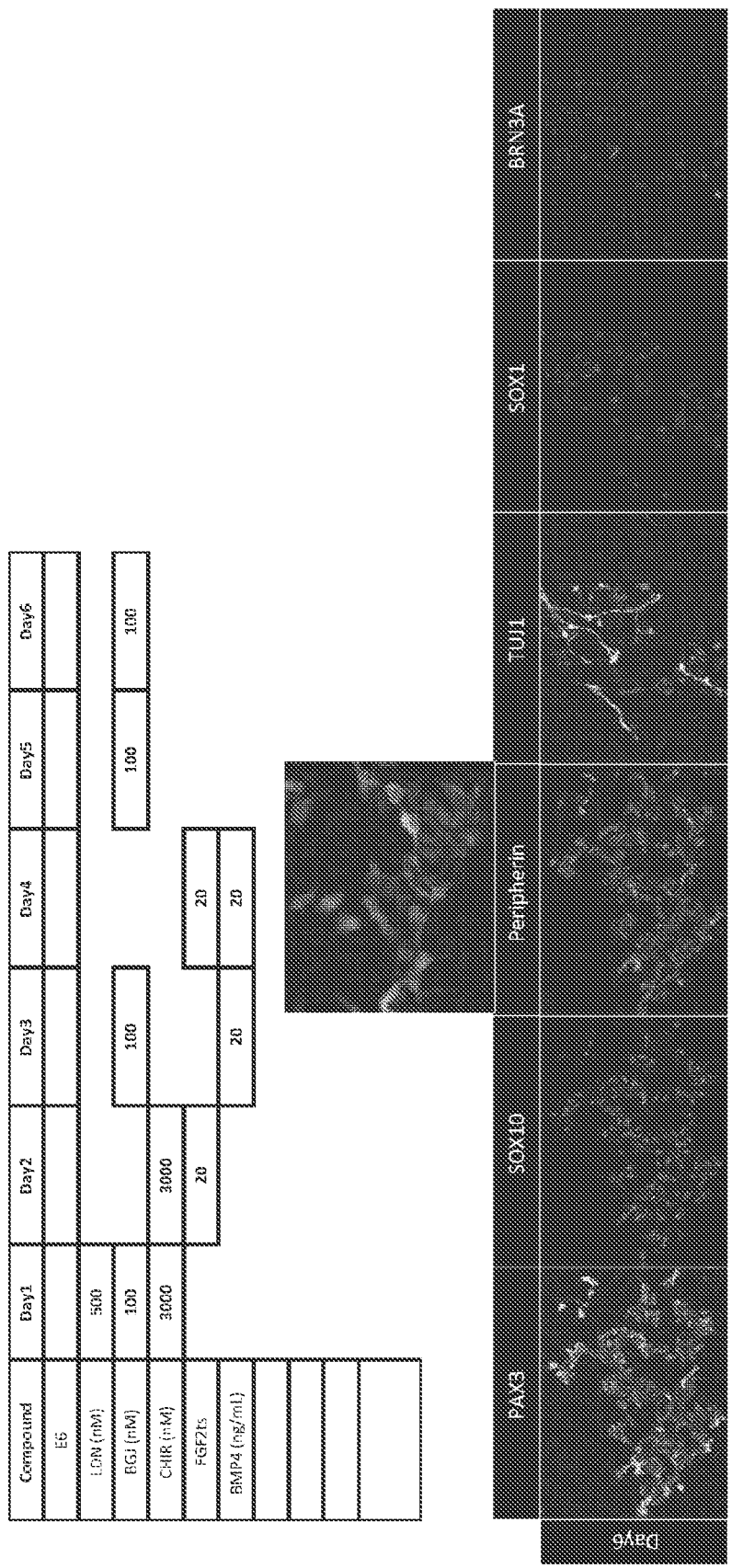

FIG. 20: Neural Crest Progenitors Can Differentiate to Peripheral Nerve.

Figure 21:
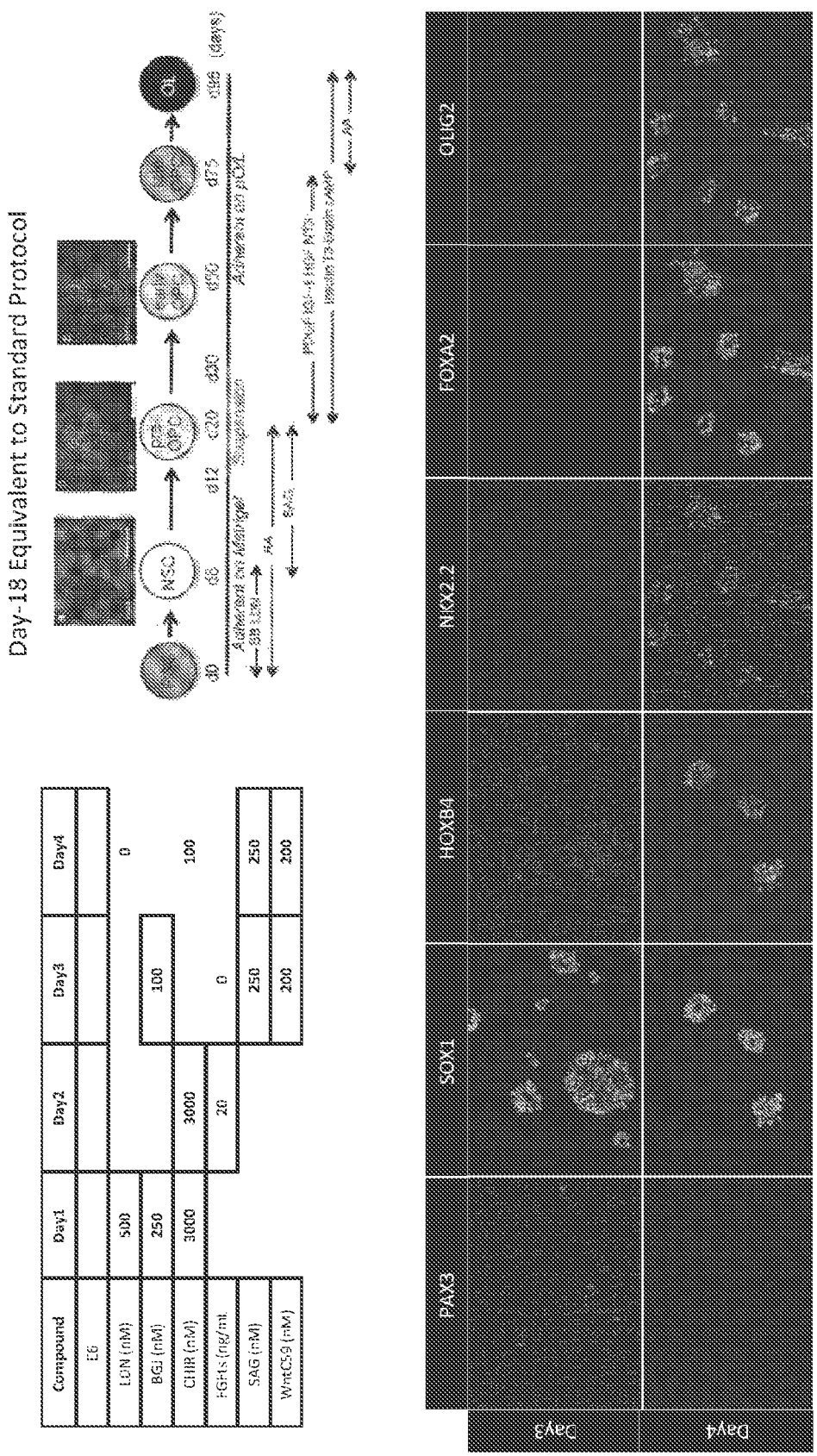

FIG. 21: Spinal Floorplate can be induced and expresses OLIG2/NKX2.2 (pre-OPC markers) within 4 days in Retinoid-Independent Fashion.

Figure 22:
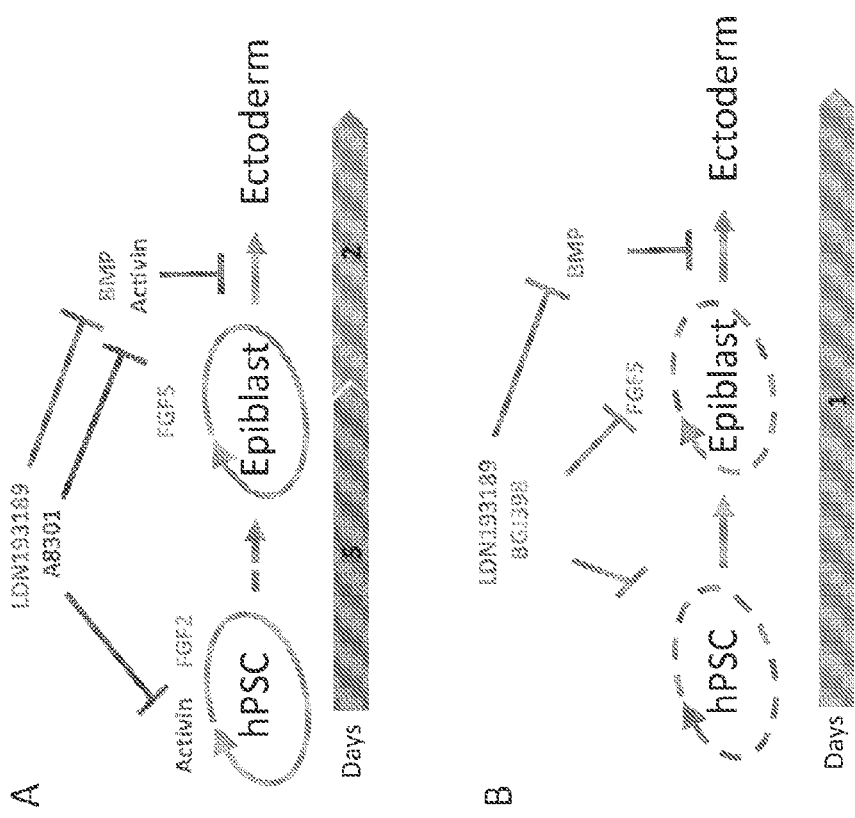

FIG. 22A-B: Model for Regulating Exit from Pluripotency into the Ectodermal Lineage. A) Established methodologies suppress Activin signaling with unregulated endogenous FGF signaling. Loss of pluripotency is thus slowed in transition to an FGF5 epiblast intermediate. During transition from epiblast, activing and BMP suppression generates ectoderm. B) Controlling FGF signaling spurs more rapid exit from pluripotency, as both FGF and Activin is suppressed. Similarly, the epiblast intermediate is transient due to controlled FGF signaling, and ectoderm is rapidly promoted due to suppression of Activin and BMP signaling. This results in a 6-day improvement in induction kinetics.

Figure 23:
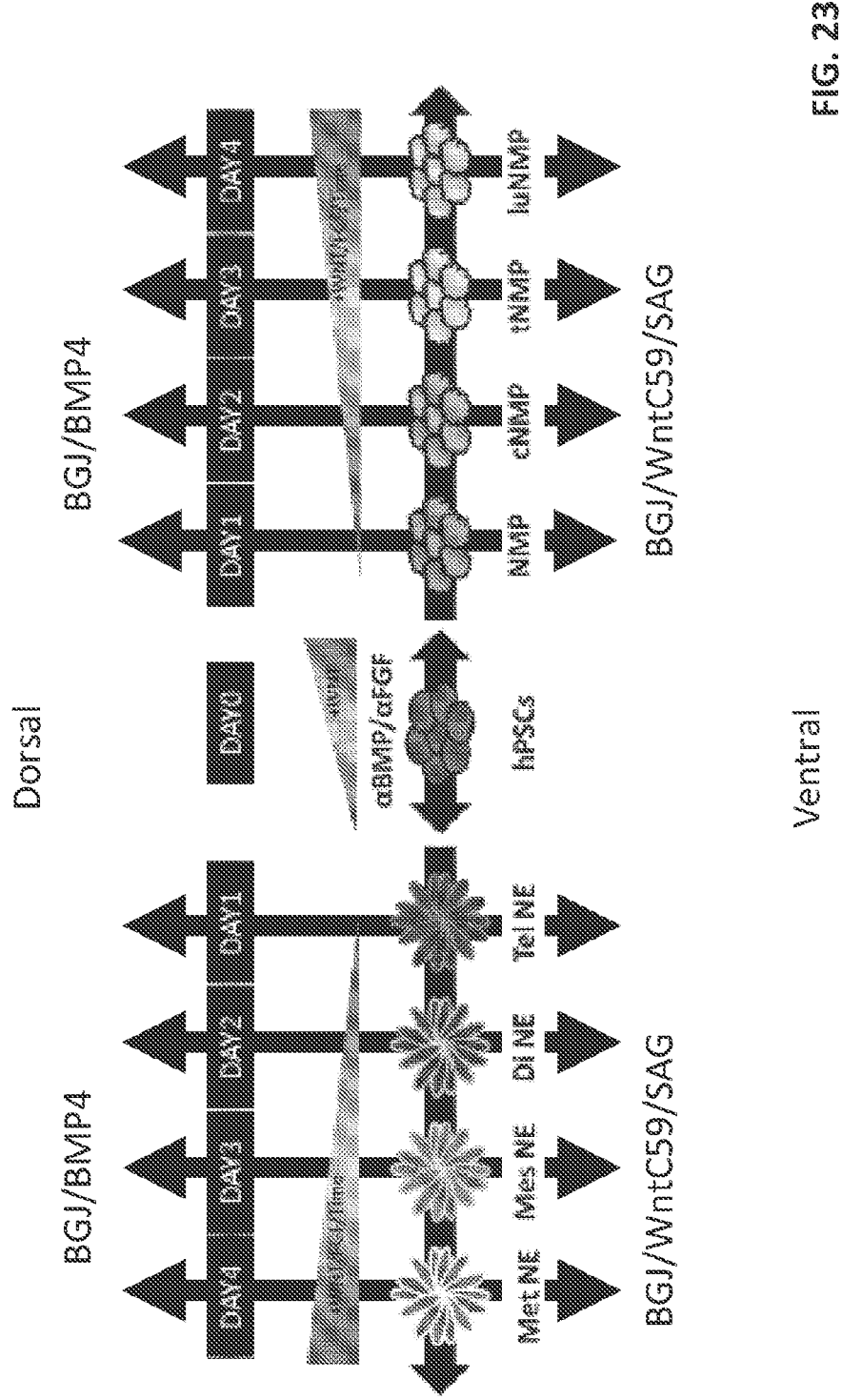

FIG. 23: Unified Platform for Direct Access to Anterior and Posterior Neuroepithelial Fates and Common Rules for Dorsal/Ventral Patterning.

FIG. 24A-D: Rostral Caudal patterning of the spinal cord. (A) During early development neuromesodermal progenitors (NMPs) differentiate to generate the length of the spinal cord. (B) Combinations of Hox gene expression dictate patterning of the spinal cord neurons that innervate different different parts of the body from each level (C, D).

Figure 25B:
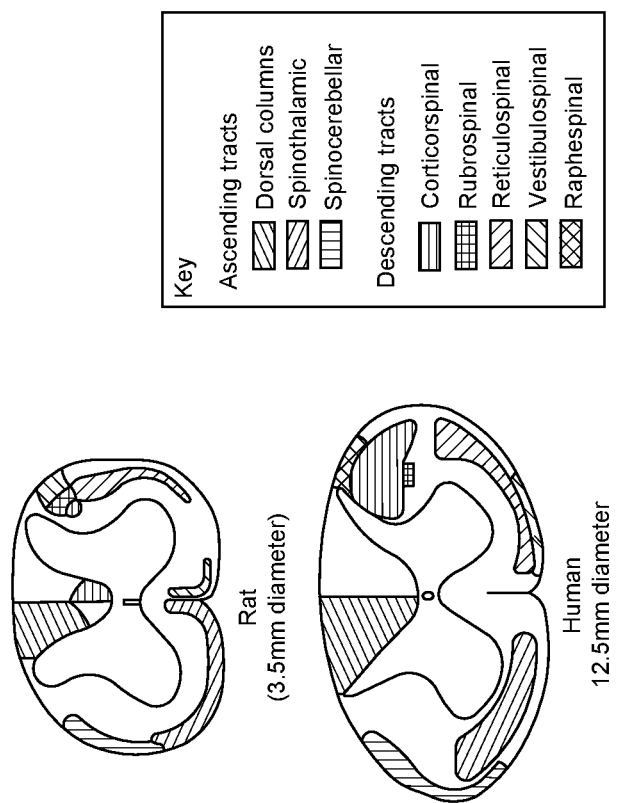
Figure 25A:
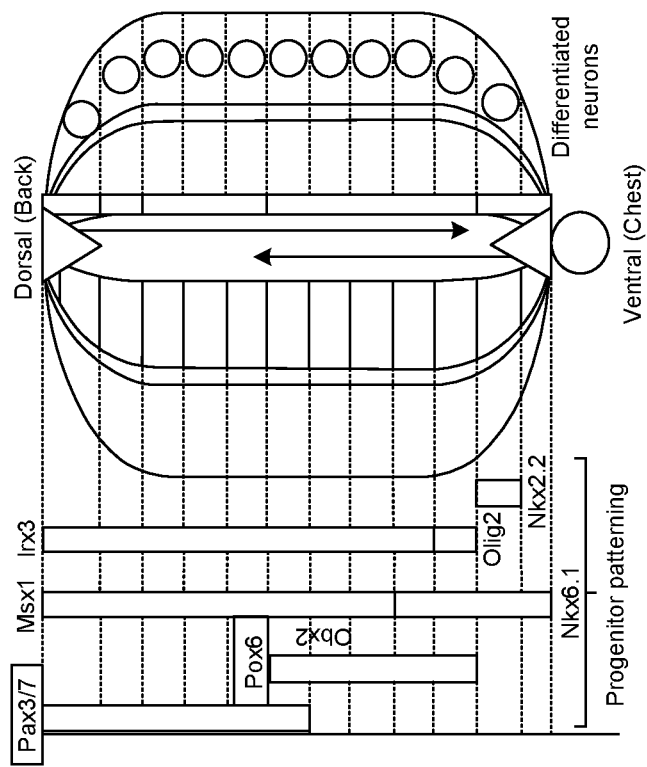
Figure 26A:
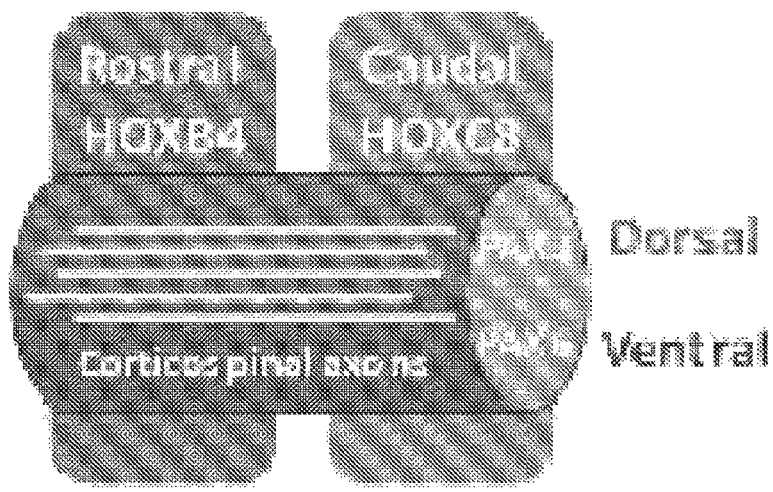
Figure 26B:
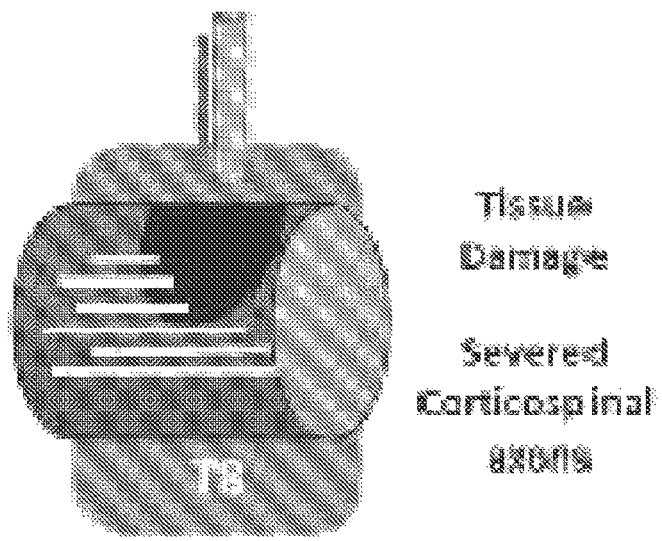
Figure 26D:
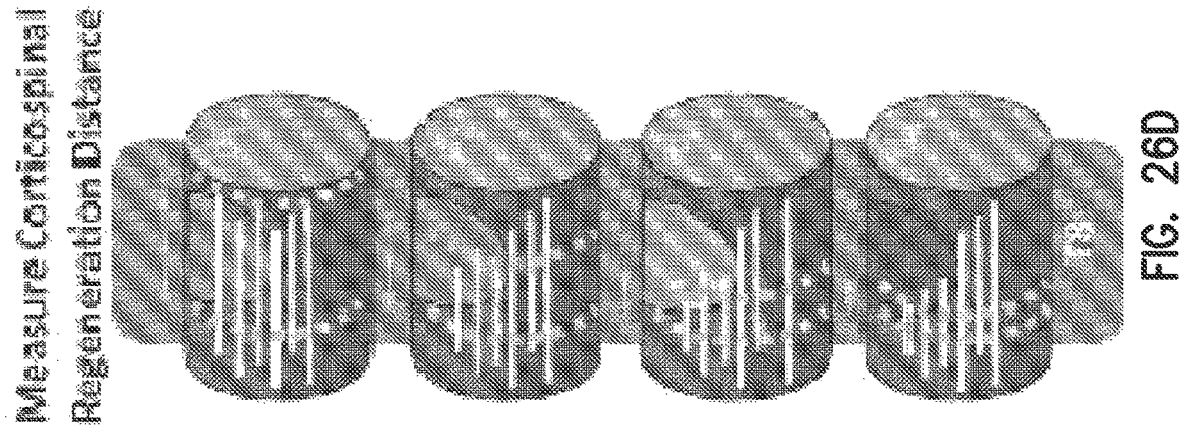
Figure 26C:
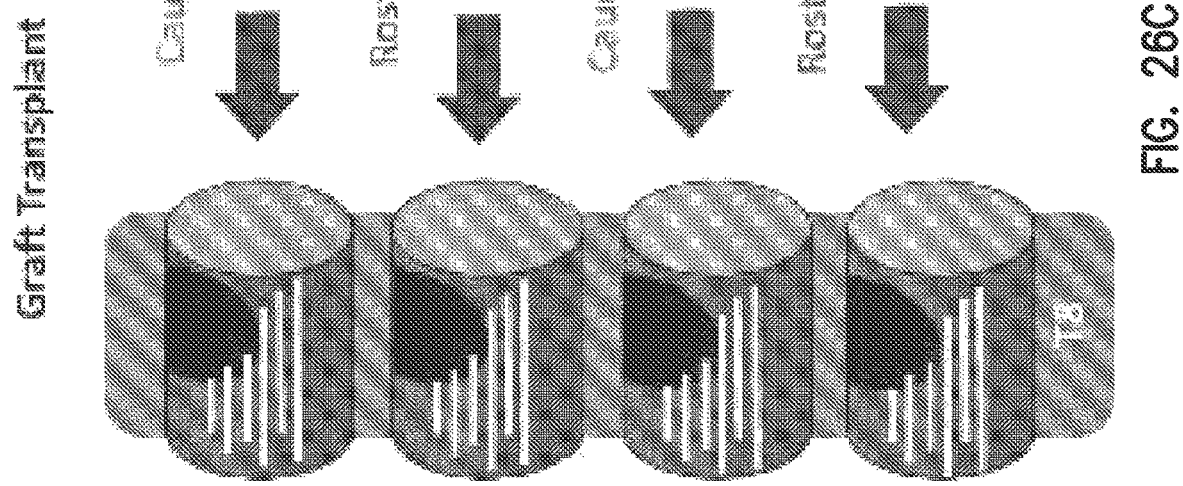

FIG. 25A-B: Dorsal\Ventral spinal cord complexity A) Signaling gradients during neural tube development induce the expression of combinations of transcription factors that pattern the dorsal/ventral identity of progenitor cells. These progenitors subsequently generate the complexity of differentiated neurons in the mature spinal cord. The early dorsal or ventral identity of neural tube progenitors can be broadly distinguished by Pax3 expression. B) Despite differences in size and some axon tract pathways, the adult rat and human spinal cord share important similarities and complexity in dorsal/ventral patterning. (Adapted from Nature reviews Neuroscience (2003) 4(7): 587-98 and Disease Models and Mechanisms (2016) 9, 1125-1137.)

FIG. 26A-D: A) Positional information of the spinal cord is determined during development to create rostrocaudal & dorsoventral domains. B) Animals will be given a reproducible 200 Kdyne dorsal/caudal T8 spinal cord contusion injury. C) The differentiation of human pluripotent stem cells (hPSCs) will be directed to generate spinal neural progenitor cells that contain specific intrinsic positional identities based on rostrocaudal and dorsoventral orientation. Cohorts of animals with cells matched orthotopically to the injury position or mismatched cells will be transplanted 7 days after the contusion injury. D) After 6 months, animals will be sacrificed and the graft contribution to regeneration at injury site be examined histologically. Graft cell identity and survival will be measured together witg injury site cavitation. Antero and retrograde axon tracing will be used to evaluate the distance of host axon migration into the graft.

Figure 27:
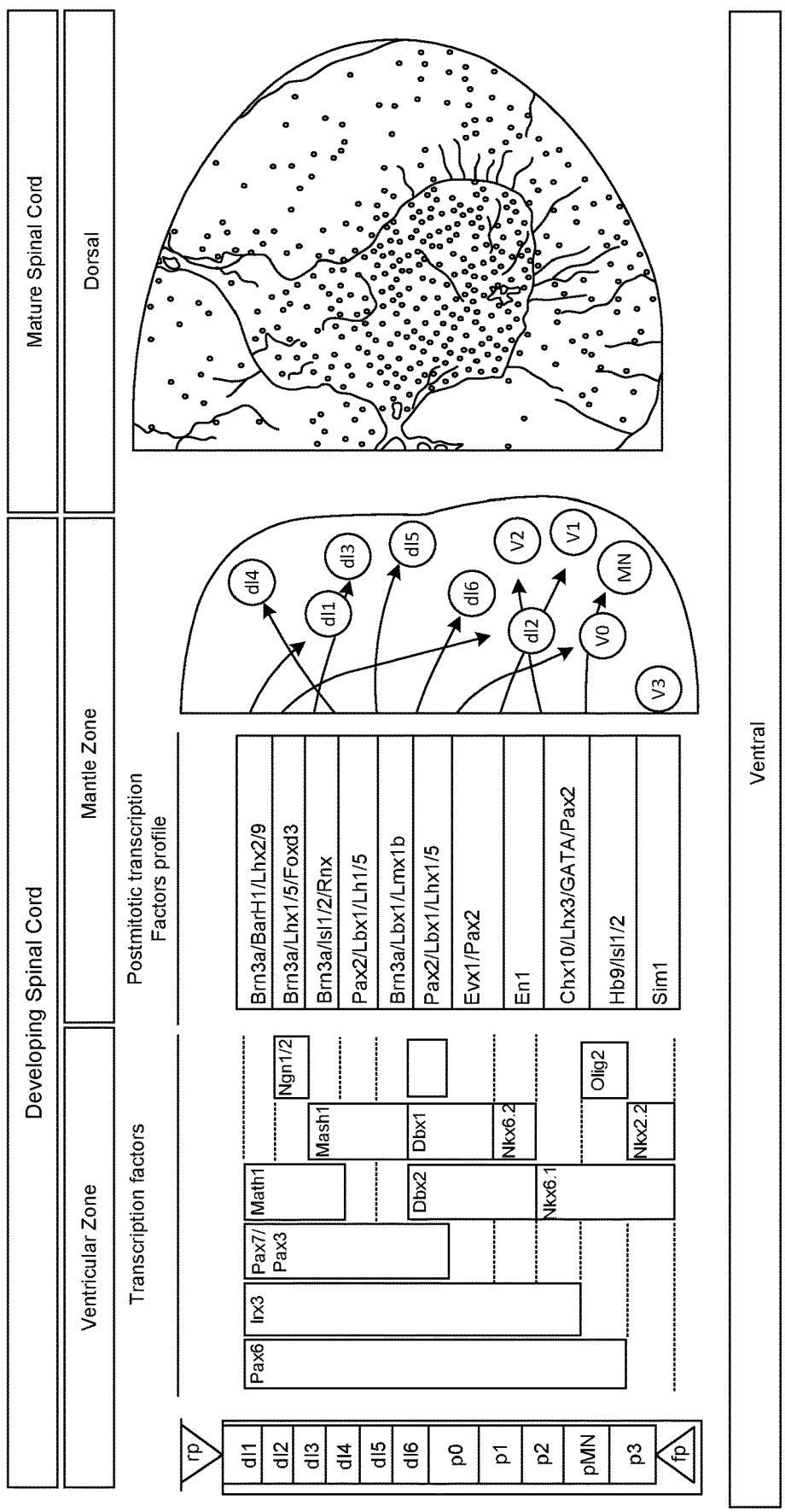
Figure 28A:
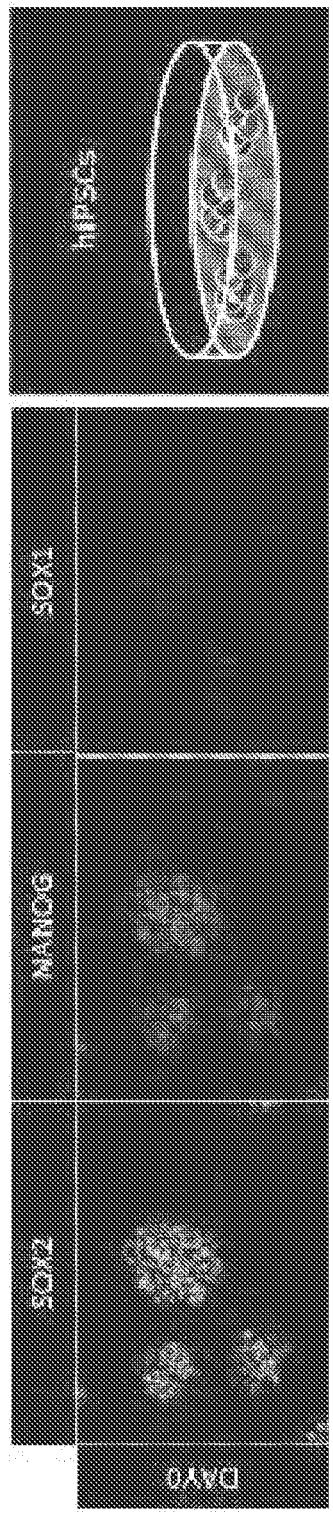
Figure 28B:
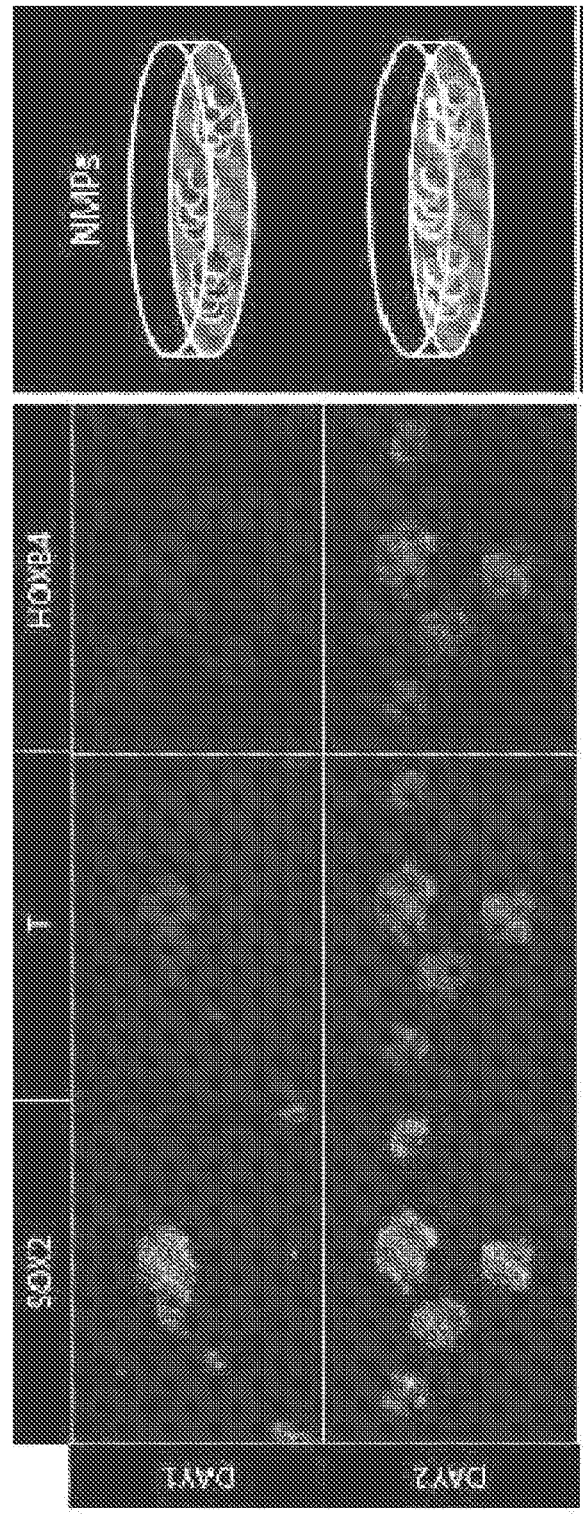
Figure 28C:
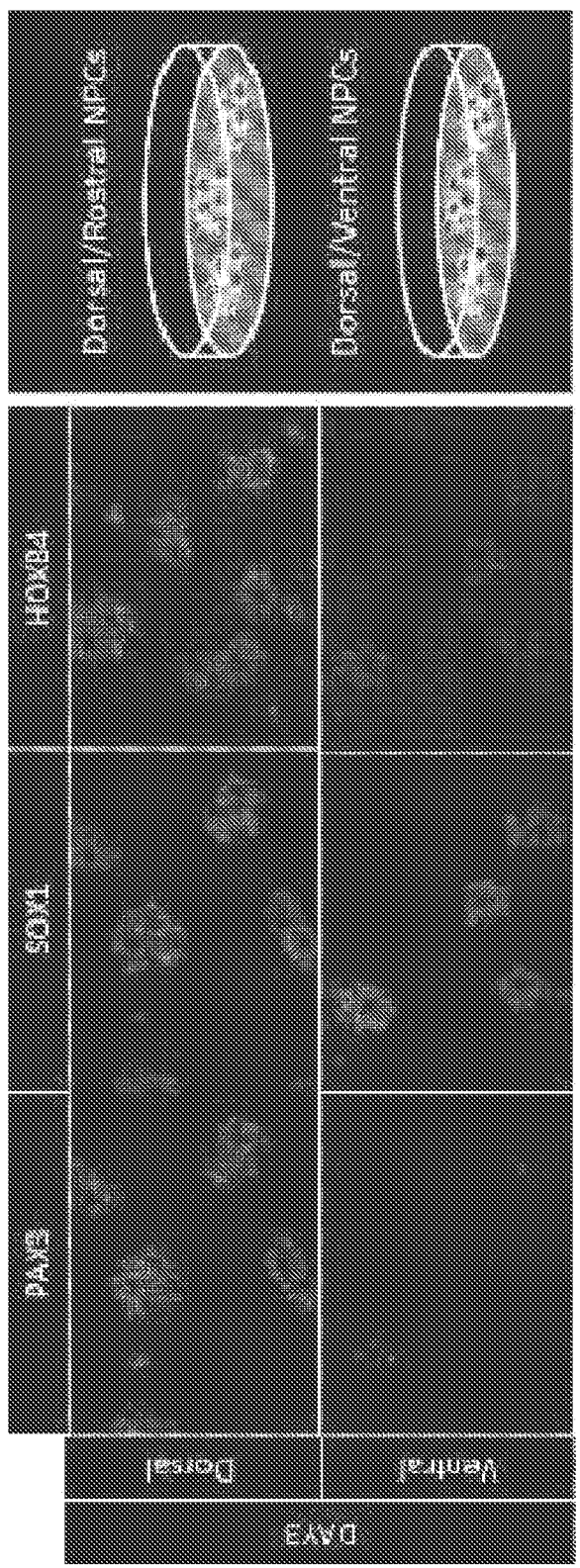
Figure 28D:
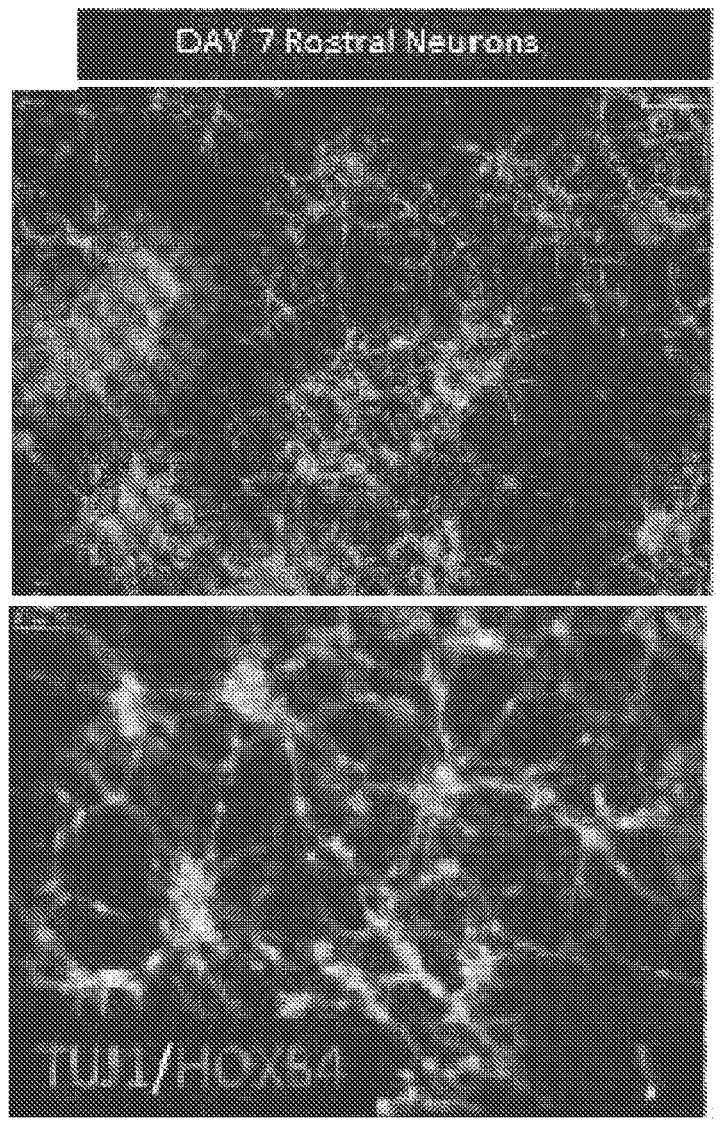

FIG. 27: Specific Aim 2. Refinement of dorso-ventral domain specificity during differentiation. The developing spinal cord consists of a twelve-domain architecture produced in two waves. An initial wave of specification creates the ventricular zone, a primitive neuroepithelium expressing unique combinations of transcription factors, each corresponding to a single domain. A second wave of specification occurs whereby the neurepithelium creates post-mitotic neuroblasts that migrate from the ventricular zone into the mantle zone. These neuroblasts, originating from a specific location in the ventricular zone, acquire a new combination of transcription factors as they enter the mantle zone and subsequently generate the diversity of spinal cord neurons.

FIG. 28A-D: Production of hiPSC-derived orthotopic and mismatched spinal cord neural grafts. A) Exiting pluripotency (Nanog/Sox2 co-expression) to produce neuro-mesoderm progenitors (Sox2/T co-expressing) B) with collinear HOX activation to produce more caudal cell populations of the formative spinal cord. C) Dorsal (Pax3 expressing) and ventral specification (Pax3-ve) during neural plate formation, and D) maturation into nascent neurons prior to transplant.

FIG. 29: List of several factors for use in the invention described herein. The factors can be used alone or in any combination.

DETAILED DESCRIPTION

The loss of sensation and motor function that results from spinal cord injury can lead individuals to lose independence, and significantly diminishing the quality and length of their lives. Clinically, spinal injuries are categorized by location, or "level", according to which vertebrae are affected by the injury from head-to-tail, and by their completeness, or how deep the injury has occurred across the spinal cord from front-to-back. The position of the damage along the spinal column dictates the extent of lost function, as each level of the spinal cord innervates different regions of the body. Function is lost both at and below the injury level due to severed axons that connect locally as well as corticospinal axons that transit from the cerebral motor cortex through the level to create distant connections farther down the spine. Transplantation of neural tissue made using human pluripotent stem cells has been proposed as a clinical treatment to restore function after spinal cord injuries. The transplant can replace lost nervous tissue, providing new neural networks. The transplant can also serve as bridge tissue for host axon regeneration from undamaged tissue above the injury site to undamaged tissue below the injury.

Previous research has indicated that damage occurring within a specific body region has the highest potential to be repaired by cells that belong in that specific region, also known as orthotopic grafting. Building on this premise, recent publications have highlighted the importance of the origin of graft tissue for spinal cord repair. Grafts originating from the brain failed to engraft into injured spinal cord, while spinal cord derived grafts performed better in the same injury setting. However, production of human pluripotent stem cell-derived neural progenitors defined by specific anatomical origin has proven technically challenging, limiting research designed to explore orthotopic grafting. Provided herein are new techniques for inducing and precisely controlling neural patterning from human pluripotent stem cells and are now in a position to test spinal neural grafts matched orthotopically to the injury position in an animal model for spinal cord injury.

Differentiation of human pluripotent stem cells proceeds stage-specifically to generate progressively more mature developmentally analogous embryonic structures in vitro. The first stage in generating all ectoderm in vitro has not proceeded faster than six days since the field was born in 1998. As such, creating any neuronal cell type requires at least six days to derive ectoderm, followed by additional time for developmentally later events to transpire. The compositions and methods provided herein abridges this interval to less than 24 hours, creating a new, accelerated time frame for these developmentally later events to occur. As such, any existing neuronal differentiation protocol can be re-written within the herein disclosed new time frame to increase efficiency.

Currently an art worker is forced to wait six days before proceeding to their next stage of differentiation. This limits productivity because the time from their experimental manipulation to their next result is at least one week. Experimenters are forced to wait that week, execute an experiment, analyze the result, and initiate a new experiment, limiting their total experiments to 50 per year. This creates inefficiencies with respect to time. Alternatively, they can initiate experiments more quickly without knowing the outcome of their previous manipulations. In such a scenario, experimental branches doomed to fail are pursued, creating inefficiencies with respect to time and material.

Provided herein are compositions and methods to generate ectoderm in a day/24 hours (or less), thereby improving efficiency as experiments can be planned, executed, data analyzed, and the best path forward taken with limited loss in productivity due to down-time or pursuit of failed experimental branches. The ectoderm has applications in pre-clinical as well as clinical settings.

Combined inhibition of Activin receptor-Like Kinases (ALK) 2, 3 and extracellular signal-regulated kinases (ERK) promote synchronous neural induction within 24 hours. Undifferentiated human pluripotent stem cells transition from a 95% NANOG/SOX2-positive, SOX1/PAX6-negative immunophenotype to a 95% NANOG-negative/SOX2 positive, PAX6 and/or SOX1-positive immunophenotype when exposed to the small-molecule combination of LDN 193189 and BGJ398. The fibroblast growth factor receptor inhibitor BGJ398 has been found to inhibit downstream ERK signaling, as the MAPK/ERK kinase inhibitor PD0325901 fully replaces use of BGJ398 in this setting.

This discovery is currently the most simple and efficient platform upon which protocols for deriving cell types of all neural lineages can be built, and is a vast improvement upon existing methods.

Similarly, the first stage in generating neuromesoderm in vitro has not proceeded faster than 3 days. As such, creating any neuronal or mesodermal cell type requires at least 3 days to derive neuromesoderm, followed by additional time for developmentally later events to transpire. The compositions and methods provided herein abridges this interval to less than 24 hours, creating a new, accelerated time frame for these developmentally later events to occur. As such, any existing neuromesodermal differentiation protocol can be re-written within the herein disclosed new time frame to increase efficiency.

Currently an art worker is forced to wait three days before proceeding to their next stage of differentiation. This limits productivity because the time from their experimental manipulation to their next result is at least three days. Experimenters are forced to wait that time, execute an experiment, analyze the result, and initiate a new experiment, limiting their total experiments to 100 per year. This creates inefficiencies with respect to time. Alternatively, they can initiate experiments more quickly without knowing the outcome of their previous manipulations. In such a scenario, experimental branches doomed to fail are pursued, creating inefficiencies with respect to time and material.

Provided herein are compositions and methods to generate neuromesoderm in a day/24 hours (or less), thereby improving efficiency as experiments can be planned, executed, data analyzed, and the best path forward taken with limited loss in productivity due to down-time or pursuit of failed experimental branches. Thus, the neuromesoderm has applications in pre-clinical as well as clinical settings.

Combined inhibition of Activin receptor-Like Kinases (ALK) 2, 3, extracellular signal-regulated kinases (ERK), and activation of WNT pathways promote synchronous neuromesoderm formation within 24 hours. Undifferentiated human pluripotent stem cells transition from a 95% NANOG/SOX2-positive, T-negative immunophenotype to a 95% NANOG-negative/SOX2/T-positive immunophenotype when exposed to the small-molecule combination of LDN193189, BGJ398, and CHIR99021. The fibroblast growth factor receptor inhibitor BGJ398 has been found to inhibit downstream ERK signaling, as the MAPK/ERK kinase inhibitor PD0325901 fully replaces use of BGJ398 in this setting. This discovery is currently the simplest and most efficient platform upon which protocols for deriving cell types of all neuromesoderm lineages can be built, and improves on existing methods by a factor of three.

Definitions:

In describing and claiming this disclosure, the following terminology will be used in accordance with the definitions set forth below. Unless defined otherwise, all technical and scientific terms used herein have the same meaning as commonly understood by one of ordinary skill in the art to which this disclosure belongs. Any methods and materials similar or equivalent to those described herein can be used in the practice or testing of the present invention. Specific values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

"Cells" include cells from a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

"Progenitor cells" are cells produced during differentiation of a stem cell that have some, but not all, of the characteristics of their terminally differentiated progeny. Defined progenitor cells, such as "endothelial progenitor cells," are committed to a lineage, but not to a specific or terminally differentiated cell type.

"Self-renewal" refers to the ability to produce replicate daughter stem cells having differentiation potential that is identical to those from which they arose. A similar term used in this context is "proliferation."

"Expansion" refers to the propagation of a cell or cells without differentiation.

"Pluripotent" in the context of cells refers to stem cells that have the potential/ability to differentiate into any of the three germ layers: endoderm (interior stomach lining, gastrointestinal tract, the lungs), mesoderm (muscle, bone, blood, urogenital), or ectoderm (epidermal tissues and nervous system). However, cell pluripotency is a continuum, ranging from the completely pluripotent cell that can form every cell of the embryo proper, e.g., embryonic stem cells and iPSCs (see below), to the incompletely or partially pluripotent cell that can form cells of all three germ layers, but that may not exhibit all the characteristics of completely pluripotent cells.

"Engraft" or "engraftment" refers to the process of cellular contact and incorporation into an existing tissue of interest in vivo.

"Cytokines" refer to cellular factors that induce or enhance cellular movement, such as homing of stem cells, progenitor cells or differentiated cells. Cytokines may also stimulate such cells to divide.

"Differentiation factors" refer to cellular factors, preferably growth factors or factors that induce lineage commitment.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology. Peptides provided for herein are at least 50%, 60%, 70%, 80%, 90%, 95%, 96%, 97%, 98%, 99% or 100% identical to those provide for in Table I.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

As used herein, "treat," "treating" or "treatment" includes treating, preventing, ameliorating, or inhibiting an injury or disease related condition and/or a symptom of an injury or disease related condition.

An "effective amount" generally means an amount which provides the desired local or systemic effect, such as enhanced performance. For example, an effective dose is an amount sufficient to affect a beneficial or desired clinical result. Said dose could be administered in one or more administrations and could include any preselected amount of cells. The precise determination of what would be considered an effective dose may be based on factors individual to each subject, including their size, age, injury and/or disease or being treated and amount of time since the injury occurred or the disease began. One skilled in the art, specifically a physician, would be able to determine the number of cells that would constitute an effective dose.

"Co-administer" can include simultaneous and/or sequential administration of two or more agents.

The terms "comprises," "comprising," and the like can have the meaning ascribed to them in U.S. Patent Law and can mean "includes," "including" and the like. As used herein, "including" or "includes" or the like means including, without limitation.

Embodiments

The present disclosure relates generally to the field of stem cell biology, more specifically the directed differentiation of stem cells, such as human pluripotent stem cells (hPSCs) or multipotent stem cells, including embryonic stem cells (ESC), somatic (e.g., adult) stem cells, and induced pluripotent stem cells (iPSC) using novel culture conditions. Specifically, methods are provided for obtaining anterior ectoderm and neuromesoderm. Further, anterior ectoderm obtained using methods of the present inventions can be used in further patterning toward progenitors eventually giving rise to structures of the epidermis, neural tube, and neural crest. Further, neuromesoderm obtained using methods of the present inventions can be used in further patterning toward progenitors eventually giving rise to structures of the epidermis, neural tube, neural crest, and somite.

The present disclosure is related to methods of obtaining populations of neural progenitor cells derived from PSCs, in particular for obtaining anterior ectoderm. Specifically, methods of the present inventions induce anterior ectoderm in PSCs for use in further patterning toward progenitors eventually giving rise to structures of the epidermis, neural tube, and neural crest.

The present invention is related to methods of obtaining populations of posterior neural progenitor cells and posterior mesoderm progenitor cells derived from PSCs, in particular for obtaining neuromesoderm. Specifically, methods of the present inventions induce neuromesoderm in PSCs for use in further patterning toward progenitors eventually giving rise to structures of the epidermis, neural tube, neural crest, and somite.

Stem Cells

The method functions across a broad range of undifferentiated stem cell lines, and is simple to execute. The stem cells for use in the compositions, methods and kits provided herein can be any vertebrate stem cell, including human.

The stem cells include, but are not limited to, embryonic stem cells (including human embryonic stem cells (hESC)), somatic stem cells (e.g., human), and induced pluripotent stem cells (iPSC (e.g., human)).

Embryonic stem cells are pluripotent stem cells derived from the inner cell mass of a blastocyst, an early-stage preimplantation embryo. Human embryos reach the blastocyst stage 4-5 days post fertilization, at which time they consist of 50-150 cells.

Somatic stem cells include adult stem cells which are undifferentiated cells, found throughout the body alter development that multiply by cell division to replenish dying cells and regenerate damaged tissues.

Induced pluripotent stem cells (also known as iPS cells or iPSCs) are a type of pluripotent stem cell that can be generated directly from adult cells. iPSCs are typically derived by introducing products of specific sets of pluripotency-associated genes, or "reprogramming factors," into a given cell type. The original set of reprogramming factors are the transcription factors Oct4 (Pou5f1), Sox2, cMyc, and Klf4. While this combination is most conventional in producing iPSCs, each of the factors can be functionally replaced by related transcription factors, miRNAs, small molecules, or even non-related genes such as lineage specifiers (e.g., nanog, LIN28, Glis1).

Stem cells, and those cells differentiated therefrom, can be expanded and further differentiated and/or frozen by way of media and cell culturing methods available to an art worker.

Inhibitors, Cytokines and Other Factors

Inhibitors of use in the methods, compositions and kits of the invention include, but are not limited to, one or more inhibitors of ALK 2/3 signaling; one or more inhibitors of ERK signaling, one or more inhibitors of ALK 4/5/7 signaling, one or more inhibitors of MAPK/ERK Kinase (MEK) 1/2 and/or one or more inhibitors of Fibroblast Growth Factors Receptors (FGF) 1, 2, 3 and/or 4, including blocking antibodies, one or more inhibitors of GSK3b to activate WNT signaling or protein ligands to WNT receptors Frizzled, one or more activators of WNT.

Such inhibitors/activators include, but are not limited to, a disulfide-linked homodimer of Noggin (such as mouse (accession numbers NM_008711 (mRNA), NP_032737.1 (protein) and NP_032737 (protein)), human (accession numbers NM_005450 (mRNA) and NP_005441 (protein)), rat, and/or xenopus (rat accession number NP_037122.1 (protein), xenopus accession number NP_001165369 (protein) Noggin); Dorsomorphin (6-[4-(2-Piperidin-1-ylethoxy)phenyl]-3-pyridin-4-ylpyrazolo[1,5-a]pyrimidine: Sigma-Aldrich); LDN-193189 (4-[6-[4-(1-Piperazinyl)phenyl]pyrazolo[1,5-a]pyrimidin-3-yl]-quinoline hydrochloride; Sigma-Aldrich): BGJ398 (3-(2,6-dichloro-3,5-dimethoxyphenyl)-1-(6-(4-(4-ethylpiperazin-1-yl)-phenylamino)pyrimidin-4-yl)-1-methylurea, PubChem CID 53235510): PD0325901 (N-[(2R)-2,3-Dihydroxypropoxy]-3,4-difluoro-2-[(2-fluoro-4-iodophenyl)amino]-benzamide; Sigma-Aldrich), A8301 (3-(6-methylpyridin-2-yl)-N-phenyl-4-quinolin-4-ylpyrazole-1-carbothioamidePubChem CID 16218924); SB431542 (4-(5-Benzol[1,3]dioxol-5-yl-4-pyridine-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate; Sigma-Aldrich); SU5402 (3-[4-Methyl-2-(2-oxo-1,2-dihydro-indol-3-ylidenemethyl)-1H-pyrrol-3-yl]-propionic acid, PF-02969207; Sigma-Aldrich), CHIR99021, BIO (both are GSK3-beta inhibitors that activate WNT pathway and can be purchased at Caymanchem, Tocris) and derivatives thereof and combinations thereof.

Further inhibitors/activators and details regarding them can be found in FIG. 29.

With regards to activator or inhibitors that are protein, can also include one or more conservative amino acid substitutions. As used herein, the term "conservative amino acid substitution" is defined herein as an amino acid exchange within one of the following five groups:

I. Small aliphatic, nonpolar or slightly polar residues:
Ala, Ser, Thr, Pro, Gly.
II. Polar, negatively charged residues and their amides:
Asp, Asn, Glu, Gin:
III. Polar, positively charged residues:
His, Arg, Lys;
IV. Large, aliphatic, nonpolar residues:
Met Leu, Ile, Val, Cys
V. Large, aromatic residues:
Phe, Tyr, Trp Also are included fragments of the polypeptides such as "biologically active fragments" or "bioactive fragment" of the polypeptides which encompasses natural or synthetic portions of the full length protein that are capable of specific binding to their natural ligand or of performing the function of the protein.

i. Amino Acid Substitutions and Amino Acid/Peptide Modifications

In certain embodiments, the disclosed methods and compositions may involve preparing peptides with one or more substituted amino acid residues, such as conservative substitutions as discussed above. For example, in various embodiments, the structural, physical and/or therapeutic characteristics of peptide sequences may be optimized by replacing one or more amino acid residues.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain. e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gin, asn, lys; Asn (N) his, asp, lys, arg, gln; Asp (D) asn, glu; Cys (C) ala, ser, Gin (Q) glu, asn; Glu (E) gin, asp; Gly (G) ala; His (H) asn, gn, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr, Pro (P) ala; Ser (S), thr; Thr (T) ser; Trp (W) phe, tyr, Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr, Ser and Ala; Thr and Ala; Ala and Gly; Ile and Val; Val and Leu; Leu and Ile; Leu and Met; Phe and Tyr; Tyr and Tip. (See, e.g., PROWL Rockefeller University website). For solvent exposed residues, conservative substitutions would include: Asp and Asn; Asp and Glu; Glu and Gin; Glu and Ala; Gly and Asn; Ala and Pro; Ala and Gly; Ala and Ser; Ala and Lys; Ser and Thr: Lys and Arg; Val and Leu; Leu and Ile; lie and Val; Phe and Tyr. (ld.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Peptides described herein can also include non-natural amino acids are non-proteinogenic amino acids, such as, β-amino acids (β3 and β2), homo-amino acids, proline and pyruvic acid derivatives, 3-substituted Alanine derivatives, glycine derivatives, ring-substituted phenylalanine and tyrosine derivatives, linear core amino acids, N-methyl amino acids, heavy atom containing amino acids and/or L- and D-amino acids (in protected or unprotected forms). Such non-natural amino acids can be used to, for example, increase half-life, activity and/or solubility. The peptides can also include probes and/or tags.

Possible chemical modifications of the protein moieties of the present invention also include derivitization with polyethylene glycol (PEG) or other polymers (such as dextran) to extend time of residence in the circulatory system and reduce immunogenicity, according to well-known methods (See for example, Lisi, et al., Applied Biochem. 4:19 (1982); Beauchamp, et al., Anal Biochem. 131:25 (1982); and Goodson, et al., Bio/Technology 8:343 (1990)).

It may also be advantageous to add to the amino- or carboxy-terminus of the peptide chemical moieties or additional (modified or D–) amino acids in order to increase the stability and/or decrease the biodegradability of the peptide.

A peptide bond mimetic of the invention includes peptide backbone modifications well known to those skilled in the art. Such modifications include modifications of the amide nitrogen, the alpha carbon, amide carbonyl, complete replacement of the amide bond, extensions, deletions, or backbone cross-links. See, generally, Spatola, Chemistry and Biochemistry of Amino Acids, Peptides and Proteins, Vol. VII (Weinstein ed., 1983). Several peptide backbone modifications are known and can be used in the practice of the invention.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include C1-C5 branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—NH2), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without effect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

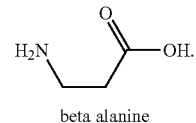

beta alanine

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Optimized concentrations used in practice are 500 nM LDN193189, 500 nM A8301 or 10 uM SB35432, 100 nM BGJ398 or 1 uM PD PD0325901, 15 uM SU5402. LDN193189 is functional from 10 nM to 1 uM, A8301 10 nM to 10 uM, SB35432 1 uM to 50 uM, BGJ398 10 nM to 5 uM, PD0325901 100 nM to 5 uM, SU5402 1 uM to 30 uM, CHIR99021 1 mM to 6 mM. The majority of cells have established PAX6/SOX1 or SOX2/T expression following 12-18 hours of exposure. 48 hours of exposure or more causes cell death.

Differentiated Cell Types

In one embodiment, said the stem cells are differentiated to anterior ectoderm. In one embodiment, following the differentiation methods disclosed herein, the differentiated cell (ectoderm) is at least 10% up to 100% of said population of cultured cells. Those skilled in the art can readily determine the percentage of ectoderm cells in a population using various well-known methods, such as fluorescence activated cell sorting (FACS). Ranges in populations comprising ectoderm include about 50-55%, 55-60%, and 65-70%, including about 70-75%, 75-80%, 80-85%; and about 85-90%, 90-95%, and 95-100% of ectoderm cells produced by the methods described herein. However, populations with lower purity can also be useful, such as about 10-25%, 25-30%, 30-35%, 35-40%, 40-45% and 45-50%. The concentration of ectoderm cells can be determined according to the gene expression profile within a population.

Anterior ectoderm made by the methods provided herein can be further differentiated into cells selected from the group consisting of central and/or peripheral nervous system progenitor cells, patternable progenitor cells, neurons (4,5) (expressing NeuN/beta-III-tubulin) and glia (26)(expressing OLIG2/SOX10); and derivatives of the epidermis (27) (expressing cytokeratin 14 and p63) and neural crest (11) (expressing Pax3/SOX10/SOX9/p75/HNK). Furthermore, these populations can be induced to form neuromesoderm progenitors (30) (expressing SOX2/T) capable of forming surface ectoderm, neural crest stem cells, spinal neuroepithelium, spinal cord (28), and somite (expressing TBX6), which can further be differentiated into muscle progenitors (Myogenin/PAX3/7), chondrocyte progenitors, fibroblast progenitors, and osteoblast progenitors.

In one embodiment, said stem cells are differentiated to neuromesoderm. In one embodiment, following the differentiation methods disclosed herein, the differentiated cell (neuromesoderm) is at least 10% up to 100% of said population of cultured cells. Those skilled in the art can readily determine the percentage of neuromesoderm in a population using various well-known methods, such as fluorescence activated cell sorting (FACS). Ranges in populations comprising neuromesoderm include about 50-55%, 55-60%, and 65-70%, including about 70-75%, 75-80%, 80-85%; and about 85-90%, 90-95%, and 95-100% of ectoderm cells produced by the methods described herein. However, populations with lower purity can also be useful, such as about 10-25%, 25-30%, 30-35%, 35-40%, 40-45% and 45-50%. The concentration of neuromesoderm can be determined according to the gene expression profile within a population.

Neuromesoderm made by the methods provided herein can be further differentiated into cells selected from the group consisting of central and peripheral nervous system progenitor cells, patternable progenitor cells, neurons (4, 5) (expressing NeuN/beta-II-tubulin) and glia (26) (expressing OLIG2/SOX10); and derivatives of the epidermis (27) (expressing cytokeratin 14 and p63) and neural crest (11) (expressing PAX3/SOX10/SOX9/p75/HNK). Furthermore, these populations can be induced to form somite tissue (29)(expressing TBX6), which can further be differentiated into muscle progenitors (Myogenin/PAX3/7), chondrocyte progenitors, fibroblast progenitors, and osteoblast progenitors.

Cell Culture

During differentiation the cells of the invention can be cultured in culture medium that is well established in the art and commercially available from the American Type Culture Collection (ATCC). Such media include, but are not limited to, Dulbecco's Modified Eagle's Medium (DMEM), DMEM F12 medium, Eagle's Minimum Essential Medium. F-12K medium, Iscove's Modified Dulbecco's Medium, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements, and bovine embryonic fluid. It is understood that sera can be heat-inactivated at 55-65° C. if deemed necessary to inactivate components of the complement cascade. Modulation of serum concentrations, or withdrawal of serum from the culture medium can also be used to promote survival of one or more desired cell types. In one embodiment, the endodermal progenitor cells are cultured in the presence of FBS/or serum specific for the species cell type. For example, stem cells can be isolated and/or expanded with total serum (e.g., FBS) concentrations of about 0.5% to about 5% or greater including about 5% to about 15%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution (HBSS), Earle's Salt Solution, anti-oxidant supplements, MCDB-201 supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cysteine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone□), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Also contemplated is the use of feeder cell layers. Feeder cells are used to support the growth of fastidious cultured cells. Feeder cells are normal cells that have been inactivated by □-irradiation. In culture, the feeder layer serves as a basal layer for other cells and supplies cellular factors without further growth or division of their own (Lim and Bodnar 2002). Examples of feeder layer cells typically used with liver cell cultures are hepatocytes and embryonic fibroblasts (Suzuki, A. et al. 2000), but can be any post-mitotic cell that is capable of supplying cellular components and factors that are advantageous in allowing optimal growth, viability, and expansion of endodermal progenitor cells. In some cases, feeder cell layers are not needed to keep cells in an undifferentiated, proliferative state, as leukemia inhibitory factor (LIF) has anti-differentiation properties. Often, supplementation of a defined concentration of LIF is all that is necessary to maintain cells in an undifferentiated state.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel®, thrombospondin, and/or vitronectin.

The maintenance conditions of cells can also contain cellular factors that allow cells to remain in an undifferentiated form. It is apparent to those skilled in the art that supplements that allow the cell to self-renew (e.g., to produce replicate daughter cells having differentiation potential that is identical to those from which they arose; a similar term used in this context is "proliferation"), but not differentiate should be removed from the culture medium prior to differentiation. It is also apparent that not all cells will require these factors. In fact, these factors may elicit unwanted effects, depending on the cell type.

Myogenic progenitor cells can be selected based on the markers (gene and/or protein) described herein. Accordingly, positive selection methods can be used, either alone or together with the methods described above, to identify and/or isolate the cells of the invention. Methods of positive selection can include visual selection, using microscopy and/or other means of detection, including, but not limited to, immunoblotting, immunofluorescence, and/or enzyme-linked immunosorbent assay. Other methods of positive selection can also include, but are not limited to, additional selective culture techniques (e.g., variable cell densities or amounts of $CO_2$), flow cytometry, RT-PCR, and/or microchip-based methods of cell separation.

Administer Cells

The cells prepared as described herein can be administered to a subject by a variety of methods available to the art, including but not limited to localized injection, catheter administration, systemic injection, intraperitoneal injection, parenteral administration, intra-arterial injection, intravenous injection, intraventricular infusion, intraplacental injection, intrauterine injection, surgical intramyocardial injection, transendocardial injection, transvascular injection, intracoronary injection, transvascular injection, intramuscular injection, surgical injection into a tissue of interest or via direct application to tissue surfaces (e.g., during surgery or on a wound).

Intravenous injection is the simplest method of cell administration; however a greater degree of dependence on homing of the stem cells is required for them to reach the tissue of interest. "Homing" of the cells to the injured tissues would concentrate the implanted cells in an environment favorable to their growth and function. Pre-treatment of a patient with cytokine(s) to promote homing is another alternative contemplated in the methods of the present invention. Where homing signals may be less intense, injection of the cells directly into the muscle can produce a more favorable outcome. Certain cytokines (e.g., cellular factors that induce or enhance cellular movement, such as homing of stem cells, progenitor cells or differentiated cells) can enhance the migration of cells or their differentiated counterparts to the site of damaged muscle tissue. Cytokines include, but are not limited to, stromal cell derived factor-1 (SDF-1), stem cell factor (SCF) and granulocyte-colony stimulating factor (G-CSF). Cytokines also include any which promote the expression of endothelial adhesion molecules, such as ICAMs, VCAMs, and others, which facilitate the homing process.

Viability of newly forming tissues can be enhanced by angiogenesis. Factors promoting angiogenesis include but are not limited to VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol, nicotinic amide.

Factors that decrease apoptosis can also promote the formation of new tissue, such as muscle. Factors that decrease apoptosis include but are not limited to β-blockers, angiotensin-converting enzyme inhibitors (ACE inhibitors), AKT, HIF, carvedilol, angiotensin 11 type 1 receptor antagonists, caspase inhibitors, cariporide, and eniporide.

Exogenous factors (e.g., cytokines, differentiation factors (e.g., cellular factors, such as growth factors or angiogenic factors that induce lineage commitment), angiogenesis factors and anti-apoptosis factors) can be administered prior to, after or concomitantly with the skeletal muscle cells. Doses for administration(s) are variable and may include an initial administration followed by subsequent administrations.

In current human studies of autologous mononuclear bone marrow cells, empirical doses ranging from 1 to $4 \times 10^7$ cells have been used. However, different scenarios may require optimization of the amount of cells injected into a tissue of interest. Thus, the quantity of cells to be administered will vary for the subject being treated. In one embodiment, between $10^4$ to $10^8$, more preferably $10^5$ to $10^7$, and most preferably, $3 \times 10^7$ stem cells and optionally, 50 to 500 µg/kg per day of a cytokine can be administered to a human subject. For local muscle placement/injection, as few as 40,000 cells can be administered. However, the precise determination of what would be considered an effective dose may be based on factors individual to each patient, including their size, age, disease or injury, size damage, amount of time since the damage occurred and factors associated with the mode of delivery (direct injection—lower doses, intravenous—higher doses).

The skilled artisan can readily determine the amount of cells and optional additives, vehicles, and/or carrier in compositions and to be administered in methods of the invention. Typically, any additives (in addition to the active cell(s) and/or cytokine(s)) are present in an amount of 0.001 to 50 wt % solution in phosphate buffered saline, and the active ingredient is present in the order of micrograms to milligrams, such as about 0.0001 to about 5 wt %, including about 0.0001 to about 1 wt %, including about 0.0001 to about 0.05 wt % or about 0.001 to about 20 wt %, including about 0.01 to about 10 wt %, and including about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, the cells can be administered initially, and thereafter maintained by further administration of the cells. For instance, the cells can be administered by one method of injection, and thereafter further administered by a different or the same type of method. For example, cells can be administered by surgical injection to bring muscle function to a suitable level. The patient's levels can then be maintained, for example, by intravenous injection, although other forms of administration, dependent upon the patient's condition, can be used.

It is noted that human subjects are treated generally longer than the canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising the cells of the invention include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the cells as described in the present invention.

Compositions can be administered in dosages and by techniques available to those skilled in the medical and veterinary arts taking into consideration such factors as the age, sex, weight, and condition of the particular patient, and the composition form used for administration (e.g., solid vs. liquid).

Suitable regimes for initial administration and further doses or for sequential administrations also are variable, may include an initial administration followed by subsequent administrations.

The following examples are intended to further illustrate certain embodiments of the invention and will not limit the scope of the invention in any way.

EXAMPLES

Example 1

Materials Methods

Human Induced Pluripotent Stem Cell (hiPSC) Culture

Prior to passaging, a recombinant human vitronectin stock solution (500 ug/mL, Peprotech AF-140-09, Rocky Hill, N.J., USA) was diluted 1:100 in DPBS+/+ (ThermoFisher Scientific cat #14040-133, Waltham, Mass., USA) and used to coat 9.6 cm² tissue-culture treated wells (Fischer Scientific, Hampton, N.H.) for one hour at room temperature. hPSCs were washed once with 1 mL hypertonic citrate buffer (11) or equivalent and then incubated with 1 mL hypertonic citrate buffer (11) at 37° C. for 6 minutes until colony detachment occurred. The colonies were collected and processed into 25-50 cell fragments by trituration and the dissociation quenched with 5 mL Essential 6 Medium (ThermoFisher Scientific A1516401, Waltham, Mass., USA). Suspensions were collected into 15 mL conical tubes and centrifuged for 1 minute at 200×G. Supernatants were aspirated and pellets resuspended into 1.2 mL Essential 6 Medium (ThermoFisher Scientific A2858501, Waltham, Mass., USA) assuming a 1:6 split ratio. 0.2 mL cultures were seeded onto rhVTN-coated wells containing Essential 8 Medium. Cultures were maintained in Essential 8 Medium with daily media changes and passaged every 3 days.

Accelerated Differentiation of hiPSCs into Neuroepithelium

Differentiation medium consisting of Essential 6 supplemented with LDN-193189 HCl (500 nM, Selleckchem cat #S7507, Houston, Tex. USA) and BGJ398 (100 nM Selleckchem cat #S2183 Houston, Tex. USA) was combined and distributed 2 mL per vitronectin-coated well of a 6-well plate. hPSCs were dissociated into small clumps (25-50 cells per clump) as indicated above. 0.2 to 0.4 mL cultures were seeded onto rhVTN-coated wells containing differentiation medium.

Accelerated Production of Midbrain Floorplate Neuroepithelium

Day-one differentiated neuroepithelial cells were treated with Essential 6 supplemented with CHIR 99021 (1400 nM, Tocris cat #4423, Bristol UK), SAG (250 nM, CaymanChem cat #11914, Ann Arbor, Mich. USA), and FGF2 (100 ng/mL, Peprotech, Rocky Hill N.J.) for 24 to 48 hours. Day 2 or Day 3 midbrain progenitors were treated with Essential 6 supplemented with wnt-c59 (250 nM, CaymanChem cat #16644), SAG (250 nM, CaymanChem cat #912545-86-9), and BGJ398 (100 nM, CaymanChem cat #19157) for 24 hours to create OTX2/LMX1A/FOXA2-positive cells within 24 to 48 hours.

Accelerated Production of Neuromesoderm Progenitors

Differentiation medium consisting of Essential 6 supplemented with LDN-193189 HCl (500 nM, Selleckchem cat #S7507, Houston, Tex. USA), BGJ398 (100 nM Selleckchem cat #S2183 Houston, and TX USA), and CHIR 99021 (3 uM, Tocris cat #4423, Bristol UK) was combined and distributed 2 mL per vitronectin-coated well of a 6-well plate. hPSCs were dissociated into small clumps (25-50 cells per clump) as indicated above. 0.2 to 0.4 mL cultures were seeded onto rhVTN-coated wells containing differentiation medium.

Accelerated Production of Spinal Neuroepithelium

Day-one Neuromesoderm progenitors were exposed to differentiation medium consisting of Essential 6 supplemented with CHIR 99021 (3 uM, Tocris cat #4423, Bristol UK) and FGF-Basic TS™ (20 ng/mL, Humanzyme cat #HZ-1286, Chicago, Ill. USA) for 24 hours. This day-two neuromesoderm was further exposed to differentiation medium consisting of Essential 6 supplemented with BGJ398 (100 nM Selleckchem cat #52183 Houston, Tex. USA) to create a day-three population of PAX3/SOX1/HOXB4-positive neuroepithelial cells.

Accelerated Production of Spinal Floorplate Neuroepithelium

Day-2 spinal neuromesoderm progenitors were exposed to differentiation medium consisting of Essential 6 supplemented with SAG (500 nM), BGJ398 (100 nM), and WNT-c59 (250 nM) for 24 hours to create a population of SOX1+/FOXA2+/NKX2.2+/HOXB4+ cells between days 3 and 4.

Results

Development of the human central nervous system can be modeled in vitro through the differentiation of human pluripotent stem cells (hPSCs). Initial stages of hPSC differentiation create the neuroectoderm (NE) and mesendoderm germ layers, which eventually give rise to all tissues in the adult body. While mesendoderm can be rapidly induced in vitro through WNT activation, NE forms relatively slowly under passive conditions. This NE defaults to a dorsal-anterior phenotype, while formation of posterior NE requires either caudal transformation of anterior NE, or direct induction from hPSCs through a neuromesoderm (NM) intermediate. The in vitro formation and rostral-caudal positioning of hPSC-derived NE, therefore, requires widely disparate and prolonged culture conditions. Herein it is demonstrated that region-specific production of NE can be accelerated through antagonism of fibroblast growth factor (FGF) signaling. It was found that formation of both anterior neural plate and posterior NM can be produced from hPSCs within 24 hours under low and high WNT signaling, respectively, simultaneous with antagonism of activin-like kinases receptors 2/3 and fibroblast growth factor receptors 1/2/3/4.

The data clarify the controversial role of FGF as it pertains to the formation of NE lineages by providing a unified mechanism for rapid, direct access to anterior and posterior fates. This strategy can serve as a useful method for production of hPSC-derived neural cell types of the brain and spinal cord in accelerated fashion, and points to a role for growth factor signaling in regulating developmental pacing, antagonism of which can be leveraged to abbreviate in vitro differentiation protocols.

It has been shown that the undifferentiated status of hPSCs is maintained by ERK and SMAD signaling stimulated by exogenous provision of FGF and TGFb1. While the modulation of SMAD pathways as it relates to the initial differentiation of hPSCs has been well described, little information has been disseminated regarding the modulation of ERK signaling for similar purposes. As such, the effects of ERK inhibition were investigated, specifically during the process of neurulation under defined conditions.

Conditions were assayed in which the ERK pathway was inhibited at both receptor and downstream intracellular effector levels. The VEGFR2/FGFR2 inhibitor SU5402 was compounded with previously known neurulation conditions containing the ALK2/3 receptor antagonist LDN 193189 and the ALK 4/5/7 receptor antagonist A8-30-1 to observe their combined effect on undifferentiated pluripotent stem cells. Following 24-hours incubation, cultures adopted subtle morphological changes under phase-contrast microscopy, including an increased nuclear-to-cytoplasmic ratio. Continued culture under these conditions for an additional 48 hours resulted in cell death (data not shown).

24-hour differentiating cultures were analyzed prior to cell death for various transcription factors associated with pluripotency and NE formation. Compared to undifferentiated control cultures, SU5402-treated cultures displayed reduced NANOG positivity, suggesting the early stages of pluripotential exit. SOX2, common to both hPSCs and NE, was maintained. Meanwhile, SU5402-treated cultures displayed SOX1-positivity in greater than 90% of cells, demonstrating early stage NE formation (FIG. 3).

Additional hPSC lines were assayed in the same manner using the three-inhibitor cocktail and differential responses were found in terms of SOX1-immunoreactivity. It was believed that SU5402 was incompletely suppressing FGF and VEGF signaling for some lines due to its restricted specificity for FGFR2 and VEGFR2, leading to incomplete acquisition of SOX1-immunoreactivity. The pan-FGFR and VEGFR-inhibitors BGJ398 and Axitinib targeting FGFR1, FGFR3, FGFR2, FGFR4, VEGFR1, VEGFR2, VEGFR3, and VEGFR4 were used in separate conditions and it was found that while Axitinib induced SOX1-immunoreactivity at only relatively high concentrations, even low concentrations of BGJ398 induced SOX11 completely for all lines tested. These data indicated that the neuralizing effects of SU5402 were largely attributable to its functions as an FGFR inhibitor.

Single-molecule subtractions from the inhibitor cocktail demonstrated that co-treatment with the combination of BGJ398 and LDN 193189 was sufficient to create a majority population of SOX1-immunopositive cells, whereas any other two-inhibitor combination failed to induce SOX1-immunoreactivity following 24 hours. Single-inhibitor conditions likewise failed to induce SOX1-immunoreactivity (FIG. 7).

To better understand the downstream mechanisms by which BGJ398 exerted its function, inhibitors to various components of the FGF signaling cascade were assayed. Whereas SB239063, a small molecule inhibitor to p38, had no effect under standard neuralizing conditions (data not shown), the MEK inhibitor PD0325901 performed similarly to BGJ398 to promote formation of NE (FIG. 4A-C).

To confirm that the NE derived in the system provided herein maintains similar developmental flexibility to that derived by others, NE produced was further patterned (differentiated) toward various regions along the rostral-caudal neuraxis. The rostral-caudal identity of the neural plate can be described by a transcription factor code that delineates anatomical subdivisions between the telencephalon, diencephalon, mesencephalon, metencephalon, and spinal cord. Telencephalic structures are known to express the transcription factor combination SOX1+/FOXG1+/OTX2+/PAX5−, while diencephalic, mesencephalic, and metencephalic structures express the combinations SOX1+/FOXG1−/OTX2+/PAX5−/HOXB4−, SOX1+/FOXG1−/OTX2+/PAX5+/HOXB4−, SOX1+/FOXG1−/OTX2−/PAX5+/HOXB4−, and SOX1+/FOXG1−/OTX2−/PAX5−/HOXB4+, respectively. The midbrain structure is of interest to researchers for its ability to produce dopaminergic neurons, which is of significance especially to Parkinson researchers. Adapting previously described conditions that modulate WNT and FGF signaling, the day-1 neural plate generated in the system described herein was able to produce day-3 neuroepithelium expressing the transcription factor code SOX1+/FOXG1−/OTX2+/PAX5+/HOXB4− (FIG. 11). With appropriate rostral-caudal identity established, these cultures were exposed to sonic hedgehog (SHH) signaling to promote a day-4 ventral floorplate phenotype as demonstrated by FOXA2 immunopositivity (FIG. 11). Others have shown that these SOX1+/OTX2+/PAX5+/FOXA2+ neuroepithelial cells will further differentiate into dopaminergic neural progenitors under appropriate conditions (PMID: 26015536).

Controversy currently exists surrounding the origin of the most caudal segments of the central nervous system that include the spinal cord. In vitro conditions for generating spinal cord tissue have traditionally relied upon the formation of anterior neural plate expressing SOX1+/FOXG1+/OTX2+/PAX5−/HOXB4− that is caudalized with factors such as FGF, WNT, and retinoic acid to create SOX1+/FOXG1−/OTX2−/PAX5−/HOXB4+ positive cervical spinal cord tissue. Alternatively, it has been suggested that the spinal cord originates from a neuromesodermal structure whereby a SOX1−/SOX2+/T+/TBX6−/HOXB4− population is created directly from hPSCs that can be maintained as caudalized SOX1−/SOX2−/T+/TBX6−/HOXB4+ neuromesoderm, or further differentiated into either SOX1−/SOX2−/T+/TBX+/HOXB4+ somite tissue or SOX1+/SOX2+/T−/TBX6−/HOXB4+ spinal tissue. The day-1 neuroectoderm was exposed to combinations of caudalizing factors and it was found that high levels of WNT signaling using the agonist CHIR99021 was sufficient to induce a SOX1−/SOX2+/T+/TBX6−/HOXB4− population by day 2, however additional FGF signaling maintained higher purity and reduced inter-line variation (FIG. 13). An additional 24 hours of WNT/FGF signaling converted this population into SOX1−/SOX2+/T+/TBX6−/HOXB4+ cervical-level neuromesoderm (FIG. 13).

The previous scenario utilized a neuroectoderm intermediate for the generation of neuromesoderm. Because it has been shown that neuromesoderm can be derived directly from hPSCs, high levels of WNT signaling were incorporated into the day-1 neuroectoderm conditions to investigate whether this could induce neuromesoderm directly. Undifferentiated cultures exposed to LDN 193189, BGJ 398, and CHIR 99021 were shown to adopt a SOX1−/SOX2+/T+/TBX6−/HOXB4− immunophenotype within 24 hours. Given an additional 24 hours incubation with CHIR 99021, these day-2 cultures upregulated the HOXB4 transcription factor to create a population of SOX1−/SOX2+/T+/TBX6−/HOXB4+ neuromesoderm (FIG. 12).

It has been shown that retinoic acid signaling is needed to convert neuromesoderm into spinal cord neuroepithelium. The day-2 neuromesoderm was exposed to various concentrations of retinoic acid, but it was found that this created a mixed population comprised of SOX1+/SOX2+/T−/TBX6−/HOXB4+ spinal neuroepithelium and SOX1−/SOX2+/T+/TBX6+/HOXB4+ somite tissue (not shown). It has been shown that retinoids exert multiple simultaneous functions in the developing spinal cord, inhibiting FGF signaling, while activating both WNT and SHH signaling. These independent functions of retinoic acid were dissected using modulators of the aforementioned pathways and it was discovered that while day-3 FGF withdrawal created a mixture of both neuromesoderm and cervical spinal tissue without contaminating somite tissue, actively inhibited FGF signaling with BGJ 398 created a pure population of spinal neuroepithelium lacking evidence of neuromesoderm or somite tissues (FIG. 15). This spinal neuroepithelium was further characterized with respect to additional markers and discovered that it was partially PAX3-positive, an early spinal neural plate marker. The day-3 conditions were optimized to maximize PAX3 and it was discovered that moderate WNT signaling was needed in addition to FGF inhibition to derive a pure population of cervical neural plate epithelium homogeneously expression PAX3 (FIG. 18). To investigate the dorso-ventral patterning competency of these retinoid-independent spinal neuroepithelial cells, the day-3 cultures were exposed to SHH signaling. This produced a PAX6−/SOX1+/NKX2.2+/FOXA2+ population, indicating a floorplate phenotype. A subset of these cells co-expressed OLIG2, an additional ventral marker.

Together, these two major findings illustrate a flexible system that allows one access to either hPSC-derived anterior or posterior neural fates competent for dorso-ventral patterning with unprecedented speed and simplicity, and aims to unify what are currently two distinct fields of study reliant on widely disparate culture conditions. These findings improve on current technology, especially with respect to timing in-vitro. While techniques for the production of neuroepithelium have seen substantial refinement since the discipline was founded, the minimum seven days required for neuroepithelial conversion has stood as an absolute developmental speed limit in vitro. Central to the methodology described herein is the inclusion of an FGF inhibitor to force this conversion, which has been previously interrogated without success. Those studies, however, relied upon alternative markers to monitor neuroepithelial conversion, utilized chemistries that have demonstrated here to be ineffectual, maintained their undifferentiated hPSCs in undefined and chemically complex conditions, and forced conversion during aggregation. Differences such as these are important and have been shown to influence differentiation trajectory.

The neuromesoderm tissue itself is a nascent field of study with convincing, yet limited, data behind it. Colinear hox activation was not explored as has been previously described, but instead focused with detail on the neuromesoderm-to-neuroepithelial fate transition. Of interest is that FGFR antagonism was instrumental to both hPSC and neuromesoderm-to-neuroepithial transitions, reinforcing the role of FGF signaling cascades in maintaining stemness, and suggesting this to be a generalized strategy for aborting self-renewal programs.

Perhaps most interesting is the day-4 spinal floorplate neuroepithelium derived in the disclosed system. The in vitro production of such a structure from hPSCs has not yet been thoroughly described in the literature. Numerous differentiation protocols designed to create hPSC-derived spinal oligodendrocyte progenitor cells (OPCs) rely on OLIG2+/NKX2.2+ intermediates. Current dogma indicates that spinal OPCs originate from the OLIG2+/NKX2.2− pMN domain in a retinoid-dependent manner, which is then converted into a pMN* OLIG2+/NKX2.2+ population through continued SHH signaling. It may be possible that OPCs originate from a FOXA2+/NKX2.2+/OLIG2− floorplate intermediate that later acquires a FOXA2+/NKX2.2+/OLIG2+ phenotype retinoid-independently, as we have described here. This may partially explain the difficulty in producing spinal OPCs from hPSCs using currently available protocols, as they all rely on retinoid-dependent caudalization of anterior neural plate rather than retinoid-independent neuromesoderm derived spinal floor plate.

Example 2

Introduction

Damage to the spinal cord after injury can result in the death of spinal neurons and glia at the site of injury. This damage includes the complete loss of neurons that reside at the site of injury, but also severs axons descending from the cerebral motor cortex through the injury responsible for controlling voluntary movement. Damage to these corticospinal neurons will effect some motor function directly above the injury, but more importantly can lead to complete loss of all motor function below the injury. Neural transplantation into the site of spinal cord injury has been shown to improve functional recovery in animal models of spinal cord injury, and have reached early stage clinical trials in patients. However, patient outcomes from these trials have been mixed, suggesting improvements must be made to understand the precise cellular phenotype of grafted tissue. The premise for transplantation of neuronal cells into the damaged spinal cord is the expectation that lost neuronal connections in the host can be repaired by the neuronal graft. The graft may also provide trophic support and regenerative cues to the existing host neurons. However, these treatment paradigms often utilize poorly characterized tissue that ignores the complex developmental neuroanatomy of the spine, which may influence how individual patients with differing injuries will respond to treatment.

Figure 24D:
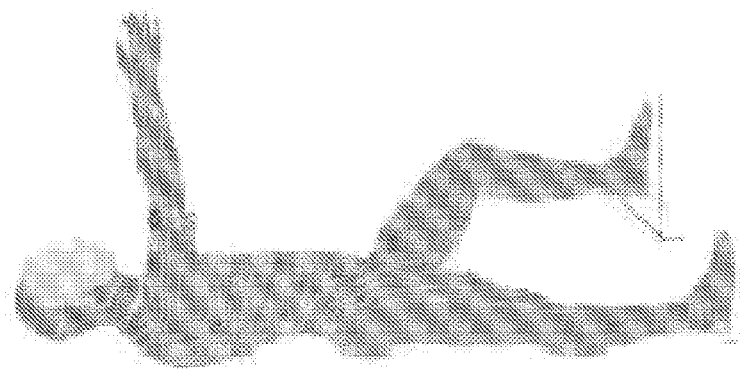
Figure 24C:
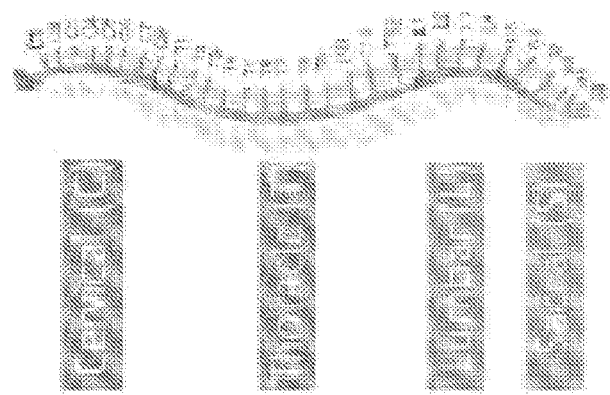
Figure 24B:
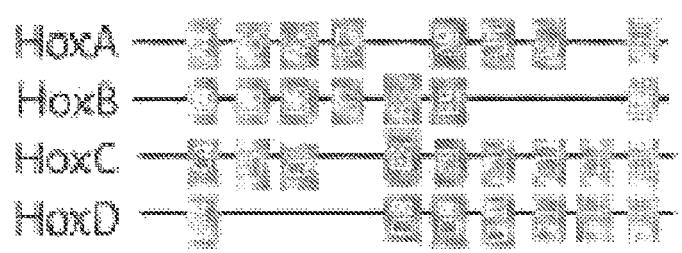
Figure 24A:
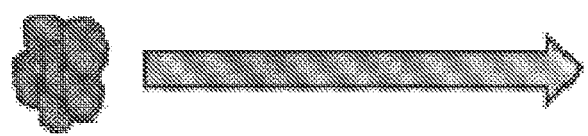

During embryogenesis, the spinal cord elongates from the base of the hindbrain "neck-to-tail" utilizing a proliferative zone consisting of neuromesoderm progenitors (NMPs) (FIG. 24A). As this growth occurs, the spine is segmented in sequential fashion through oscillation of stemness factors resulting in what is termed collinear HOX gene activation. Each spinal segment is unique in this manner, as each arises from and maintains a specific HOX code (FIG. 24B). This code underlies the basis for rostro-caudal patterning and vertebral segmentation (FIG. 24C). The HOX code regulates numerous developmental processes such as eph/ephrin-mediated axonal guidance, controlling corticospinal axon exits for muscle innervation (FIG. 24D), and contributes to normal motor function of the mature organism.

Additional positional information is created within each spinal segment that confers dorso-ventral patterning ("back-to-front"), which creates the complex neuronal diversity of the spinal cord (FIG. 25). This neuronal diversity within a spinal segment is responsible for the relay circuitry of the central pattern generator, reflexes, and provides innervation terminals for the corticospinal tract. Together rostro-caudal and dorso-ventral patterning determine how the spine is created during development, how the spine functions normally during adulthood, and can play a role in spinal regeneration following injury.

Tissue damage that has occurred within a specific anatomical context has the highest potential to be repaired by grafts that belong in that specific context, known as orthotopic grafting. Previous work has demonstrated preferential innervation of forelimb corticospinal neurons into spinal cord controlling forelimb, while hindlimb corticospinal neurons similarly innervated spinal cord controlling hindlimb. This suggests region-specific cell identity plays an important role for axon guidance. Furthermore, recent publications have highlighted the importance of appropriate positional information for grafts to contribute to spinal regeneration. Unfortunately, due to technical limitations, most proposed transplantation strategies for the spinal cord are not orthotopic and currently fail to match the head-to-tail and back-to-front positional information of the transplanted cells with the injury site. Neural cell grafts in research and clinic trials are typically unspecified mixtures of progenitor cells derived from fetal brain or spinal cord, or the products of imprecise and poorly controlled pluripotent stem cell differentiation procedures that do not result in appropriate patterning.

Disclosed herein is improved speed and control of neural induction and patterning. One development of these new techniques is the ability to now precisely control, with high purity, both the rostro-caudal and dorso-ventral identity of human iPSC-derived spinal neural progenitors (see FIG. 26). This allows one to coordinate cell production according to the location where damage has occurred during spinal cord injury. Especially for patients whose injuries are highly variable with regard to location and completeness, this provides a valuable tool as it allows for a patient-specific approach to clinical care ure. This is an unmet need, as all other research currently conducted neglects this aspect of neuroanatomy.

It is believed that is that orthotopic grafting of hPSC-derived spinal tissue will have the greatest potential for spinal regeneration in patients. These orthotopic grafts will possess the best ability to integrate into a particular injury site and induce neural regeneration.

Materials/Methods/Results

Cell Production: Provided herein is are novel hPSC differentiation protocols that efficiently generate neuromesoderm cells, a common developmental progenitor for the axial musculoskeletal system and spinal cord. Through sequential, timed modulation of fibroblast growth factor, bone morphogenic protein, wnt, and hedgehog signaling, undifferentiated hPSCs (FIG. 28A) are induced to exit pluripotency, form Sox2/Brachyury (T) co-expressing neuromesoderm progenitors within 24 hours (FIG. 28B) and then proceed to generate either pure, rostral/dorsal HOXB4/PAX3-positive, or rostral/ventral HOXB4-positive/PAX3-negative spinal tissue by day 3 (FIG. 28C), or caudal/dorsal HOXC8/PAX3-positive or caudal/ventral HOXC8-positive/PAX3-negative spinal tissue by day 6. These cells are then matured into neuroblasts for transplantation into the nude rat caudal/dorsal spinal cord contusion injury model.

Animal Studies: A total of 40 nude rats will be used for this first study. Nude rats have been selected because they can readily accept xenografts because of their immune deficiency. All rats will receive a moderate contusive spinal cord injury at the 8th thoracic vertebra (Ultimate Horizons Impactor). Two weeks will be allowed to elapse before animals will be subjected to treatment. 10 rats each will be transplanted with one of four positional grafts. Each cohort from each transplant group will be maintained for six months following transplant to allow for animal recovery, graft integration, and corticospinal axonal migration. Six animals will be sacrificed following six months, spinal cords extracted, and analyzed utilizing standard histological and immuno-histochemical methods. Three animals from each cohort will undergo anterograde tracing, while the final three animals from each cohort will undergo retrograde tracing. Tracing studies will require an additional two to four weeks before sacrifice and analysis.

Transplantation of Positional Grafts. Two weeks post-injury, a 10 µl Hamilton syringe with a 32-gauge needle (0.5 inch long, 30° beveled tip) will be used to inject the cell grafts (10 µl, 500,000 cells/µl) into three separate and equal injection sites at the epicenter and 1 mm rostral and 1 mm caudal to the epicenter of the lesion. Cells will be injected at the rate of 1 µl/min using an automated microinjector. The injection needle will be left in situ for one minute after injection n to minimize cell regurgitation, and the tip will be then slowly withdrawn.

Histology and Immunohistochemistry. At the time of sacrifice, rats will be transcardially perfused, tissue cryoprotected, embedded, and cryosectioned into 20 µm serial parasagittal sections. Some sections will be stained with Luxol Fast Blue (LFB) (myelin stain) and heamotoxyolin and eosin (H and E) for general morphology. For fluorescence immunostaining, verified antibodies will be used to identify glial fibrillary acidic protein for astrocytes (GFAP), human nuclear antigen (hNA), human cytoplasmic marker (Stem121), beta-III Tubulin (TUJ1) to label immature and mature neurons, Ki-67 to label dividing cells, neuronal nuclei (NeuN) to label mature neurons, microtubule-associated protein 2 (MAP2) and serotonin 5HT. Sections will then be incubated with secondary antibodies conjugated to Alexa Fluor 488, 555, or 647. Negative controls will be obtained by omission of the primary antibody. DAP1 will counterstain DNA to aid identification of individual cells. The proportion of human transplanted cells (detected using HNA or SC121) expressing each specific identity will be calculated for each grafted rat spinal cord. The volume of cord cavitation will be determined as described previously. Briefly, the area of cavitation of each section will be traced using imaging software. The total spinal cord area of the sample will be measured. The total cavity volume and total spinal cord volume will be calculated using the Cavalieri method, and the percentage cavitation determined.

Retrograde Axon tracing. Fluorogold will be utilized to identify neurons in the cortex and brainstem who have intact axons through the site of injury. Under anaesthesia the wound will be re-opened at 6 months and the injury site re-exposed. Fluorogold will be injected into the spinal cord 1.5 mm caudal (below) to the injury site. 14 days after tracing, the animals will be perfused and the brains removed and processed. The whole brain will be cut with a cryostat at 40 µm thick sections. The sections will be examined under a fluorescent microscope and the labeled neurons counted for each rat in the motor cortex as well as red nucleus (a rostral midbrain region involved in motor coordination), lateral vestibular nucleus, reticular formation, raphe nucleus, and locus coeruleus.

Anterograde Axon tracing. Biotinylated dextran amine (BDA) will be utilized to identify corticospinal axons and determine whether there are axons traversing the injury site and whether the transplanted neurons can provide a relay system through the site of injury for those axons. In summary, under anesthesia the sensorimotor cortex will be exposed at 6 months and BDA will be injected as described previously. 28 days later, the animals will be perfused and spinal cord processed. The spinal cord will be cut with a cryostat at 20 µm thick sections. The transplanted cells will be detected with human cytoplasmic marker SC121 and the distance of BDA labelled corticospinal tract regeneration into the graft will be measured.

BIBLIOGRAPHY

1. Thomson J A, et al. 1998. Embryonic stein cell lines derived from human blastocysts. Science. 282(5391): 1145-1147.
2. Itskovitz-Eldor J, et al. 2000. Differentiation of human embryonic stem cells into embryoid bodies compromising the three embryonic germ layers. Mol Med. 6(2):88-95.
3. Xu C, et al. 2001. Feeder-free growth of undifferentiated human embryonic stem cells. Nat Biotechnol. 19(10): 971-974.
4. Zhang S C, et al. 2001. In vitro differentiation of transplantable neural precursors from human embryonic stem cells. Nat Biotechnol. 19(12):1129-1133.
5. Perrier A L, et al. 2004. Derivation of midbrain dopamine neurons from human embryonic stem cells. Proc Natl Acad Sci USA. 101(34): 12543-12548.
6. Rosier E S, et al. 2004. Long-term culture of human embryonic stem cells in feeder-free conditions. Dev Dyn. 229(2):259-274.
7. Beattie G M, et al. 2005. Activin a maintains pluripotency of human embryonic stem cells in the absence of feeder layers. Stem Cells. 23(4):489-495.
8. Ludwig T E, et al. 2006. Derivation of human embryonic stem cells in defined conditions. Nat Biotechnol. 24(2): 185-187.

9. Yao S, et al. 2006. Long-term self-renewal and directed differentiation of human embryonic stem cells in chemically defined conditions. Proc Natl Acad Sci USA. 103 (18):6907-6912.
10. Takahashi K, et al. 2007. Induction of pluripotent stein cells from adult human fibroblasts by defined factors. Cell. 131(5):861-872.
11. Chambers S M, et al. 2009. Highly efficient neural conversion of human es and ips cells by dual inhibition of smad signaling. Nat Biotechnol. 27(3):275-280.
12. Nagaoka M, et al. 2010. Culture of human pluripotent stem cells using completely defined conditions on a recombinant e-cadherin substratum. BMC Dev Biol. 10:60.
13. Zeng H, et al. 2010. Specification of region-specific neurons including forebrain glutamatergic neurons from human induced pluripotent stem cells. PLoS One. 5(7): e11853.
14. Chen G, et al. 2011. Chemically defined conditions for human ipsc derivation and culture. Nat Methods. 8(5): 424-429.
15. Jaeger I, et al. 2011. Temporally controlled modulation of fgf/erk signaling directs midbrain dopaminergic neural progenitor fate in mouse and human pluripotent stem cells. Development. 138(20):4363-4374.
16. Jin S, et al. 2012. A synthetic, xeno-free peptide surface for expansion and directed differentiation of human induced pluripotent stem cells. PLoS One. 7(11): e50880.
17. Miyazaki T, et al. 2012. Laminin e8 fragments support efficient adhesion and expansion of dissociated human pluripotent stem cells. Nat Commun. 3:1236.
18. Cong L, et al. 2013. Multiplex genome engineering using crispr/cas systems. Science. 339(6121):819-823.
19. Lippmann E S, et al. 2014. Defined human pluripotent stem cell culture enables highly efficient neuroepithelium derivation without small molecule inhibitors. Stem Cells. 32(4): 1032-1042.
20. Sharma A, et al. 2014. Human induced pluripotent stem cell-derived cardiomyocytes as an in vitro model for coxsackievirus b3-induced myocarditis and antiviral drug screening platform. Circ Res. 115(6):556-566.
21. Howden S E, et al. 2015. Simultaneous reprogramming and gene correction of patient fibroblasts. Stem Cell Reports. 5(6):1109-1118.
22. Nagaoka M, et al. 2015. Design of a vitronectin-based recombinant protein as a defined substrate for differentiation of human pluripotent stem cells into hepatocyte-like cells. PLoS One. 10(8): e0136350.
23. Cellular & gene therapy guidances. 2016. U.S. Food and Drug Administration; www.fda.gov/BiologicsBloodVaccines/GuidaneComplianceRegulatoryInformation/Guidances/Cellularand GeneTherapy/default.htm.
24. Kang H W, et al. 2016. A 3d bioprinting system to produce human-scale tissue constructs with structural integrity. Nat Biotechnol. 34(3):312-319.
25. Takahashi, K: Yamanaka, S (2006). "Induction of pluripotent stem cells from mouse embryonic and adult fibroblast cultures by defined factors". Cell. 126 (4): 663-76.
26. Keirstead H S, et al. 2005. Human embryonic stem cell-derived oligodendrocyte progenitor cell transplants remyelinate and restore locomotion after spinal cord injury. J Neurosci. 25(19):4694-4705.
27. Kogut I, et al. 2014. Differentiation of human induced pluripotent stem cells into a keratinocyte lineage. Methods Mol Biol. 1195:1-12.
28. Lippnmann E S, et al. 2015. Deterministic hox patterning in human pluripotent stem cell-derived neuroectoderm. Stem Cell Reports. 4(4):632-644.
29. Chal J, et al. 2016. Generation of human muscle fibers and satellite-like cells from human pluripotent stem cells in vitro. Nat Protoc. 11(10):1833-1850.
30. Gouti M, et al. 2014. In vitro generation of neuromesodermal progenitors reveals distinct roles for wnt signalling in the specification of spinal cord and paraxial mesoderm identity. PLoS Biol. 12(8): e1001937.
31. Walsh P, et al. 2017. Defined Culture Conditions Accelerate Small-molecule assisted Neural Progenitors from Human-induced Pluripotent Stem Cells. Cell Transplanation 26(12):1890-1902.
32. PMID 11163256 Prosencephalon Development
33. PMID 12461551 Parsing Prosencephalon
34. PMID 14960272 Early Forebrain Dev
34. PMID 19143049 Telencephalon Development
36. PMID 24014419 Neural Induction Brivanlou
37. PMID 20715182 Scholer Induction and FGF
38. PMID 20207225 Scholer Tesar FGF, Induction, Species
39. PMID 21997878 Wisco FGF/ERK, Induction All publications, patents and patent applications, as well accession numbers and the nucleotide and/or protein sequences that can be found therein, are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for inducing differentiation in stem cells, comprising,
 a) providing:
  i) a cell culture comprising pluripotent stem cells,
  ii) an inhibitor of Activin receptor-Like Kinase (ALK) 2/3 signaling, wherein said inhibitor is selected from the group consisting of Noggin, Dorsomorphin and LDN-193189 and mixtures thereof, and
  iii) an inhibitor of fibroblast growth factor (FGF) signaling and/or an inhibitor of Extracellular-Regulated Kinase (ERK) signaling, wherein said inhibitor of FGF is selected from the group consisting of SU5402, BGJ398, antibodies to FGF protein family members or their receptors and mixtures thereof, wherein said inhibitor of ERK is PD0325901
 b) exposing said pluripotent stem cells of i) simultaneously to culture medium containing inhibitors of ALK 2/3 signaling of ii) and inhibitors of FGF signaling and/or inhibitors of ERK signaling of iii); and
 c) inducing differentiation of said contacted pluripotent stem cells so as to generate a population of cultured anterior ectoderm cells.

2. The method of claim 1 further comprising patterning said ectoderm cells into telencephalic neuroepithelium expressing PAX6/FOXG1/SIX3/OTX2 comprising contacting said ectoderm cells with an inhibitor of WNT signaling.

3. The method of claim 1 further comprising patterning said ectoderm cells into ventral telencephalic neuroepithelium expressing PAX6/FOXG1/SIX3/OTX2 and NKX2.1 and/or NKX2.2 comprising contacting said ectoderm cells with an inhibitor of WNT signaling and/or an activator of sonic hedgehog pathway.

4. The method of claim 1 further comprising patterning said ectoderm cells into diencephalic neuroepithelium expressing PAX6/OTX2 comprising contacting said ectoderm cells with at least one activator of WNT signaling.

5. The method of claim 1 further comprising patterning said ectoderm cells into mesencephalic neuroepithelium that does not express PAX6, but does express OTX2 and/or PAX5 comprising contacting said ectoderm cells with at least one activator of WNT signaling.

6. The method of claim 5 further comprising converting said mesencephalic neuroepithlium into cranial neural crest stem cells expressing PAX3/SOX10/SOX9/OTX2 or PAX3/SOX10/SOX9/OTX2/PAX5 comprising contacting said mesencephalic neuroepithlium with an activator of the bone morphogenic protein pathway.

* * * * *